United States Patent [19]

York, Jr.

[11] Patent Number: 5,153,211

[45] Date of Patent: * Oct. 6, 1992

[54] SPIRO-TRICYCLICAROMATIC SUCCINIMIDE DERIVATIVES AS INHIBITORS OF ALDOSE REDUCTASE

[75] Inventor: Billie M. York, Jr., Crowley, Tex.

[73] Assignee: Alcon Laboratories, Inc., Fort Worth, Tex.

[*] Notice: The portion of the term of this patent subsequent to Aug. 27, 2002 has been disclaimed.

[21] Appl. No.: 750,785

[22] Filed: Aug. 27, 1991

Related U.S. Application Data

[60] Division of Ser. No. 402,035, Sep. 5, 1989, Pat. No. 5,070,100, which is a continuation-in-part of Ser. No. 94,636, Sep. 9, 1987, which is a continuation-in-part of Ser. No. 5,859, Jan. 21, 1987, Pat. No. 4,864,028, which is a continuation of Ser. No. 766,569, Aug. 14, 1985, abandoned, which is a continuation of Ser. No. 532,168, Sep. 14, 1983, Pat. No. 4,537,892.

[51] Int. Cl.$^5$ .............. A61K 31/42; A61K 31/425; C07D 263/52; C07D 277/60
[52] U.S. Cl. ................................. 514/369; 514/376; 514/409; 514/866; 548/147; 548/216; 548/411
[58] Field of Search .................. 548/147, 216, 411; 514/369, 376, 409

[56] References Cited

U.S. PATENT DOCUMENTS

| | | |
|---|---|---|
| 3,138,608 | 6/1964 | Davis . |
| 3,153,050 | 10/1964 | Davis . |
| 3,821,383 | 6/1974 | Sestanj et al. ................ 424/258 |
| 4,117,230 | 9/1978 | Sarges ............................. 548/309 |
| 4,127,665 | 11/1978 | Sarges et al. ................... 548/309 |
| 4,130,714 | 12/1978 | Sarges ............................. 548/309 |
| 4,209,630 | 6/1980 | Sarges ............................. 548/309 |
| 4,436,745 | 3/1984 | York, Jr. ........................ 548/308 |
| 4,438,272 | 3/1984 | York, Jr. ........................ 548/308 |
| 4,537,892 | 8/1985 | York, Jr. ........................ 548/147 |
| 4,803,193 | 2/1989 | Kanda et al. ................... 548/147 |
| 4,864,028 | 9/1989 | York, Jr. ........................ 548/147 |

FOREIGN PATENT DOCUMENTS 0065392 11/1982 European Pat. Off. .
0092385 10/1983 European Pat. Off. .

OTHER PUBLICATIONS

Winstead et al., Journal of Medicinal Chemistry, vol. 19, No. 2, pp. 279-286, 1976.
Pan et al., Journal of Medicinal Chemistry, vol. 10, No. 1, pp. 957-959, 1967.
Pan et al., Journal of Medicinal Chemistry, vol. 7, pp. 31-38, 1964.
Chemical Abstracts 87:184427(y), (1977), [Trigo, G. et al., An. Quim. (1977), 73(2), 282-4].
Chemical Abstracts, 91:56913w, (1979), [Trigo, G. et al., An. Quim. (1978), 74(7-8), 1090-1092].
Pan, Hsi-Lung et al., "Derivatives of Fluorene, XVIII, New Halogenofluorenes, I, Potential Antitumor Agents", J. Med. Chem., vol. 7, 1964, pp. 31-38.
Pan, Hsi-Lung et al., "Derivatives of Fluorene, XXIV, Synthesis and Antitumor Activities of Some Imidazolidine-2,5-Diones", J. Med. Chem., vol. 9, 1967, pp. 957-959.
Winstead, Meldrum B. et al., "Relationship of Molecular Structure to in Vivo Scintigraphic Distribution Patterns . . . ", J. Med. Chem., vol. 19, 1976, pp. 279-286.

Primary Examiner—Mary C. Lee
Assistant Examiner—MarySusan H. Gabilan
Attorney, Agent, or Firm—James Arno; Gregg C. Brown; Robert L. Price

[57] ABSTRACT

Disclosed are substituted or unsubstituted planar tricyclic fluorene or nuclear analogs thereof, spiro-coupled to a five-membered ring containing a secondary amide, and the pharmaceutically acceptable salts thereof. These compounds are useful, inter alia in the treatment of diabetes. Also disclosed are processes for the preparation of such compounds; pharmaceutical compositions comprising such compounds; and methods of treatment comprising administering such compounds and compositions when indicated for, inter alia, long term, prophylactic treatment of the diabetes syndrome. A particularly preferred class of compounds comprise difluoro-dialkoxy substituted spiro-(9H-fluorene-9,4'-imidazolidine)-2',5-diones.

7 Claims, No Drawings

SPIRO-TRICYCLICAROMATIC SUCCINIMIDE DERIVATIVES AS INHIBITORS OF ALDOSE REDUCTASE

CROSS REFERENCE TO RELATED APPLICATIONS

This is a division of application Ser. No. 402,035 filed Sep. 5, 1989, now U.S. Pat. No. 5,070,100, which is a continuation-in-part of Ser. No. 07/094,636, filed Sep. 9, 1987, which is a continuation-in-part of Ser. No. 07/005,859, filed Jan. 21, 1987, now U.S. Pat. No. 4,864,028, issued Sep. 5, 1989 (now abandoned), which is a continuation of Ser. No. 06/766,569, filed Aug. 14, 1985 (now abandoned), which is a continuation of Ser. No. 06/532,168, filed Sep. 14, 1983, now U.S. Pat. No. 4,537,892.

FIELD OF THE INVENTION

This invention relates to novel spiro-tricyclicaromatic succinimide derivatives and related spiro-heterocyclic analogs such as spiro-tricyclicaromatic-thiazolidine-dione, -imidazolidinedione, and -oxazolidine-dione derivatives. More particularly, the invention relates to spiro-tricyclicaromatic succinimide derivatives and related spiro-heterocyclic analogs which are useful to prevent diabetic cataract, nerve tissue damage, and certain vascular changes.

BACKGROUND ART

As disclosed in U.S. Pat. No. 3,821,383, aldose reductase inhibitors such as 1,3-dioxo-1H-benz[d,e]-isoquinoline-2-(3H)-acetic acid, and its derivatives, are useful as inhibitors of aldose reductase and alleviators of diabetes mellitus complications. Spiro-[chroman-4,4'-imidazolidine]-2',5'-dione and spiro-[imidazolidine-4,4'-thiochroman]-2,5-dione and their derivatives, disclosed in U.S. Pat. No. 4,130,714 and U.S. Pat. No. 4,209,630, are also indicated as being useful in this regard. Certain spiro-polycyclicimidazolidinedione derivatives from U.S. Pat. No. 4,181,728 have been demonstrated to have inhibitory activity against aldose reductase and polyol accumulation. U.S. Pat. No. 4,117,230 describes a series of spiro-hydantoin compounds which include the 6-fluoro and 6,8-dichloro derivatives of spiro-chroman imidazolidmediones. Spiro-fluorenhydantoin and its derivatives are disclosed in my prior U.S. Pat. Nos. 4,438,272 and 4,436,745, as being potent human and rat aldose reductase inhibitors which prevent polyol accumulation in lenticular and nervous tissues of diabetic and galactosemic rats and prevent cataract and nerve dysfunction in diabetic rats. Pan et al, J. Med. Chem. 7, 31–38 (1964), describes halogenofluorenes as potential antitumor agents, and Pan et al, J. Med. Chem. 10, 957–959 (1967), describes spiro [fluoren-9,4'-imidazolidine]-2',5'-diones as potential antitumor agents.

SUMMARY OF THE INVENTION

It is one object of the invention to provide a novel series of spiro-tricyclicaromatic succinimide derivatives and related spiro-heterocyclic analogs, and methods for their preparation, which compounds are useful as inhibitors of aldose reductase and alleviators of diabetes mellitus complications.

A still further object of the invention is to provide pharmaceutical compositions and methods for inhibiting aldoreductase and the treatment of diabetes mellitus wherein the active ingredient comprises a spiro-tricyclicaromatic succinimide derivative or spiro-heterocyclic analog.

Other objects and advantages of the present invention will become apparent as the description thereof proceeds.

In satisfaction of the foregoing objects of the invention, there is provided by the broadcast embodiment of the invention, substituted or unsubstituted planar tricyclic fluorene or nuclear analogs thereof, spiro-coupled to a five-membered ring containing a secondary amide, and the pharmaceutically acceptable salts thereof.

In further satisfaction of the foregoing objects and advantages, there are provided by the present invention spiro-tricyclic-aromatic imides of the formula:

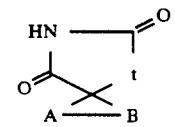

and the pharmaceutically acceptable metal salts and in cases, where the basic aromatic nitrogens are in the A, and/or B ring, the pharmaceutically acceptable organic and inorganic salts thereof, wherein A and B are aromatic or heterocyclic rings connected through two adjacent positions to a central five-membered ring, the A and B rings being selected from the group consisting of those of the formula:

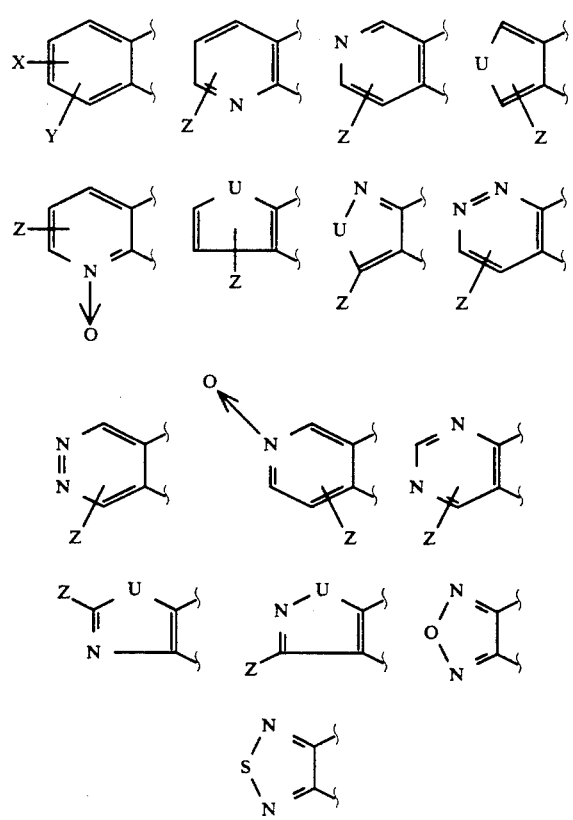

and wherein
U is selected from the group consisting of O, S, N-R$^1$;

X is selected from the group consisting of H, F, lower alkyl sulfide (e.g., —S—CH₃), lower alkylsulfinyl (e.g., —S(O)CH₃);

Y is selected from the group consisting of H, —OH, and

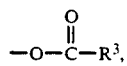

F, Cl, lower alkyl, lower alkoxy, lower alkylsulfide (e.g., —S—CH₃), lower alkylsulfinyl (e.g., —S(O)—CH₃), lower alkylsulfonyl (e.g., —SO₂CH₃), —CF₃, —S—CF₃, —SO₂CF₃, CO—N(R¹)—R², lower alkyl alcohol (e.g., —CH₂—OH), lower alkyl ether (e.g., —CH₂OCH₃), nitro, lower alkyl sulfide lower alkyl (e.g., —CH₂S—CH₃), lower alkylamine (e.g., —CH₂NH₂), lower alkyl esters (e.g., —CH₂—O—COCH₃), carboxylic acids and lower alkyl esters (e.g., —COOR³), lower alkyl carboxylic acids and esters (e.g., —CH(CH₃)—COOR¹), lower cycloalkyl (e.g., cyclopropyl); provided that when both of Rings A and B are phenyl, and one of X or Y is H or F, the other of X or Y must be other than H or F;

R¹ and R² are selected from the group consisting of H and lower alkyl (preferably methyl or ethyl);

R³ is lower alkyl (preferably methyl or ethyl);

Z is selected from the group consisting of H, lower alkyl (preferably methyl), and halogen (fluoro, chloro, bromo, iodo); and t is selected from the group consisting of NH, O, S, and CHR¹. Lower alkyl is defined as containing six or less carbon atoms.

Also provided are methods for preparation of the above described compounds, pharmaceutical compositions containing these compounds as the active ingredient, and methods for treatment of diabetic cataract, nerve tissue damage, and certain vascular changes utilizing the above described compounds as the active ingredient.

DESCRIPTION OF THE PREFERRED EMBODIMENTS

The present invention is concerned with novel spiro-tricyclicaromatic succinimide derivatives and related spiro-heterocyclic analogs such as spiro-tricyclicaromatic-thiazolidinedione, -imidazolidinedione, and -oxazolidinedione derivatives. The invention is also concerned with methods for preparation of these compounds, and methods for treatment of diabetic cataract, nerve tissue damage, and certain vascular changes using pharmaceutical compositions containing the compounds of the present invention as the active ingredient.

The compounds of the present invention are inhibitors of the enzyme aldose reductase and, while applicant is not bound by any theory, the pharmaceutical utility of the compounds of the present invention appears to correlate with their observed aldoreductase inhibitory property. The inhibition of the enzyme aldose reductase and related reductases results in the inhibition of abnormal polyol accumulation at the expense of NADPH in those tissues containing aldose reductase and/or related aldehyde reductases. The inhibition of the formation of a polyol, such as sorbitol or galactitol, arising from the reduction of an aldose, such as glucose or galactose respectively, is believes beneficial to delay the progression of certain complications arising from hyperglycemia or hypergalactocemia. Hyperglycemia is associated with the complications of neuropathy, retinopathy, cataract, glaucoma, and impaired wound healing in diabetes mellitus patients.

According to U.S. Pat. No. 3,821,383, aldose reductase inhibitors such as 1,3-dioxo-1H-benz [d,e]-isoquinoline-2-(3H)-acetic and its derivatives are useful as inhibitors of aldose reductase and alleviators of diabetes mellitus complications. Spiro-[chroman-4,4'-imidazolidine]-2',5'-dione and spiro-[imidazolidine-4,4'-thichroman]-2,5-dione and their derivatives from U.S. Pat. No. 4,130,714 and U.S. Pat. No. 4,209,630 have also proven useful in this regard. Certain spiro-polycyclicmidazolidinedione derivatives from U.S. Pat. No. 4,181,728 have been demonstrated to have inhibitory activity against aldose reductase and polyol accumulation. Spirofluorenhydantoin and its derivatives, according to the above-mentioned U.S. Pat. Nos. 4,438,272 and 4,436,745, are potent human and rat aldose reductase inhibitors which prevent polyol accumulation in lenticular and nervous tissues of diabetic and galactosemic rats and prevent cataract and nerve dysfunction in diabetic rats. Such compounds inhibit the reduction of aldoses such as glucose and galactose to sorbitol and galactitol, thus preventing the harmful accumulation of polyols in certain nervous, ocular, and vascular tissues. Effective aldose reductase inhibitor chemotherapy prevents, improves, or delays the onset, duration or expression of certain sequelae of diabetes mellitus which include ocular sequelae (e.g., cataract and retinopathy), kidney damage (nephropathy), neurological dysfunction (e.g., peripheral sensory neuropathy), vascular disease (e.g., diabetic micro- and macro-vasculopathies), impaired wound healing (e.g., impaired corneal reepithelialization) and heart disease. The discussion of the aldose reductase utility as described in U.S. Pat. No. 4,209,630 is hereby incorporated herein by reference.

As a result, the compounds of the present invention are of significant value as aldose reductase inhibitors, since it is already known in the art that aldose reductase inhibitors prevent diabetic cataract, nerve tissue damage, and certain vascular changes.

In accordance with the present invention, it has been surprisingly found that various spirocyclic imide containing derivatives of the tricycle fluorene and related heterocyclic analogs of fluorene and their derivatives are extremely useful as inhibitors of aldose reductase, especially human aldose reductase.

The spiro-cyclic aromatic imides of the present invention may be described by the following general formula:

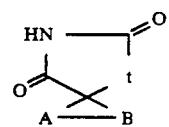

and the pharmaceutically acceptable metal salts and in cases, where basic aromatic nitrogens are in the A, and/or B rings, the pharmaceutically acceptable organic and inorganic acid salts thereof, wherein A and B are aromatic or heterocyclic rings connected through two adjacent positions to a central cycloalkyl ring, the A and B rings being selected from the group consisting of those of the formula:

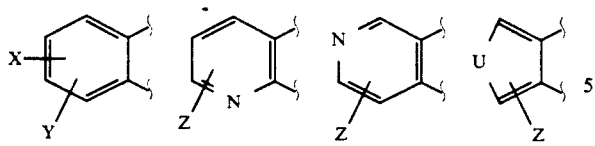
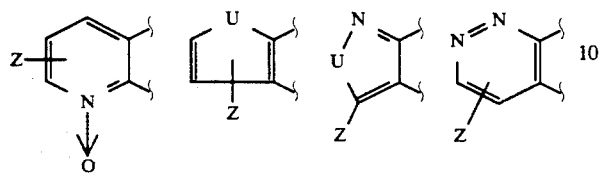
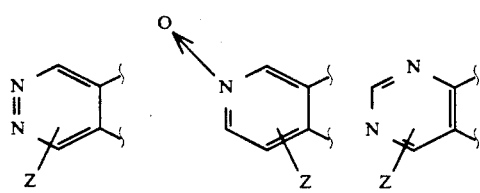
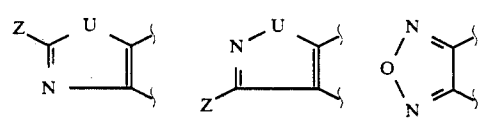
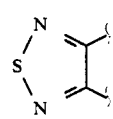
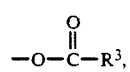

and wherein
U is selected from the group consisting of O, S, N—R$^1$;
X is selected from the group consisting of H, F, lower alkyl sulfide (e.g., —S—CH$_3$), lower alkylsulfinyl (e.g., —S(O)CH$_3$);
Y is selected from the group consisting of H, —OH, and $$-O-\overset{O}{\underset{\|}{C}}-R^3,$$

F, Cl, lower alkyl, lower alkoxy, lower alkylsulfide (e.g., —S—CH$_3$), lower alkylsulfinyl (e.g., —S(O)—CH$_3$), lower alkylsulfonyl (e.g., —SO$_2$CH$_3$), —CF$_3$, —S—CF$_3$, —SO$_2$CF$_3$, CO—N(R$^1$)—R$^2$, lower alkyl alcohol (e.g., —CH$_2$—OH), lower alkyl ether (e.g., —CH$_2$OCH$_3$), nitro, lower akyl sulfide lower alkyl (e.g., —CH$_2$S—CH$_3$), lower alkylamine (e.g., —CH$_2$NH$_2$), lower alkyl esters (e.g., —CH$_2$—O—COCH$_3$), carboxylic acids and lower alkyl esters (e.g., —COOR$^3$), lower alkyl carboxylic acids and esters (e.g., —CH(CH$_3$)—COOR$^1$), lower cycloalkyl (e.g., cyclopropyl); provided that when both of Rings A and B are phenyl, and one of X or Y is H or F, the other of X or Y must be other than H or F;
R$^1$ and R$^2$ are selected from the group consisting of H and lower alkyl (preferably methyl or ethyl);
R$^3$ is lower alkyl (preferably methyl or ethyl);
Z is selected from the group consisting of H, lower alkyl (preferably methyl), and halogen (fluoro, chloro, bromo, iodo); and t is selected from the group consisting of NH, O, S, and CHR$^1$.
In a more preferred embodiment, the spiro-cyclic aromatic imides of the present invention are of the following general formula:

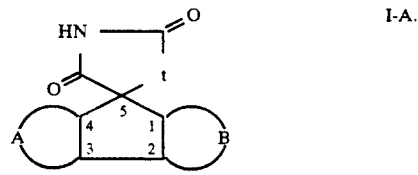

wherein A, B, U, X, Y, R$^1$, R$^2$, R$^3$, Z, and t are as described above. In more preferred embodiments, the cycloalkyl groups have 4 to 7 carbon atoms and lower alkyl groups have 1 to 6 carbon atoms. In an especially preferred embodiment, Ring A is selected from the foregoing group and Ring B is selected from the group consisting of the following:

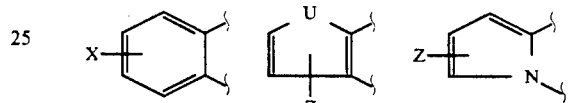
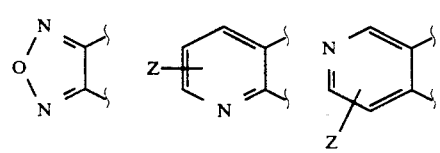
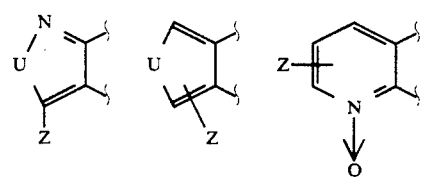
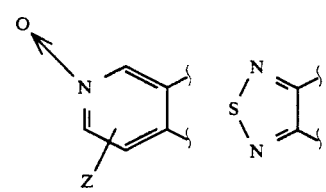

where X, U, and Z are described above. In the compounds of Formulae I and I-A, Rings A and B are attached to the central five-membered ring at positions 1,2 and 3,4.

The compounds of the present invention have important geometric and chemical similarities. These similarities include a planar, rigid tricyclic fluorene or fluorene-like aromatic ring system spiro-coupled to a five-membered imide (or cyclic secondary amide) ring such as succinimide, hydantoin, thiazolidinedione or oxazolidinedione. These spirocyclic derivatives of the various tricycles each contain a polarizable and hydrogen-bondable secondary amide, also called imide, radical (—CO—NH—CO—).

In those instances where, according to general Formulae I and I-A, A does not equal B, the spiro carbon is chiral. Activity of any such racemic mixture may be attributable to only one isomer. Resolution, or direct synthesis, of the enantiomers, as is known in the art, is recognized as a method to isolate or prepare the active or the more active enantiomer. It is also recognized that certain patterns of substitution on A and/or B according to Formulae I and I-A may create asymmetry, and the resulting diastereomeric mixtures may be separated by chromatography or solvent recrystallizations, as is known and practiced in the art. For example, if A has a methylsulfoxyl substituent and A is different from B, then there are at least two chiral centers: the spiro carbon and the sulfoxide sulfur. Physical separation of this diastereomeric mixture by chromatography or other methods practiced in the art will yield two racemic mixtures, each containing a pair of enantiomers. Stereospecific oxidation of a methylsulfido on A to yield a methylsulfoxide (e.g., via sodium metaperiodate and albumin) when A is different than B (according to Formula I) will yield a diastereomeric mixture, which then can be separated by conventional physical methods known in the art, such as liquid chromatography or differential solvent solubility, to yield the purified diastereomers which are themselves purified optical isomers. Reduction of the two optically active sulfoxide diastereomers will yield the optically active pair of enantiomers or mirror image isomers.

Of special interest in this invention are typical and preferred specie of Formula I such as these racemic mixtures: spiro-(6-fluoro-4H-indeno[1,2-b]thiophen-4,4'-imidazolidine)-2',5'-dione; spiro-(7-fluoro-9H-pyrrolo[1,2-a]indol-9,4'-imidazolidine)-2',4'-dione; spiro-(2-fluoro-9H-fluoren-9,4'-imidazolidine)-2',5'-dione; spiro-(6-fluoro-8H-indeno[2,1-b]thiophen-8,4'-imidazolidine)-2',5'-dione; spiro-(2-fluoro-9H-fluoren-9,3'-succinimide); spiro(2-fluoro-9H-fluoren-9,5'-thiazolidine)-2',4'-dione; spiro-(7-fluoro-9H-indeno[2,1c]pyridin-9,4'-imidazolidine)-2',5'-dione; spiro-(7-fluoro-5H-indeno[1,2-b]pyridin-5,4'-imidazolidine)-2',5'-dione; spiro-(7-fluoro-5H-indeno[1,2-c]pyridin-5,4'-imidazolidine)-2',5'-dione; spiro-(7-fluoro-9H-indeno[2,1-b]pyridin-5,4'-imidazolidine)-2',5'-dione; spiro-(7-fluoro-5H-indeno[1,2-c]pyridin-5,5'-thiazolidine)-2',4'-dione; spiro-(7-fluoro-5H-indeno[1,2-b]pyridin-5,5'-thiazolidine)-2',4'-dione; spiro-(7-fluoro-9H-indeno[2,1-c]pyridin9,5'-thiazolidine)-2',4'-dione; spiro-(7-fluoro-9H-[2,1-b]pyridin-9,5'-thiazolidine)-2',4'-dione; spiro-(7-fluoro-5H-indeno[1,2-b]pyridin-5,3'-succinimide; spiro-(7-chloro-5H-[1,2-b]pyridin-5,5'-thiazolidine)-2',4'-dione; spiro-(7-chloro-5H-[1,2-b]pyridin-5,5'-oxazolidine)-2',4'-dione; spiro-(6-fluoro-4H-indeno[1,2-b]thiophen-4,5'-thiazolidine)-2',4'-dione; spiro-(6-chloro8 H-indeno[2,1-b]thiophen-8,5'-thiazolidine)-2',4'-dione; spiro-(2-fluoro,7-methylthiol-9H-fluoren-9-,5'-thiazolidine)-2',4'-dione.

The compound of Formula I identified below by means of both linear nomenclature and structural formulas are also of special interest:

| COMPOUND | NAME |
|---|---|
| 1 | 2-METHYL-7-FLUOROSPIRO[5H-INDENO[1,2-b]PYRIDIN-5,4'-IMIDAZOLIDINE]-2',5'-DIONE |
| 2 | 2-METHYL-7-FLUOROSPIRO[5H-INDENO[1,2-b]PYRIDIN-5,5'-OXAZOLIDINE]-2',4'-DIONE |
| 3 | 2,7-DIFLUORO-4-METHYLSPIRO[9H-FLUORENE-9,3'-PYRROLIDINE]-2',5'-DIONE (IC50 = 2.8 × $10^{-9}$ M)* |
| 4 | 7,9-DIFLUORO-2-METHYLSPIRO[5H-INDENO[1,2-b]PYRIDIN-5,3'-PYRROLIDINE]-2',',5'-DIONE |
| 5 | 2,7-DIFLUORO-4-METHYLSPIRO[9H-FLUORENE-9,5'-THIAZOLIDINE]-2',4'-DIONE |
| 6 | 2,4,5,7-TETRAFLUOROSPIRO[9H-FLUORENE-9,3'-PYRROLIDINE]-2',5'-DIONE |
| 7 | 2,4,5,7-TETRAFLUOROSPIRO[9H-FLUORENE-9,5'-THIAZOLIDINE]-2',4'-DIONE (IC50 = 1.7 × $10^{-8}$ M)* |
| 8 | 2,4,5,7-TETRAFLUOROSPIRO[9H-FLUORENE-9,5'-OXAZOLIDINE]-2',4'-DIONE |
| 9 | 2,4,5,7-TETRAFLUOROSPIRO[9H-FLUORENE-9,4'-IMIDAZOLIDINE]-2',5'-DIONE (IC50 = 1.2 × $10^{-8}$ M)* |
| 10 | 2,7-DIFLUORO-4-METHYLSPIRO[9H-FLUORENE-9,5'-OXAZOLIDINE]-2',4'-DIONE |
| 11 | 2,7-DIFLUORO-4-METHYLSPIRO[9H-FLUORENE-9,4'-IMIDAZOLIDINE]-2',5'-DIONE (IC50 = 1.28 × $10^{-8}$ M)* |
| 12 | 7,9-DIFLUOROSPIRO[5H-INDENTO[1,2-c]PYRIDIN-5,3'-PYRROLIDINE]-2',5'-DIONE |
| 13 | 7,9-DIFLUOROSPIRO[5H-INDENO[1,2-c]PYRIDIN-5,4'-IMIDAZOLIDINE]-2',5'-DIONE |
| 14 | 7,9-DIFLUOROSPIRO[5H-INDENO[1,2-c]PYRIDIN-5,5'-OXAZOLIDINE]-2',4'-DIONE |
| 15 | 2,7-DIFLUORO-4-METHOXYSPIRO]9H-FLUORENE-9,5'-OXAZOLIDINE]-2',4'-DIONE |
| 16 | 2,7-DIFLUORO-4-METHOXYSPIRO[9H-FLUORENE-9,4'-IMIDAZOLIDINE]-2',5'-DIONE (IC50 = 9.4 × $10^{-9}$ M)* |
| 17 | 2,7-DIFLUORO-4-METHOXYSPIRO[9H-FLUORENE-9,3'-PYRROLIDINE]-2',5'-DIONE (IC50 = 4.8 × $10^{-9}$ M)* |
| 18 | 2,7-DIFLUORO-4-METHOXYSPIRO[9H-FLUORENE-9,5'-THIAZOLIDINE]-2',4'-DIONE |
| 19 | 2,4,7-TRIFLUORO-5-METHYLSPIRO[9H-FLUORENE-9,5'-THIAZOLIDINE]-2',4'-DIONE |
| 20 | 2,9-DIFLUORO-2-METHYLSPIRO[5H-INDENO[1,2-b]PYRIDIN-5,5'-OXAZOLIDINE]-2',4'-DIONE |
| 21 | 7,9-DIFLUORO-2-METHYLSPIRO[5H-INDENO[1,2-b]PYRIDIN-5,3'-PYRROLIDINE]-2',5'-DIONE |
| 22 | 7,9-DIFLUORO-2-METHYLSPIRO[5H-INDENO[1,2-b]PYRIDIN-5,4'-IMIDAZOLIDINE]-2',5'-DIONE (IC50 = 4.8 × $10^{-8}$ M)* |
| 23 | 2,4,7-TRIFLUORO-5-METHYLSPIRO[9H-FLUORENE-9,3'-PYRROLIDINE]-2',5'-DIONE |
| 24 | 2,4,7-TRIFLUORO-5-METHYLSPIRO[9H-FLUORENE-9,5'-OXAZOLIDINE]-2',4'-DIONE |
| 25 | 2,4,7-TRIFLUORO-5-METHYLSPIRO[9H-FLUORENE-9,4'-IMIDAZOLIDINE]-2',5'-DIONE |
| 26 | 2,4,7-TRIFLUORO-5-METHOXYSPIRO[9H-FLUORENE-9,5'-THIAZOLIDINE]-2',4'-DIONE |
| 27 | 2,4,7-TRIFLUORO-5-METHOXYSPIRO[9H-FLUORENE-9,3'-PYRROLIDINE]-2',5'-DIONE |
| 28 | 2,4,7-TRIFLUORO-5-METHOXYSPIRO[9H-FLUORENE-9,4'-IMIDAZOLIDINE]-2',5'-DIONE (IC50 = 1.13 × $10^{-5}$ M)* |
| 29 | 2,4,7-TRIFLUORO-5-METHOXYSPIRO[9H-FLUORENE-9,5'-THIAZOLIDINE]-2',4'-DIONE |
| 30 | 2,4,7-TRIFLUORO-5-METHYLTHIOSPIRO[9H-FLUORENE-9,3'-PYRROLIDINE]-2',5'-DIONE |
| 31 | 2,4,7-TRIFLUORO-5-METHYLTHIOSPIRO[9H-FLUORENE-9,4'-IMIDAZOLIDINE]-2',5'-DIONE |
| 32 | 2,7-DIFLUORO-4-METHYLSULFINYLSPIRO[9H-FLUORENE-9,5'-OXAZOLIDINE]-2',4'-DIONE |
| 33 | 2,4,7-TRIFLUORO-5-METHYLTHIOSPIRO[9H-FLUORENE-9,5'-OXAZOLIDINE]-2',4'-DIONE |
| 34 | 2,7-DIFLUORO-4-METHYLTHIOSPIRO[9H-FLUORENE-9,4'-IMIDAZOLIDINE]-2',5'-DIONE (IC50 = 1.75 × $10^{-8}$ M)* |
| 35 | 2,7-DIFLUORO-4-METHYLSULFINYLSPIRO[9H-FLUORENE-9,4'-IMIDAZOLIDINE]-2',5'-DIONE |
| 36 | 2,7-DIFLUORO-4-METHYLTHIOSPIRO[9H-FLUORENE-9,5'-OXAZOLIDINE]-2',4'-DIONE |
| 37 | 2,7-DIFLUORO-4-METHYLSULFINYLSPIRO[9H-FLUORENE-9,3'-PYRROLIDINE]-2',5'-DIONE |
| 38 | 2,7-DIFLUORO-4-METHYLTHIOSPIRO[9H-FLUORENE-9,3'-PYRROLIDINE]-2',5'-DIONE |
| 39 | 3,7-DIFLUORO-9-METHYLSPIRO[5H-INDENO[1,2-b]PYRIDIN-5,5'-THIAZOLIDINE]-2',4'-DIONE |
| 40 | 3,7-DIFLUORO-9-METHYLTHIOSPIRO[5H-INDENO[1,2-b]PYRIDIN-5,5'-THIAZOLIDINE]-2',4'-DIONE |
| 41 | 3,7-DIFLUORO-9-METHYLSPIRO[5H-INDENO[1,2-b]PYRIDIN-5,3'-PYRROLIDINE]-2',5'-DIONE |
| 42 | 7-FLUORO-5-METHYLTHIOSPIRO[9H-PYRROLO[1,2-a]INDOL-9,4'-IMIDAZOLIDINE]-2',5'-DIONE |
| 43 | 3,7-DIFLUORO-9-METHYLSPIRO[5H-INDENO[1,2-b]PYRIDIN-5,4'-IMIDAZOLIDINE]-2',5'-DIONE (IC50 = 1.61 × $10^{-8}$ M)* |

-continued

| | |
|---|---|
| 44 | 3,7-DIFLUORO-9-METHYLTHIOSPIRO[5H-INDENO[1,2-b]PYRIDIN-5,3'-PYRROLIDINE]-2',5'-DIONE |
| 45 | 3,7-DIFLUORO-9-METHYLSPIRO[5H-INDENO[1,2-b]PYRIDIN-5,5'-OXAZOLIDINE]-2',4'-DIONE |
| 46 | 3,7-DIFLUORO-9-METHYLTHIOSPIRO[5H-INDENO[1,2-b]PYRIDIN-5,5'-OXAZOLIDINE]-2',4'-DIONE |
| 47 | 3,7-DIFLUORO-9-METHYLTHIOSPIRO[5H-INDENO[1,2-b]PYRIDIN-5,4'-IMIDAZOLIDINE]-2',5'-DIONE |
| 48 | 5,7-DIFLUORO-2-METHYLTHIOSPIRO[9H-PYRROLO[1,2-a]INDOL-9,4'-IMIDAZOLIDINE]-2',5'-DIONE |
| 49 | 5,7-DIFLUORO-3-METHYLSPIRO[9H-PYRROLO[1,2-a]INDOL-9,4'-IMIDAZOLIDINE]-2',5'-DIONE |
| 50 | 7-FLUORO-5-METHOXYSPIRO[9H-PYRROLO[1,2-a]INDOL-9,4'-IMIDAZOLIDINE]-2',5'-DIONE |
| 51 | 5,7-DIFLUORO-2-METHYLSULFINYLSPIRO[9H-PYRROLO[1,2-a]INDOL-9,4'-IMIDAZOLIDINE]-2',5'-DIONE |
| 52 | 7-FLUORO-5-METHYLSPIRO[9H-PYRROLO[1,2-a]INDOL-9,4'-IMIDAZOLIDINE]-2',5'-DIONE |

*IC50 values are based on inhibition of rat lens aldose reductase.

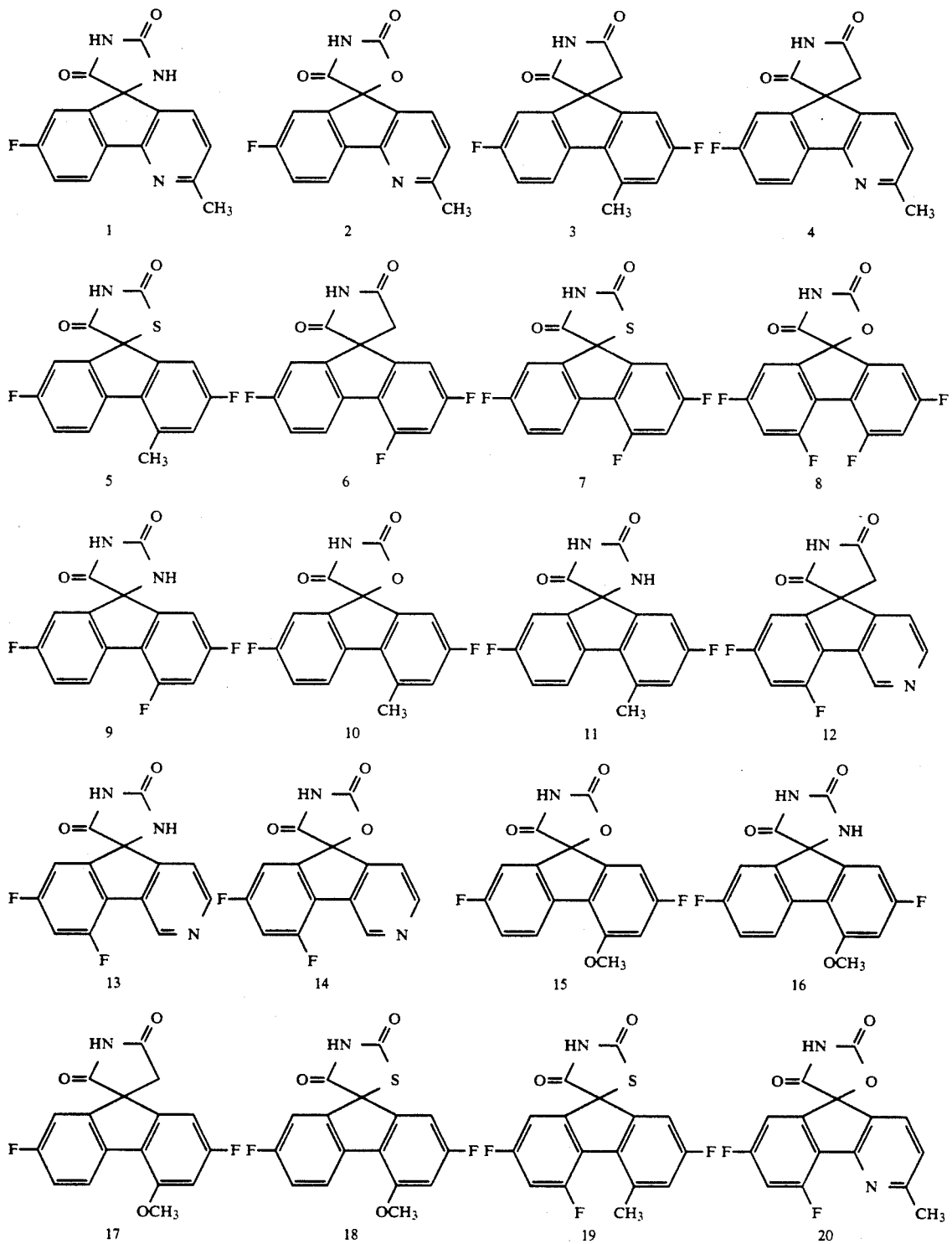

-continued
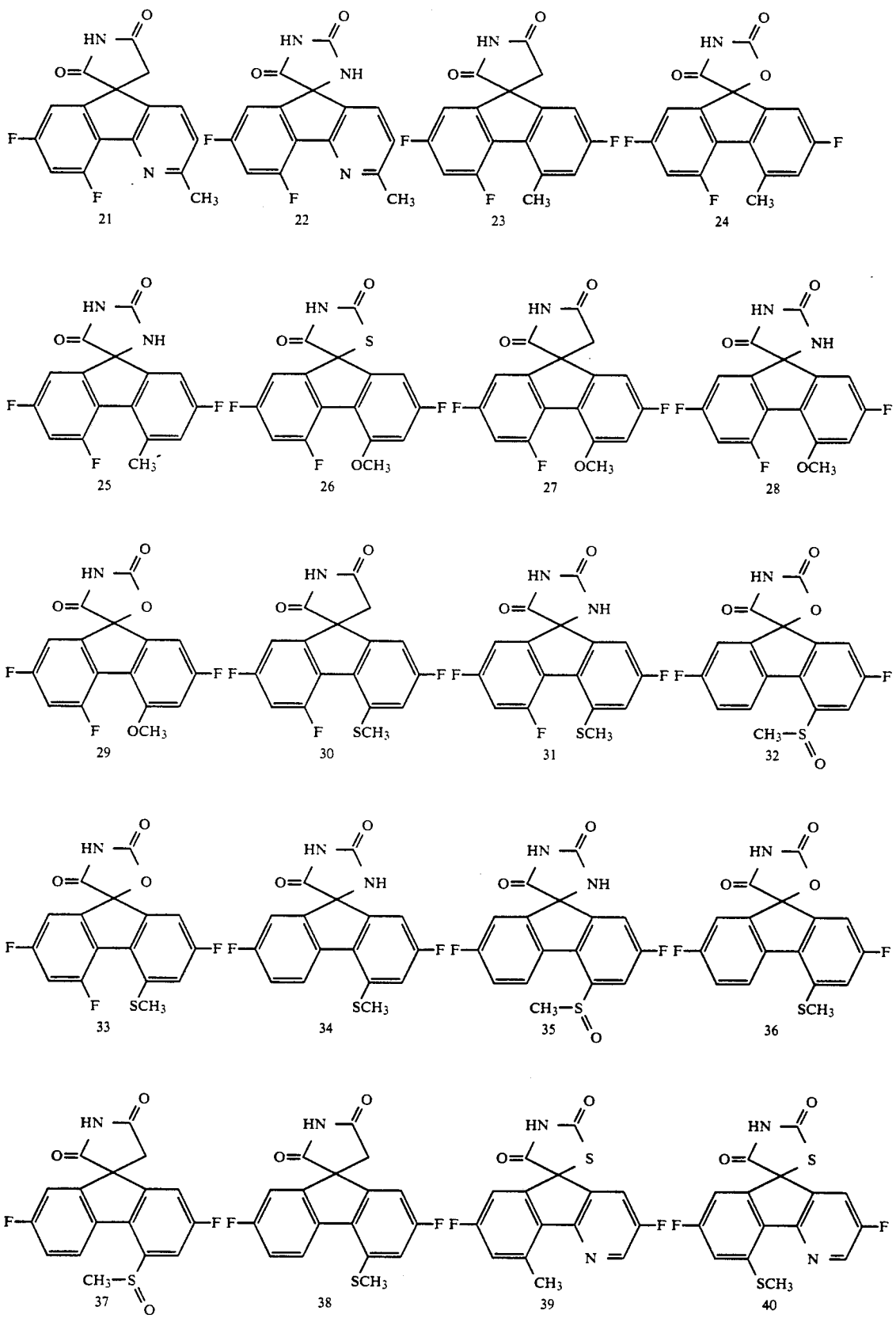

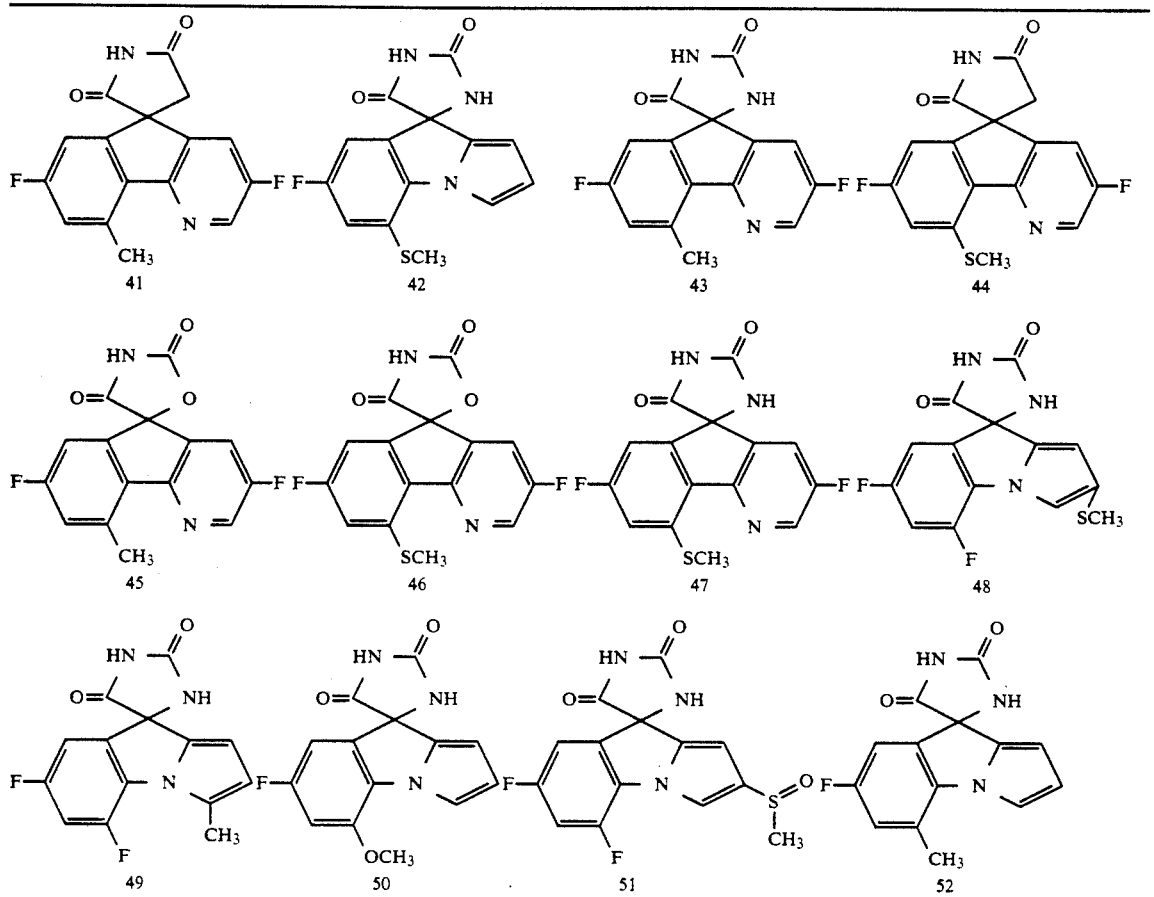

Also of special interest in this invention are these achiral or nonracemic compounds: spiro-(2,7-difluoro-9H-fluoren-9,4'-imidazolidine)-2',5'-dione; spiro-(2,7-difluoro-9H-fluoren-9,5'-thiazolidine)-2',4'-dione; spiro-(2,7-difluoro-9H-fluoren-9,3'-succinimide); spiro-(2,7-difluoro-9H-fluoren-9,5'-oxazolidine)-2',4'-dione. All the aforementioned compounds are highly potent as regards their aldose reductase inhibitory activities. All of the aforementioned preferred compounds as in Formula I may be formulated as the base salts thereof with pharmacologically acceptable cations (e.g., sodium salt). Alternatively, several preferred examples such as spiro-(7-fluoro-5H-indeno[1,2-b]pyridin-5,5'-thiazolidine)-2',4'-dione and related examples which contain a basic nitrogen in ring(s) A and/or B according to Formula I can be formulated as the acid salt with pharmacologically acceptable strong acids (e.g., hydrochloride salt).

The novel compounds of the present invention are readily prepared from appropriate ketones of Formula II of their methylene analogs of Formula III:

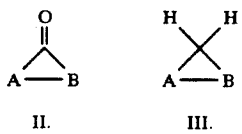

wherein A and B are previously defined with the exception that introduction of a nitro substituent(s) is conducted after hydantoin derivatization. Similarly, certain other derivatizations, e.g., esterification of carboxylic acids, oxidation of alkyl sulfides to sulfoxides or sulfones and direct aromatic halogenations may be conveniently performed after the tricyclic aromatic is spiro-imide derivatized, e.g., converted to the hydantoin or thiazolidinedione. In addition, certain labile protecting groups may be employed as is known and practiced in the art.

The four major derivatization methods to transform tricycles of Formulas II and III into derivatives of Formula I follow.

METHOD I—SPIRO-TRICYCLICIMIDAZOLIDINEDIONES (HYDANTOIN DERIVATIZATION)

The novel spiro-hydantoin derivatives of the present invention are readily prepared from appropriate ketones of Formula II, wherein A and B are previously defined. For example, spiro-imidazolidinedione derivatives (29) and (41) are prepared respectively from 5H-indeno[1,2-b]pyridin-5-one and 9H-pyrrolo[1,2-a]indolin-9-one:

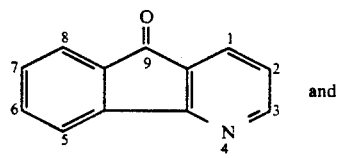

and

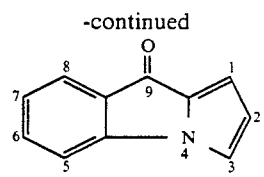

Similarly, spiro-imidazolidinedione derivative (39) is prepared from its starting material ketone 8H-indeno[2,1-b]thiophen-8-one:

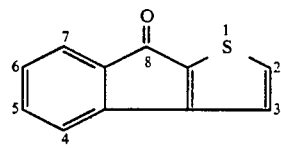

To synthesize a spiro-imidazolidinedione derivative, the ketone in Formula II is condensed with an alkali metal cyanide, such as potassium cyanide, and ammonium carbonate. The reaction is typically conducted in the presence of a ketone solubilizing inert polar organic solvent which include, but is not limited to, water miscible alcohols such as ethanol and isopropanol, lower alkylene glycols such as ethylene glycol and trimethylene glycol, N,N-di(lower alkyl), lower alkanoamides such as N,N-dimethyl-formamide, acetamide. In general, the reaction is conducted at temperatures ranging from 60° C. to about 180° C. (preferably 100° C. to 130° C.) for 6 hours to about 4 days, depending upon the ketone, solvent and temperature used. In general reagents in this reaction are employed in excess of stoichiometric amounts to provide maximum conversion of the ketone substrate to the spirohydantoin derivative. For example, a moderate excess of potassium cyanide (i.e., 1.1 equiv) and a 1.5 to 4 fold excess of ammonium carbonate achieves an increased yield of spirohydantoin derivative based upon ketone starting material. Reaction ketone substrates of Formula II are prepared by methods known to those skilled in the art. Typical preparative methods for substrate ketones are represented by, but are not limited to, examples in Table A and in the example preparations which follow.

METHOD II—SPIRO-TRICYCLICTHIAZOLIDINEDIONES

The novel spiro-tricyclicthiazolidinedione derivatives of the present invention are readily prepared from appropriate fluorene and heterocyclic analogs of fluorene derivatives of Formula III, wherein A and B are previously defined. For example, spiro-thiazolidinedione derivative (26) is prepared from 5H-indeno[1,2-b]pyridine:

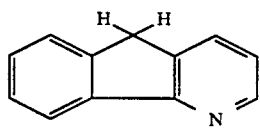

Likewise, the spiro-thiazolidinedione of example (12) is prepared from its starting material 2-fluoro-9H-fluorene:

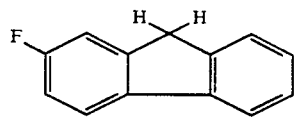

The synthesis of a spiro-thiazolidinedione from the corresponding tricyclic fluorene or heterocyclic fluorene derivative is a multistepped synthesis as depicted in Example IV. The first step involves metalation with a lower alkyl lithium reagent such as n-butyllithium in an inert aprotic solvent such as diethyl ether or tetrahydrofuran under an inert atmosphere of nitrogen or argon, e.g., metalation of 2-fluoro-9H-fluorene:

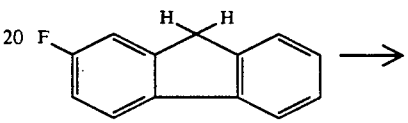

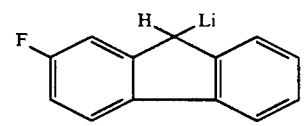

Metalation occurs primarily at the methylene bridge. Reaction with carbon dioxide results in carbonation of the bridge carbon to yield upon isolation the carboxylic acid, e.g., 2-fluoro-9H-fluoren-9-carboxylic acid:

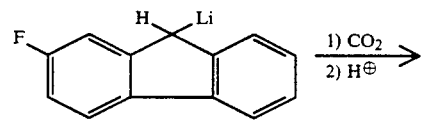

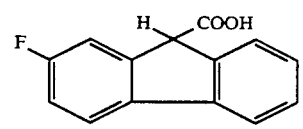

Isolation of the carboxylic acid derivative can be accomplished by a process including acidification, simple column chromatography and solvent recrystallization similar to the process cited in Example IV. In contrast to this general case, metalation and carbonation of 8H-indeno[1,2-c] thiophene results in a significant formation of 8H-indeno[1,2-c] thiophene-1-carboxylic acid and 8H-indeno[1,2-c] thiophene-3-carboxylic acid in addition to the desired 8H-indeno [1,2-c] thiophene-8-carboxylic acid, MacDowell and Jefferies; *J. Org. Chem.*, 35 (1970) 871. The tricyclic carboxylic acid product is then esterified with a lower alkylalcohol such as methanol in the presence of an acid catalyst such as a hydrogen halide, such as hydrochloric acid. In a typical procedure, the acid (e.g., 2-fluoro-9H-fluorene-9-carboxylic acid) is esterified by the addition of acetyl chloride to methanolic solution of the carboxylic acid with reflux:

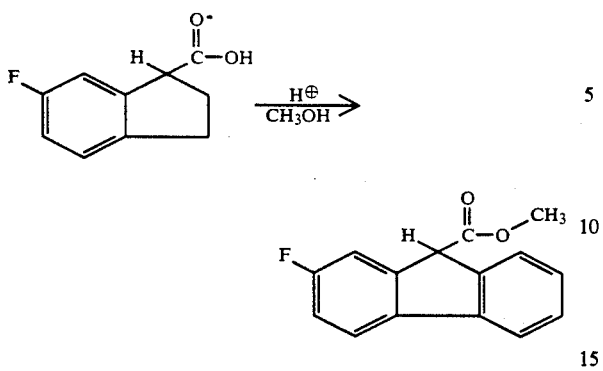

Proton abstraction from the acidic methine bridge of the carboxylic ester by an alkali alkoxide such as sodium metal in methanol or alkali hydride such as potassium hydride in DMSO or DMF generates a carbanion. Introduction of purified dry oxygen results in oxidation of the methine carbon. Bisulfite reduction and a simple work-up involving filtration results in the isolation of an α-hydroxy ester product, e.g., 2-fluoro-9-hydroxy-9H-fluoren-9-carboxylic acid methyl ester:

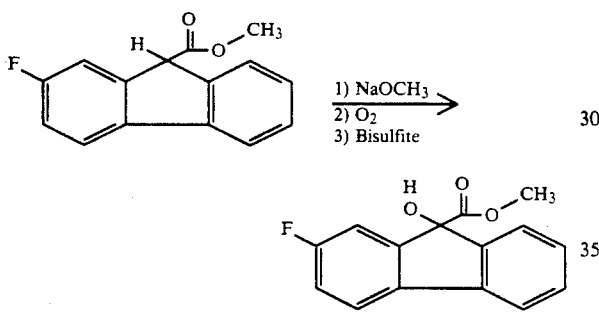

α-Halogenation of the α-hydroxy ester by a thionyl halide such as thionyl chloride at reflux transforms 2-fluoro-9-hydroxy-9H-fluoren-9-carboxylic acid methyl ester into 9-chloro-2-fluoro-9H-fluoren-9-carboxylic acid methyl ester:

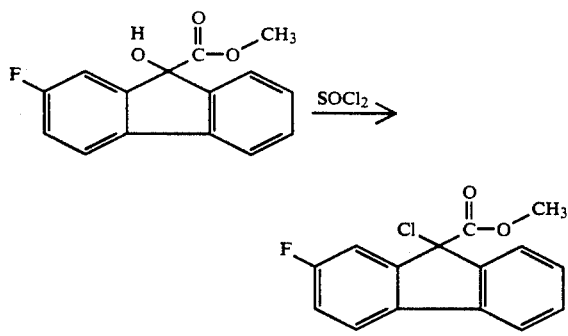

In a typical work-up procedure the cooled reaction mixture is diluted with benzene or a similar inert solvent, as known to those skilled in the art, and the solution is evaporated with reduced pressure and heat to yield the α-halo ester. The α-halo ester, e.g., 9-chloro-2-fluoro-9H-fluoren-9-carboxylic acid methyl ester, is reacted with thiourea in an anhydrous polar high boiling relatively nonbasic solvent such as dioxane at reflux for 6-24 hours. Work-up and simple chromatography as is known to those skilled in the art results in the isolation of a spiro-tricyclicaminothiazolone product, e.g., spiro-[2-fluoro-9H-fluoren-9,5'-(2'-amino-4'-thiazolone]:

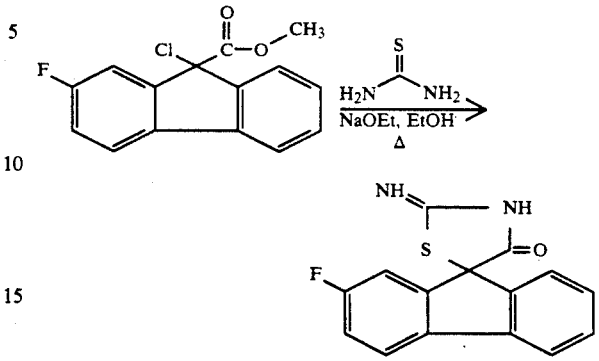

Hydrolysis of the spiro-aminothiazolone in an acidic aqueous alcoholic solution such as concentrated hydrochloric acid in methanol yields the spiro-thiazolidinedione, e.g., spiro-(2-fluoro-9H-fluorene-9,5'-thiazolidine)-2',4'-dione.

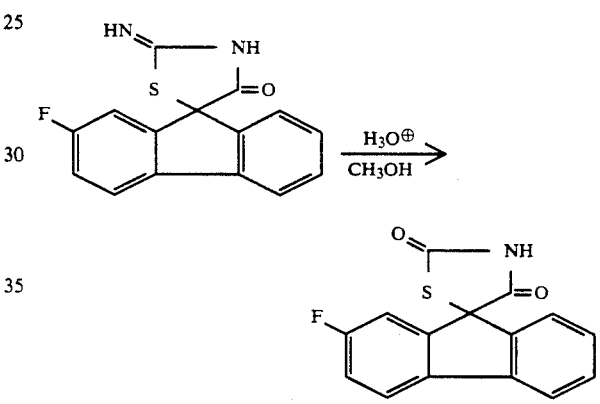

Reaction starting materials, tricyclic fluorene and tricyclic heterocyclic flourene derivatives of Formula III, are prepared by methods known to those skilled in the art. Typical preparative methods are represented by, but are not limited to, preparation examples of Table A and in the examples which later follow.

METHOD III—SPIRO-TRICYCLICOXAZOLIDINEDIONES

The novel spiro-tricyclic-oxazolidinedione derivatives of the present invention are readily prepared from appropriate derivatives of flourene and heterotricyclic analogs of fluorene of Formula III, wherein A and B are previously defined. The synthesis of the spiro-oxazolidinediones and spiro-thiazolidinediones (see II) generally have common synthetic intermediates. For example, spiro-tricyclicoxazolidinedione derivative (6) is prepared from the tricyclic α-hydroxy ester, 2-fluoro-9-hydroxy-9H-fluorene-9-carboxylic acid methyl ester, which is an intermediate in the synthesis of spiro-tricyclic-thiazolidinedione (12). Reaction of the α-hydroxy ester with 1 to 2 (preferably 1.1) equivalents of urea and 1 to 2 (preferably 1.05) equivalents of an alkali alkoxide in a lower alkyl alcohol at reflux such as sodium ethoxide in ethanol yields the spiro-tricyclic-oxazolidinedione. The isolation procedure involves the addition of water to the reaction, acidification with a mineral acid such as hydrochloric acid, simple filtration and column chromatography. Such common product isolation procedures are well known to those skilled in the art. The isolated product, in this example, is spiro-(2-fluoro-9H-fluorene-9,5'-oxazolidinedione)-2',4'-dione. Similarly, other tricyclic α-hydroxy esters known in the art are derived from the appropriate fluorene derivatives and heterotricyclic analogs of fluorene derivatives, as are represented in but not limited by those examples cited in Table A and in the following example preparations, can be utilized to prepare spiro-tricyclicoxazolidinediones according to this general scheme:

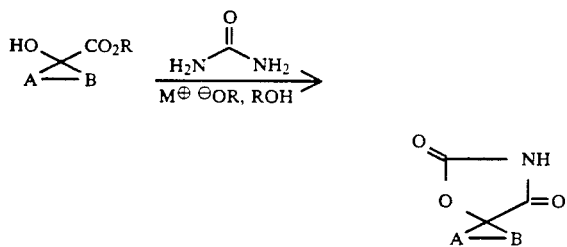

M+ = alkali metal cation (e.g., Na+)
R = lower alkyl (e.g., methyl)
A and B are as previously defined.

METHOD IV—SPIRO-TRICYCLICSUCCINIMIDES

The novel spiro-tricyclicsuccinimide derivatives of the instant invention are readily prepared from appropriate fluorene derivatives and heterocyclic analogs of fluorene of Formula III, wherein A and B are previously defined. The synthesis of the spiro-tricyclicsuccinimides, spiro-oxazolidinediones and spiro-thiazolidinediones generally have common synthetic intermediates. For example, spiro-tricyclicsuccinimide derivatives (20) and (21) are prepared from the tricyclic acid esters, 9H-fluorene-9-carboxylic acid methyl ester and 2-fluoro-9H-fluorene-9-carboxylic acid methyl ester respectively which are intermediates in the synthesis of spiro-tricyclicthiazolidinediones (9) and (12) and spiro-tricyclicoxazolidinediones (2) and (6). Reaction of the carboxylic alkyl ester with 1 to 1.5 equivalents (preferably 1.1) of an alkali metal alkoxide such as sodium methoxide in an alkyl alcohol such as methanol followed by reaction with 1-2 equivalents (preferably 1.1) of 2-haloacetamide such as 2-chloroacetamide (Aldrich Chemical, Inc.) at 10° to 50° C. (preferably ambient temperature) under an inert atmosphere such as nitrogen for a period of 8 hrs. to 4 days depending upon temperature, haloacetamide reagent and solvent employed. Typical reaction times with methanol solvent, chloroacetamide reagent at room temperature can be 48 hrs. The reacted mixture is typically poured into 1–4X volume of 1-5% alkali hydroxide such as 2.5% sodium hydroxide. Insolubles are removed by filtration. The filtrate is acidified with a dilute or concentrated mineral acid such as concentrated hydrochloric acid and the resulting precipitate is collected by filtration with cold water wash. Solvent recrystallizations may be employed as is known in the art to further purify the resulting spiro-tricyclicsuccinimide product. Specifically, 9H-fluorene-9-carboxylic acid methyl ester and 2-fluoro-9H-fluorene-9-carboxylic acid methyl ester yield respectively, after the above treatment, spiro-(9H-fluorene-9,3'-succinimide) and spiro-(2-fluoro-9H-fluorene-9,3'-succinimide).

Similarly, other tricycliccarboxylic acid esters known in the art are derived from the fluorene derivatives and heterotricyclic analogs of fluorene and derivatives, as are represented in but not limited to those examples cited in Table A and in the following example preparations can be utilized to prepare spiro-tricyclic-succinimides according to this general scheme:

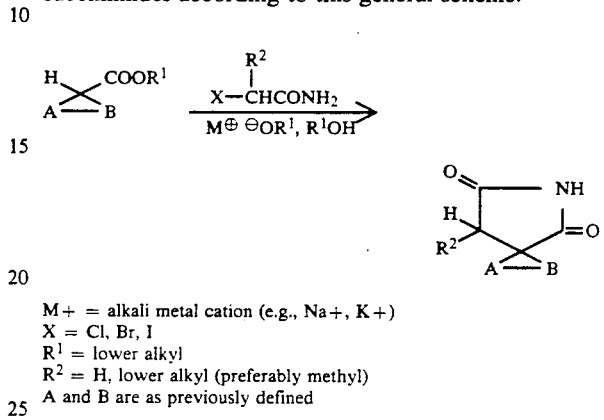

M+ = alkali metal cation (e.g., Na+, K+)
X = Cl, Br, I
$R^1$ = lower alkyl
$R^2$ = H, lower alkyl (preferably methyl)
A and B are as previously defined

METHOD V—HALOGENATION AND DERIVATIZATION OF FLUORENE, FLUORENONE AND THEIR INDENO-HETEROCYCLE ANALOGS AND DERIVATIVES

Halogenation of fluorene and fluorenone and related indeno heterocycle analogs such as 4-azafluorene or 4-azafluorenone and as exampled in Table A where Q is dihydrogen and oxygen can be accomplished by methods known and practiced in the art (e.g., Eckert and Langecker, *J. Prakt. Chem.*, 118, 263 (1928); Courot, *Ann. Chem.*, 14, 5 (1930); Bell and Mulholland, *J. Chem. Soc.*, 2020 (1949); Johnson and Klassen, *J. Chem. Soc.*, 988 (1962)). In general, chlorination of fluorenone and fluorene derivatives and related heterocyclic indeno analogs is accomplished by dissolving the substrate in glacial acetic acid containing anhydrous ferric chloride (10-20% by weight of substrate) and chlorine gas or chlorine dissolved in glacial acetic acid (1.2 to 3.0 molar equiv.) is added. The reaction is stirred at a selected temperature for several hours and allowed to cool; the crude product is isolated and solvent recrystallized to yield the chlorinated derivative.

The structure-reactivity of tricyclic azines, nitrogen analogs of fluorenone and fluorene, to electrophillic halogenation has been characterized by Mlochowski and Szulc, *J. Prakt. Chem.*, 322 (1980) 971.

Fluorination of selected derivatives of fluorene (and fluorenone) and indeno heterocyclic analogs involves a multistepped process wherein the substrate is first nitrated (Kretor and Litvinov, *Zh. Obsch. Khim.*, 31, 2585 (1961); *Org. Syntheses, Coll.* Vol. II, 447 (1943); *Org. Syntheses, Coll.* Vol. V, 30 (1973)). The resulting nitro derivative is reduced via Raney nickel and hydrazine, zinc dust and calcium chloride, iron filings and concentrated hydrochloride acid, palladium on carbon with hydrazine and other methods known to the art (*Org. Syntheses Coll.* Vol. II, 447 (1943); *Org. Syntheses Coll.* Vol. V, 30 (1973); Fletcher and Namkung, *J. Org. Chem.*, 23, 680 (1958)). The resulting aromatic amine(s): (a) is subjected to the Schiemann reaction according to the method of Fletcher and Namkung, *Chem. and Ind.*, 1961, 179, wherein the ammonium fluoroborate salt, prepared in the presence of tetrahydrofuran is first diazotized and then decomposed in hot xylene to yield the corresponding fluoro derivative. Oxidation of the fluoro derivative, e.g., 2-fluoro-9H-flourene, according to Sprinzak, *J. Amer. Chem. Soc.*, 80, 5449 (1958) or by other oxidation procedures known and practiced in the art, yields the ketone, e.g., 2-fluoro-9H-fluoren-9-one. In a general and novel process cited in U.S. Pat. Nos. 4,438,272 and 4,436,745, the fluorinated ketone is converted into the corresponding alkylsulfide, alkysulfoxide and/or alkylsulfone. An alkaline metal alkysulfide nucleophile (e.g., sodium methylthiolate in DMF) displaces fluoride to yield the corresponding alkylsulfide derivative, e.g., 2-methyl-thiol-9H-fluoren-9-one. The resulting alkylsulfide derivative can be oxidized by known procedures (e.g., sodium metaperiodate or hydrogen peroxide) to the corresponding sulfoxide and/or sulfone; (b) as hydrogen halide salt(s) is diazotized by sodium nitrate. Replacement of the diazonium group(s) in these aromatic derivatives by a halo or cyano group(s) (e.g., via KNC) salts (Sandmeyer), copper powder (Gatterman) or cupric salts (Korner-Contardi). See *Organic Synthesis* Vol. I, p. 170 (1932); E. Pfeil, *Angew. Chem.*, 65, 155 (1953); Y. Nakatani, *Tetrahedron Lett.*, 1970, 4455. As is known in the art, the resulting cyano derivatives can be hydrolyzed into carboxylic acids; alcoholyzed to carboalkoxy esters, e.g., carboethoxy esters; hydrolyzed to carboxamide; reduced to methylamine, etc., as is well known and practiced in the art. Other aromatic derivatizations can similarly be made by those skilled in the art. According to a general process of Teulin et al., *J. Med. Chem.*, 21 (1978) 901, tricyclic indeno derivatives with the general formula:

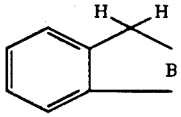

(where B is a previously defined) are derivatized to the corresponding arylisopropanoic and arylacetic acids. The process involves the following synthetic steps:

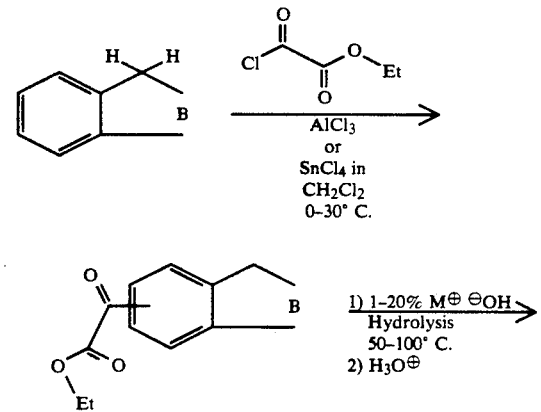

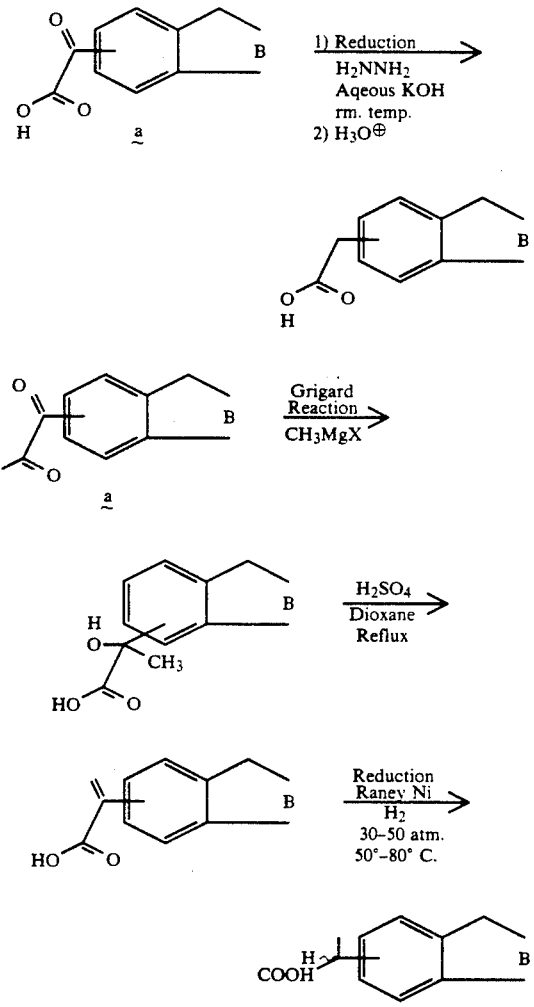

$M^{\oplus} = Na^{\oplus}, K^{\oplus}$
$X = Cl, Br, I$

In accordance with Method VII the aforementioned indeno derivatives can be oxidized to the corresponding ketones which are starting material substrates for spirohydantoin derivatization in accordance with Method I.

A serial process involving several of the aformentioned processes can be employed to introduce for example a fluoro, and a chloro substituent into the same tricyclcic-aromatic substrate. Other fluorene and fluorenone derivatives and indeno heterocyclic analog derivatives can be prepared in accordance with common synthetic procedures known and practiced in the art.

Finally, tricyclic aromatic azine derivative such as 5H-indeno[1,2b] pyridine-5-one or 5H-indeno[1,2-b]pyridine, can be pyridine N-oxidized to yield the corresponding pyridine N-oxide derivative. Such an N-oxide is employed to prepare the corresponding spiro-hydantoin derivative according to Method I or spiro-oxazolidinedione and spiro-succinimide according to Methods III and IV respectively. For example,

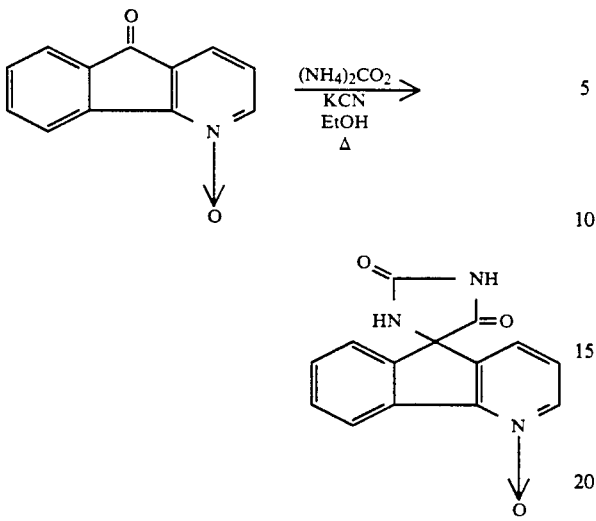

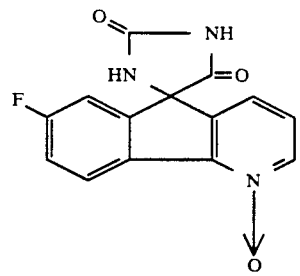

METHOD VI

The novel spiro-tricyclic-imidazolidinediones, -thiazolidinediones, -oxazolidinediones and -succinimides may be further derivatized according to the following.

Nitrated fluorenone will not easily derivatize to form the corresponding spiro-hydantoin.

The preferred method of preparation of spiro-hydantoin aromatic nitro derivatives is via direct nitration (e.g., via nitric acid and 60% sulfuric acid) of the spirocyclic derivatives, especially spiro-hydantoin (see Example XI). After nitration of the selected spiro-tricyclic-imidazolidinediones, -thiazolidinediones, -oxazolidinediones and succinimides by methods well known and practiced in the art, the corresponding aromatic nitro group(s) of corresponding spiro-tricyclic derivative(s) of the present invention can be reduced to the corresponding amine derivative(s). Aromatic nitro group(s) reduction to the aromatic amime(s) can be accomplished by a number of methods including reduction by hydrazine hydrate and Raney Nickel (see Fletcher and Namkung, J. Org. Chem., 23, 680 (1958). The resulting amine(s) as hydrogen halide salt(s) is diazotized by sodium nitrite. Replacement of the diazonium group(s) in these aromatic derivatives by a halo or cyano group(s) (e.g., via KCN) salts (Sandmeyer), copper powder (Gatterman) or cupric salts (Korner-Contardi). See Organic Synthesis Vol. I. p. 170 (1932); E. Pfeil, Angew. Chem., 65, 155 (1953); Y. Nakatani, Tetrahedron Lett., 1970, 4455. As is known in the art, the resulting cyano derivatives can be hydrolyzed into carboxylic acids; alcoholyzed to carboalkoxy esters, e.g., carboethoxy esters; hydrolyzed to carboxamide; reduced to methylamine, etc., as is well known and practiced in the art. Other aromatic derivatizations can similarly be made by those skilled in the art.

Spiro-tricyclic azine derivative, such as spiro-(7-fluoro-5H-indeno [1,2-b]pyridine-5,4'-imidazolidine)-2',5'-dione, is oxidized to the corresponding N-oxide derivative according to the general procedure of Mosher et al., Org. Syn., 33 (1953) 79 wherein peracetic acid is employed as the oxidizer. Such an N-oxide is active as aldose reductase inhibitor. For example,

METHOD VII

Heterocyclic analogues of fluorene and fluorene derivatives such as 1-azafluorene and 2-fluoroflourene can be transformed into corresponding ketones (e.g., 1-azafluorenone or 2-fluorofluorenone) via a number of oxidation procedures which are well known to those skilled in the art. Some relevant representative methods include:

a) Oxidation by oxygen under basic conditions according to a general procedure of U. Sprinzak, J. Amer. Chem. Soc., 80 (1958) 5449.

b) Oxidation by permanganate in which the flourene derivative is oxidized by potassium permanganate in acetone, e.g., see Urbina, Synthetic Communications 9 (1979), 245.

c) Oxidation by selenium dioxide in a sealed vessel at 200°-250° C. when common oxidation procedures such as chromuim trioxide in acetic acid are ineffective. See Arcus and Barnett, J. Chem. Soc. (1960) 2098.

METHOD VIII

Tricyclic ketones of the present invention may be reduced to the corresponding methylene reduction product by the Wolff-Kishner Reduction or by the Huang-Minlon modified Wolff-Kishner Reduction (see also MacDowell and Jefferies, J. Org. Chem., 35, 871 (1970)). Alternatively, these ketones may be reduced by lithium aluminum hydride in the presence of aluminum chloride (see Rault, Lancelot and Effi, Heterocycles 20, 477 (1983)) or by other reduction methods known to those skilled in the art.

METHOD OF TREATMENT IX

The spiro-tricyclic-thiazolidinedione, -imidazolidinedione, -oxazolidinedione and -succinimide compounds of the present invention are weak acids. In addition, several examples, as cited in Example XIX, are carboxylic acid derivatives and/or aromatic azines (i.e., contain a basic nitrogen(s) in the aromatic tricycle) and/or contain an alkylamine substituent. Therefore, these compounds are ameanble to preparation as base salts and in some cases, where basic amines are present, acid salts. Several examples contain both an acidic spiro functionality and carboxylic acid functionality. These cases can be prepared as mono- or di-basic salts.

The chemical bases which are used as reagents to prepare the aforementioned pharmaceutically acceptable base salts are those which form nontoxic (pharmaceutically acceptable) salts with the various herein described acidic spiro-imidazolidinedione, -thiazolidinedione, -oxazolidinedione and -succinimdie derivatives such as spiro-(7-fluoro-5-H-indeno[1,2-b] pyridine-5,4'-imidazolidine)-2',5'-dione, for example. Similarly, herein described carboxylic acid containing derivatives, such as spiro-(2-carboxy-9H-fluoren-9,5'-thiazolidine)-2',4'-dione, can be prepared as nontoxic salts. These nontoxic base salts are of a nature not to be considered clinically toxic over a wide therapeutic dose range. Examples of such cations include those of sodium, potassium, calcium, magnesium, etc. These pharmacologically acceptable nontoxic salts can be prepared by treating the aforementioned acidic specie, e.g., spirothiazolidinedione, with aqueous metallic hydroxide solution, and then evaporating the resulting solution, preferably at reduced pressure, to dryness. Alternatively, where indicated, the base salts can be prepared by mixing a lower alkanolic solution (e.g., ethanol) of the acidic compound with a desired alkali metal alkoxide (e.g., sodium ethoxide) in a lower alkanolic solution, and evaporating the solution to dryness in the same manner as before. In any case stoichiometric quantities of reagents must be employed in order to ensure completeness of reaction and maximum production of yields with respect to the final base salt product.

Acid salts of spiro-tricyclic azine derivatives, e.g., spiro-(7-fluoro-5H-indeno[1,2-b]pyridine-5,5'-thiazolidine)-2',4'-dione, can be prepared with nontoxic pharmacologically acceptable acids, e.g., hydrochloric acid and sulfuric acid. Examples of such anions of said acid salts include those of hydrogensulfate, sulfate, chloride, etc. These pharmacologically acceptable nontoxic acid salts can be prepared by treating the aforementioned basic specie, e.g., spiro-azafluorene derivative, with an acidic aqueous solution of the desired acid. After the basic species is solubilized in the acid, the solution is evaporated to dryness, preferably with reduced pressure. In this case, stoichiometric quantities of acid are preferred. Alternatively, in some cases the acid salt may be precipitated or recrystallized from strong acid solution (e.g., 5% hydrochloric acid). The salt then is collected by filtration and dried.

As previously indicated, the spiro-tricyclic-thiazolidinedione, -imidazolidinedione, -oxazolidinedione and -succinimide compounds of this invention are all readily adapted to therapeutic use as aldose reductase inhibitors for the control of chronic diabetic complications, in view of their ability to reduce lens sorbitol levels in diabetic subjects to a statistically significant degree. The herein described compounds of this invention can be administered by either the oral or parenteral routes of administration. In general, these compounds are ordinarily administered in dosages ranging from about 0.1 mg to about 10 mg/kg of body weight per day, although variations will necessarily occur depending upon the weight and condition of the subject being treated and the particular route of administration chosen; the preferred range is 0.5 to 4.0 mg/kg. Oral administration is preferred.

While matters of administration are left to the routine discretion of the clinician, long term, prophylactic administration of the compounds of the present invention is generally indicated on diagnosis of diabetes mellitus and/or neuropathy and/or retinopathy and/or vasculopathy and/or cataract and/or impaired wound healing and/or nephropathy and/or hyperglyceamia.

In connection with the use of the spiro-tricycle compounds of this invention for the treatment of diabetic subjects, it is to be noted that these compounds may be administered either alone or in combination with pharmaceutically acceptable carriers by either of the routes previously indicated, and that such administration can be carried out in both single and multiple dosages. More particularly, the compounds of this invention can be administered in a wide variety of different dosage forms, i.e., they may be combined with various pharmaceutically acceptable inert carriers in the form of tablets, capsules, lozenges, troches, hard candies, powders, sprays, aqueous suspensions, injectable solutions, elixirs, syrups, and the like. Such carriers include solid diluents of fillers, sterile aqueous media and various nontoxic organic solvent, etc. Moreover, such oral pharmaceutical formulations may be suitably sweetened and/or flavored by means of various agents of the type commonly employed for just such purposes. In general, the therapeutically useful compounds of this invention are present in such dosage forms at concentration levels ranging from about 0.5% to about 90% by weight of the total composition i.e., in amounts which are sufficient to provide the desired unit dosage.

For purposes of oral administration, tablets containing various excipients such as sodium citrate, calcium carbonate and calcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include lactose or milk sugar as well as high molecular weight polyethylene glycols. When aqueous suspensions and/or elixirs are desired for oral administration, the essential active ingredient therein may be combined with various sweetening or flavoring agents, coloring matter of dyes, and if so desired, emulsifying and/or suspending agents as well, together with such diluents as water, ethanol, propylene glycol, glycerin and various like combinations thereof.

For purposes of parenteral administration, solutions of these particular spiro-tricycles in sesame or peanut oil or in aqueous propylene glycol may be employed, as well as sterile aqueous solutions of the corresponding water-soluble, alkali metal or alkaline-earth metal or acid salts previously enumerated. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal injection purposes. In this connection, the sterile aqueous media employed are all readily obtainable by standard techniques well-known to those skilled in the art. Additionally, it also is possible to administer the aforesaid spiro-tricycle compounds topically via an appropriate ophthalmic solution suitable for the present purposes at hand, which can then be given dropwise to the eye.

The activity of the compounds of the present invention, as agents for the control of chronic diabetic complications, is determined by their ability to successfully pass one or more of the following standard biological and/or pharmacological tests, viz., (1) measuring their ability to inhibit the enzyme activity of isolated human aldose reductase; (2) measuring their ability to reduce or inhibit enzyme activity of rat lens aldose reductase in vitro; (3) measuring their ability to preserve motor nerve conduction velocity in chronic streptozotocin-induced diabetic rats; (4) and measuring their ability to delay cataract formation and reduce the severity of lens opacities in chronic galactosemic rats; (5) measuring with electron microscopy their ability to prevent basement membrane thickening in the kidney glomerulus and/or retina capillaries in chronic streptozotocin-induced diabetic rats (6) measuring their ability to maintain rat lenses in 30 mM xylose culture for 18 h.

Typical preparative methods and synthetic design for substituted analogs of the tricycles of Table A and Formulas II and III are provided for instruction.

x, y and z are as previously defined. Where Q=H$_2$ or O

TABLE A

| Substrates and Derivatives | Method of Preparation |
|---|---|
|  | A |
|  | B |
|  | C |
|  | D |
|  | E |
|  | E |
|  | E |
|  | E |

TABLE A-continued

| Substrates and Derivatives | Method of Preparation |
|---|---|
|  | E |
|  | F |
|  | G |
|  | H |
|  | I |
|  | J |
|  | J |
|  | J |
|  | J |
|  | J |

TABLE A-continued

| Substrates and Derivatives | Method of Preparation |
|---|---|
| 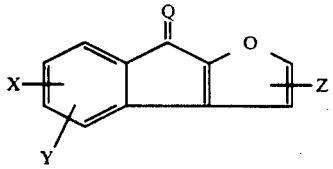 | K |
| 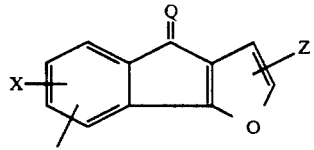 | L |
| 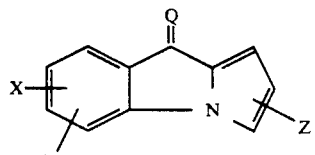 | M |
| 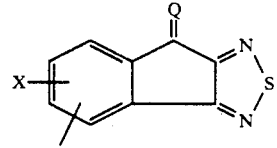 | N |
| 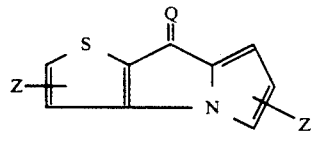 | O |
| 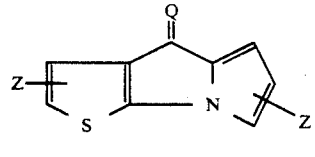 | O |
| 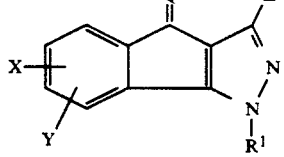 | P |
| 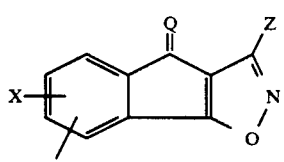 | P |
| 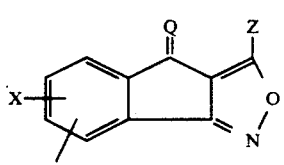 | P |
| 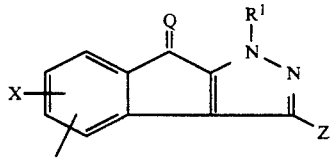 | P |
| 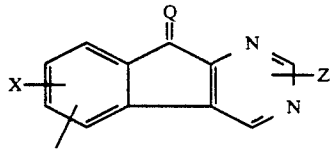 | P |
| 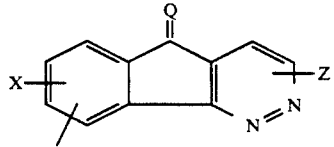 | P |
| 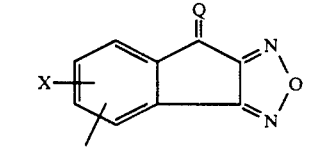 | Q |

PREPARATION A

Synthesis substrates 8H-indeno[2,1-b]thiophen-8-one and 8H-indeno [2,1-b]thiophene and their derivatives are prepared in accordance with the following by a general method of Venin, Brault and Kerfanto, C. R. Acad. Sc. Paris, 266 (c), 1650 (1968), various substituted phenylglyoxals are prepared in a three step process involving: gem dibromination of the substituted acetophenone (e.g., p-fluoroacetophenone) to the corresponding α, α-dibromoacetophenone; nucleophillic displacement of the gem bromides to yield the corresponding animal; aqueous acid (e.g., dilute HCl) hydrolysis to yield the substituted phenylgloxal, e.g., p-fluorophenylglyoxal. By such a process the following substituted phenylglyoxals are prepared:

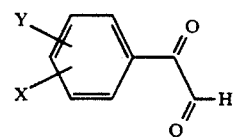

X and Y=H, halogen, lower alkyl, lower cycloalkyl, COOH, C≡N, —O—R, —S—R, —S(O)R, —SO$_2$R R=Lower alkyl from commercially available substituted acetophenones (e.g., o-, p-or m- fluoro- chloro- or bromo - acetophenone may be purchased from Aldrich Chemical, Inc.). Other substituted acetophenones are prepared by methods well known to those skilled in the art. Phenglyoxal (Aldrich Chemical, Inc.) is commercially available. Such prepared substituted phenylglyoxals (e.g., 4'-fluorophenylglyoxal) are utilized to synthesize corresponding substituted 8H-indeno[2,1-b]thiophen-8-one and 8H-indeno[2,1-b]thiophene substrates which are derivatized by Methods I-IV. The synthesis of substituted 8H-indeno[2,1-b]thiophen-8-one involves the Hinsberg Stobbe type condensation (Wolf and Folkers, *Org. Reactions*, 6, 410 (1951)) between the substituted phenylglyoxal, e.g., 4'-fluorophenylglyoxal, and diethylthiodiglycolate using sodium ethoxide. After saponification, the isolated substituted 3-phenyl-2,5-thiophenedicarboxylic acid, e.g., 3-(4'-fluorophenyl)-2,5-thiophenedicarboxylic acid is treated with thionyl chloride to form the diacylchloride which is intramolecularly cyclized by a Friedel-Crafts reaction catalyzed by aluminum chloride or stannic chloride to give the correspondingly substituted 8-oxo-8H-indeno-[2,1-b]thiophen-2-carboxylic acid, e.g., 6-fluoro-8-oxo-8H-indeno-[2,1-b]thiophen-2-carboxylic acid, (A-1), which can be converted into a hydantoin derivative according to Method I. Decarboxylation of (A-1) by copper powder in anhydrous quinoline yields the corresponding substituted 8H-indeno-[2,1-b]thiophen-8-one (A-2) which is converted (in accordance with Method I) into a hydantoin derivative such as spiro(6-fluoro-8H-indeno[2,1-b]thiophen-8,4'-imidazolidine)-2',5'-dione. See Example XIV for the preparation of spiro-(8H-indeno[2,1-b]thiophen-8,4'-imidazolidine)-2',5'-dione. The Wolff-Kishner reduction (Method VIII) of (A-1) or (A-2), preferably (A-1), yields the corresponding substituted 8H-indeno[2,1-b]thiophene, e.g., 6-fluoro-8H-indeno-[2,1-b]thiophene. In the alkaline hydrazine (in excess) reduction of the ketoacid (A-l), both keto reduction and decarboxylation may occur. Product isolation is best accomplished by fractional distillation, but may involve other separation methods as are known in the art. Further derivatization may be accomplished according to Method V. The resulting substituted 8H-indeno[2,1-b]thiophene is metalated by n-butyllithium and carbonated in the methylene bridge to yield the corresponding 8-carboxylic acid which, after esterification, at reflux with a lower alkyl alcohol such as methanol under acid catalyzed conditions such as concentrated hydrochloric acid yields the corresponding substituted or unsubstituted 8H-indeno [2,1-b]thiophen-8-carboxylic acid alkyl ester, e.g., 6-fluoro-8H-indeno[2,1-b]thiophen-8-carboxylic acid methyl ester. The ester is utilized according to Methods II, III and IV to yield the corresponding spiro-thiazolidinedione, spiro-oxazolidine-dione and spiro-succinimide such as spiro-(6-fluoro-8H-indeno[2,1-b]thiophen-8,5'-thiazolidine)-2',4'-dione, spiro-(6-fluoro-8H-indeno-8,5'-oxazolidine)-2,4'-dione and spiro-(6-fluoro-8H-indeno[2,1-b]thiophen-8,3'-succinimide) respectively.

PREPARATION B

Synthesis substrates 4H-indeno[1,2-b]thiophen-4-one and 4H-indeno [1,2-b]thiophene can be prepared according to a general process of MacDowell and Jefferies, *J. Org. Chem.*, 35, 871 (1970). In this process the 4-one substrate is prepared by the Ullmann coupling of ortho-iodo or ortho-bromo, di, tri and tetrasubstituted benzoic acid lower alkyl esters, such as 3-fluoro-2-iodobenzoic acid ethyl or methyl ester (Chem. Abst.; 27:1339/G) or 2-bromo-4-fluoro-benzoic acid methyl ester (Chem. Abst. 99(1):5630j) or 2-bromo-5-chlorobenzoic acid methyl ester (*J. Med. Chem.*, 13, 567-8 (1970) with 2-iodo or 2-bromothiophene (Aldrich Chemical, Inc.). Saponification of the coupled product will yield the corresponding substituted 2-(2'-thienyl) benzoic acid (e.g., 5-chloro-2-(2'-thienyl)benzoic acid from 2-bromo-5-chloro-benzoic acid methyl ester). Cyclization of the acid is performed via the aroyl halide using stannic chloride or aluminum chloride to yield to substituted 4H -indeno[1,2-b]thiophen-4-one (B-1) (e.g., 6-chloro-4H-indeno[1,2-b]thiophen-4-one). This 4-one derivative is converted (in accordance with Method I) into a hydantoin derivative such as spiro-(6-chloro-4H-indeno[1,2-b]thiophen-4,4'-imidazolidine)-2',5'-dione. See Example XIII for the preparation of spiro-(4H-indeno[1,2-b]thiophen-4,4'-imidazolidine)-2',5'-dione. The Wolff-Kishner reduction (Method VIII) of (B-1) yields the corresponding 4H-indeno[1,2-b]thiophene. Product isolation is best accomplished by fractional distillation, but may involve other separation methods as are known in the art. The resulting substituted or unsubstituted 4H-indeno[1,2-b]thiophene (which may be further derivatized according to Method V) is metalated by n-butyllithium and carbonated in the methylene bridge to yield the corresponding 4-carboxylic acid which after esterification at reflux with a lower alkyl alcohol such as methanol under acid catalyzed conditions such as concentrated hydrochloric acid yields the corresponding substituted or unsubstituted 4H-indeno[1,2-b]thiophen-4-carboxylic acid lower alkyl ester, e.g., 6-chloro-4H-indeno[1,2-b]thiophen-4-carboxylic acid methyl ester. The ester is utilized according to Methods II, III, and IV to yield the corresponding spirothiazolidinedione, spiro-oxazolidinedione and spiro-succinimide such as spiro-(6-chloro-4H-indeno[1,2-b]thiophen-4,5'-thiazolidine]-2',4'-dione, spiro-(6-chloro-4H-indeno[1,2-b]thiophen-4,5'-oxazolidine)-2',4'-dione and spiro-(6-chloro-4H-indeno[1,2-b]thiophen-4,3'-succinimide) respectively. The resulting spiro-derivatives may be further derivatized according to Method VI.

PREPARATION C

Synthesis substrates 4H-indeno[1,2-c]thiophen-4-one and 4H-indeno [1,2-c]thiophene and their derivatives are prepared in accordance with MacDowell and Jefferies, *J. Org. Chem.*, 35, 871 (1970). Wherein treatment of 4-bromo-3-thienyllithium with a commonly available lower alkyl substituted cyclohexanone or cyclohexanone, such as 4-methylcyclohexanone, at −65° to −75° C. yields the corresponding cyclohexanol derivative which is dehydrated with para-toluenesulfonic acid in refluxing benzene or toluene to yield a cyclohexylthiophene product such as 3-bromo-4-(4-methyl-1'-cyclohexenyl)thiophene. Dehydrogenation with tetrachlorobenzoquinone in refluxing xylene for 8-24 hours yields the corresponding 3-bromo-4-phenylthiophene, e.g., 3-bromo-4-(4'-methylphenyl)thiophene. After purification by sublimation and/or chromatography over alumina, the bromide is subjected to halogen-metal exchange at −65° to −75° C. with n-butyllithium in ether, followed by carbonation with carbon dioxide. The isolated 3-phenyl-thiophene-4-carboxylic acid derivative, e.g., 3-(4'-methylphenyl)thiophene-4-carboxylic acid, is converted with thionyl chloride to the acid halide. Ring closure to the ketone via heating the aroyl chloride and aluminum chloride in carbon disulfide for 18-36 hours yields the corresponding ketone, such as 6-methyl-8H-indeno[1,2-c]thiophen-8-one. This 8-one derivative, which may be further derivatized according to Method V, is converted (in accordance with Method I) into a hydantoin derivative. Wolff-Kishner reduction (Method VIII) of the 8-one derivative (and optional derivatization according to Method V) and spiro-derivatization in accordance with Methods II, III and IV yields the corresponding spiro-thiazolidinedione, spiro-oxazolidinedione and spiro-succinimide derivatives respectively. These spiro-derivatives may be further derivatized according to Method VI.

PREPARATION D

Synthesis substrate 7H-cyclopenta[1,2-b:4,3-b']dithiophene is prepared according to the method of Wynberg and Kraak, *J. Org. Chem.*, 29, 2455 (1964). The corresponding spiro-thiazolidinedione, spiro-oxazolidinedione and spiro-succinimide derivatives are prepared according to Methods II-IV respectively. The 7-one derivative is prepared from the cyclopentadithiophene in accordance with the oxidation procedures cited in Method VII. The ketone, 7H-cyclopenta [1,2-b:4,3-b]dithiophen-7-one is converted into the spiro-hydantoin derivative in accordance with Method I.

PREPARATION E

Synthesis substrates 4H-cyclopenta[2,1-b:3,4-b']dithiophene,7H-cyclopenta [1,2-b:3,4-b']dithiophene,7H-cyclopenta[1,2-c:3,4-c']dithiophene, 7H-cyclopenta[1,2-b:3,4-c']dithiophene and 7H-cyclopenta[2,1-b:3,4-c']dithiophene are prepared according to the procedure of Wiersema and Wynberg, *Tetrahedron*, 24, 3381 (1968). From these, the corresponding spiro-thiazolidinedione, spiro-oxazolidinedione and spiro-succinimide derivatives are prepared according to Methods II-IV respectively. The corresponding 4H-cyclopenta[2,1-b:3,4-b']dithiophen-4-one, 7H-cyclopenta[1,2-b:3,4-b']dithiophen-7-one, 7H-cyclopenta[1,2-c:3,4-c']dithiophen-7-one, 7H-cyclopenta[1,2-b:3,4-c']dithiophen-7-one and 7H-cyclopenta[2,1-b:3,4-c']dithiophen-7-one are prepared in accordance with the oxidation procedures cited in Method VII. The resulting ketones are spiro-hydantoin derivatized in accordance with Method I.

PREPARATION F

Synthesis substrates 5H-indeno[1,2-b]pyridin-5-one and 5H-indeno[1,2-b]pyridine (as 4-azafluorene from Aldrich Chemical, Inc.) and their derivatives are prepared according to a general procedure of Parcell and Hauck, *J. Org. Chem.*, 21, 3468 (1963), wherein the piperidineenamine of 2,3-dihydro-1H-inden-1-one (available from Aldrich Chemical, Inc.), -4,-5 or -6- chloro or fluoro-2,3-dihydro-1H-inden-1-one (Olivier and Marechal, *Bull. Soc. Chim.* France, (1973), 3092), 6-chloro-5-cyclopentylmethyl-2,3-dihydro-1H-inden-1-one (Biere et al., *Eur. J. Med.*, 18, 255 (1983)), 5,6-dimethoxy-2,3-dihydro-1H-inden-1-one (Koo, *J. Amer. Chem. Soc.*, 75, 1891 (1953)), 5 or 6-methoxy-2,3-dihydro-1H-inden-1-one (available from Aldrich Chemical, Inc.) or other substituted 1-indanones is formed from piperidine in the presence of p-toluensulfonic acid catalyst according to the procedure of Heyl and Herr, *J. Amer. Chem. Soc.*, 75, 1918 (1953). The resulting piperidineenamine is reacted with 3-bromopropylamine hydrobromide or hydrochloride (available from Aldrich Chemical, Inc.) to yield an imine product.

The process typically involves the addition of 1.1 molar equivalents of the enamine to 1 molar equivalent of bromopropylamine hydrobromide in dimethylformamide at elevated temperature until the exothermic reaction is initiated wherein the temperature is kept at 90°-120° C. for several hours. The product is isolated by a combination of acidification and ether washing followed by basification and ether extractions. Evaporation yields the tetrahydroimine product such as:

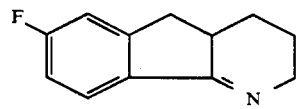

The tetrahydroimine product is aromatized in xylene and nitrobenzene and 10% palladium on charcoal according to Parcell and Hauch, ibid. The resulting product, e.g., 7-fluoro-5H-indeno[1,2-b]pyridine (which may be further derivatized according to Method V) is derivatized according to Methods II to IV to yield the corresponding spiro-derivatives such as spiro-(7-fluoro-5H-indeno[1,2-b]pyridin-5,5-thiazolidine)-2',4'-dione;- spiro-(7-fluoro-5H-inden[1,2-b]pyridin-5,5'-(oxazolidine)-2',4'-dione and spiro-(7-fluoro-5H-indeno[1,2-b]pyridin-5,3'-suiccinimide. Oxidation (Method VII) of 5H-indeno[1,2-b]pyridine or its derivatives according to the method of Sprinzak, *J. Amer. Chem. Soc.*, 80, 5449 (1958) yields the corresponding 5-one or ketone derivative, which may be further derivatized according to Method V. When reacted in accordance with Method I, the ketone will yield a spiro-hydantoin derivative such as spiro-(7-fluoro-5H-indeno[1,2-b]pyridin-5,4'-imidazolidine)-2',5'-dione. Any of the aforementioned spiro derivatives may be further derivatized, e.g., nitrated, in accordance with Method VI. See Examples XVIII, XI and XII.

PREPARATION G

Synthesis substrates 5H-indeno[1,2-c]pyridin-5-one and 5H-indeno[1,2-c]pyridine and their derivatives may be prepared in accordance with the following. 3-Azafluorenone (5H-indeno[1,2-c]pyridine-5-one) is prepared according to the method of Mayor and Wentrup, *J. Amer. Chem. Soc.*, 97, 7467 (1975). The ketone can be derivatized in accordance with Method V. The ketone, e.g., 5H-indeno[1,2-c]pyridin-5-one, is hydantoin derivatized according to Method I. A Wolff-Kishner reduction (Method VIII) of this 3-azafluorenone can be accomplished according to Kloc et al., *Heterocycles* 9, 849 (1978) to yield the corresponding 5H-indeno[1,2-c]pyridine which is derivatized in accordance with Methods II-IV to yield to the corresponding spiro-thiazolidinedione, spiro-oxazolidinedione and spiro-succinimide respectively. The aforementioned spiro derivatives may be further derivatized according to Method VI.

PREPARATION H

Synthesis substrates 9H-indeno[2,1-c]pyridin-9-one and 9H-indeno[2,1-c]pyridine are prepared according to the method of Mayor and Wentrup, *J. Amer. Chem. Soc.*, 97, 7467 (1975). Further derivatization may be accomplished in accordance with Method V. The resulting indenopyridine or 2-azafluorene product is further derivatized according to Methods II-IV to yield the spiro-thiazolidinedione, spiro-oxazolidinedione and spiro-succinimide derivatives. Oxidation of the indenopyridine to the corresponding ketone is accomplished by sodium dichromate or other oxidation procedures as cited in Table A. The resulting ketone may be derivatized in accordance with Method V. The selected 2-azafluoreneone derivative is derivatized to yield the spiro-hydantoin. See Example XVI for the preparation of spiro-(9H-indeno[2,1-c]pyridine-9,4'-imidazolidine)-2',5'-dione. The aforementioned spiro-derivatives may be further derivatized according to Method VI.

Furthermore, in example, 7-amino-2-azafluorene or 7-amino-9H-indeno[2,1-c]pyridine can be prepared according to the method of Perin-Roussel and Jacquignon, *C. R. Acad. Sc. Paris*, 278, 279 (1974). This amino product, in accordance with Method V, can be transformed via the Schiemann reaction into 7-fluoro-9H-indeno[2,1-c]pyridine. This substrate, as above, can be transformed by Methods I–IV into spiro-(7-fluoro 9H-indeno[2,1-c]pyridin-9,4'-imidazolidine)-2',5'-dione, spiro-(7-fluoro 9H-indeno[2,1-c]pyridin-9,5'-thiazolidinedione)-2',4'-dione, spiro-(7-fluoro 9H-indeno[2,1-c]pyridin-9,5'-oxazolidine)-2,4'-dione and spiro-(7-fluoro 9H-indeno[2,1-c]pyridin-9,3'-succinimide).

PREPARATION I

The ketone substrate, 9H-indeno[2,1-b]pyridin-9-one may be prepared by the method of Kloc, Michowski and Szulc, *J. prakt. chemie*, 319, 95q (1977). This ketone can be derivatized according to Method V. The substituted or unsubstituted ketone is then derivatized in accordance with Method I to yield the spiro-hydantoin which may be further modified according to Method VI.

The ketone, from the above, is reduced to a method cited in Method VIII or in general the Wolff-Kishner reduction to yield corresponding 9H-indeno[2,1-b]pyridine which is then derivatized in accordance with Methods II, III and IV to yield spiro-thiazolidinedione, spiro-succinimide.

Alternatively, 5H-indeno[2,1-b]pyridine-5-one (also called 1-azafluoren-9-one) and 5 to 8 position fluoro or chloro derivatives are prepared according to a general procedure of Urbina, *Synthetic Comm.*, 9, 245 (1979). Where to a substituted or unsubstituted 1-phenyl-2-propanone (e.g., 1-(4'-fluorophenyl)-2-propanone) is added acrylonitrile producing a corresponding 5-cyano-3-phenyl-2-pentanone, e.g., 5-cyano-3-(4'-fluorophenyl)-2-pentanone. The pentanone product is hydrogenated and cyclized to the corresponding 2-methyl-3-phenylpiperidine, e.g., 2-methyl-3-(4'-fluorophenyl)-piperidine. Aromatization of the 2-methyl-3-phenyl piperidine is carried out in vapor phase with catalyst K-16 (Prostakon, Mathew and Kurisher, *Khim-Geterotsikl. Socd.*, 876 (1970)) at 380° to 420° C. to yield the corresponding 2-methyl-3-phenylpyridine. Alternatively, aromatization can be achieved with Pd/C. Dehydrocyclization of the methyl-3-phenylpyridine at 500° to 550° C. over K-16 will produce the appropriate 1-azafluorene, e.g., 7-fluoro-1-azafluorene. The 9H-indeno[2,1-b]pyridine and its derivatives (e.g., 7-fluoro-9H-indeno[2,1-b]pyridine) are converted in accordance with Method II, III and IV into spiro-thiazolidinedione, spiro-oxazolidinedione and spiro-succinimide derivatives. The 9H-indeno[2,1-b]pyridine is oxidized according to general procedures cited in Method VII or potassium permanganate (Urbina, ibid). The resulting ketone, e.g., 7-fluoro-9H-indeno[2,1-b]pyridin-5-one, is derivatized in accordance with Method I to yield the spiro-hydantoin derivative, such as spiro-(7-fluoro-9H-indeno[2,1-b]pyridin-9,4'-imidazolidine)-2',5'-dione.

PREPARATION J

Synthetic substrates 5H-cyclopenta[2,1-b:4,3-b']dipyridin-5-one, 5H-cyclopenta[1,2-b:3,4-c']dipyridin-5-one, 5H-cyclopenta[1,2-b:4,3-b']dipyridin-5-one, 5H-cyclopenta[2,1-b:4,3-c']dipyridin-5-one, 5H-cyclopenta,,[1,2-b:3,4-c']dipyridin-5-one, 5H-cyclopenta-[1,2-b:4,3-b']dipyridin-5-one, 5H-cyclopenta[2,1-b:4,3-c']dipyridin-5-one, 5H-cyclopenta-[2,1-b:3,4-c']dipyridin-5-one, and 5H-cyclopenta-[2,1-b:3,4-b']dipyridin-5-one can be prepared according to the method of Kloc, Michowski and Szulc, *J. prakt. chemie*, 319, 95q (1977). These ketones in accordance with Method I are derivatized into the spiro-hydantoin products. Wolff-Kishner reduction or reduction according to Method VIII of the aforementioned ketones yields the corresponding diazafluorene substrates such as 5H-cyclopenta[2,1-b:4,3-b']dipyridine. These diazafluorene substrates are derivatized according to Methods II–IV to yield the corresponding spiro-thiazolidinedione, spiro-oxazolidinedione and spiro-succinimide derivatives.

PREPARATION K

Synthetic substrates 8H-indeno[2,1-b]furan-8-one and 8H-indeno[2,1-b]furan and their derivatives are prepared in accordance with the following. Substituted and unsubstituted 3-arylfuran-2-carboxylic acids are prepared according to a general procedure of Burgess, *J. Org. Chem.*, 21, 102 (1956), wherein, 4,5-dimethoxy-1-phenyl-2-butanone and related 2' to 4' substituted phenyl analogs (e.g., 4,4-dimethoxy-1-(4'-fluorophenyl)-2-butanone, prepared according to the general procedure of Royals and Brannoch, *J. Amer. Chem. Soc.*, 75, 2050 (1953)) are converted into 3-phenylfuran-2-carboxylic acid methyl ester (e.g., 3'-(4'-fluorophenyl-furan-2-carboxylic acid methyl ester) by the Darzens glycidic ester condensation (Darzens, *Compt. Rend.*, 139, 1214 (1904)). This rearrangement of the glycidic ester yields the furoic ester. The furoic ester can be hydrolyzed in alkaline methanolic solution to yield, for example, 3-(4'-fluorophenyl)-furan-2-carboxylic acid. The furoic acid product can be cyclized via the aroyl chloride in the presence of stannic chloride or aluminum chloride to yield the ketone, e.g., 6-fluoro-8H-indeno[2,1-b]furan-8-one. This ketone can be derivatized in accordance with Method V. Hydantoin derivatization (Method I) yields the spirohydantoin, e.g., spiro-(6-fluoro-8H-indeno[2,1-b]furan-8,4'-imidazolidine)-2',5'-dione. Reduction according to methods cited in Method VIII yields the corresponding 8H-indeno[2,1-b]furan derivative which can be derivatized in accordance with Methods II, III and IV into the corresponding spiro-thiazolidinedione, spiro-oxazolidinedione and spiro-succinimide. Furthermore, the spiro-derivatives may be further derivatized according to Method VI.

PREPARTION L

Synthetic substrates 4H-indeno[1,2-b]furan-4-one and 4H-indeno[1,2-b]furan and their substituted analogs are prepared from the corresponding substituted and unsubstituted 2-arylfuran-3-carboxylic acids which are prepared according to a general procedure of Johnson, *J. Chem. Soc.*, 1946, 895. The procedure involves the condensation of 1,2-dichlorodiethyl ether with aroylacetic esters, such as ethyl benzoylacetate (Aldrich Chemical, Inc.), in the presence of 10% ammonium hydroxide, yields a mixture of the 2-arylfuran-3-carboxylic ester and 2-arylpyrrole-3-carboxylic ester (which can be used to prepare the corresponding 4H-indeno[1,2-b]pyrrole-4-one) which are separated by fractionation. Saponification (10% KOH in 50% methanol) of the furan ester, acidification and isolation yields the corresponding 2-arylfuran-3-carboxylic acid. Treatment with phosphorus pentachloride followed by stannic chloride effects the Friedel-Crafts cyclization to the ketone. Alternatively, thionyl chloride may be employed to prepare the acyl chloride followed by aluminum trichloride or stannic chloride as the Friedel-Crafts catalyst in a solvent such as methylene chloride to yield the process is summarized by this example:

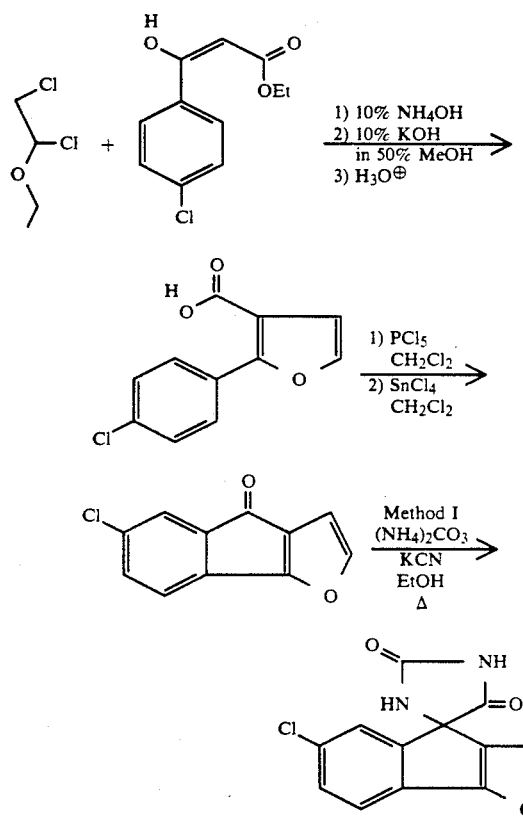

Then according to Method I, the spiro-hydantoin derivative is prepared, e.g., spiro-(6-chloro-4H-indeno[1,2-b]furan-4,4'-imidazolidine'2',5'-dione.

Analogous to earlier preparations, the ketone can be reduced according to Method VIII (Wolff-Kishner reduction) to yield the corresponding 4H-indeno[1,2-b]furan. This heterocycle can derivatized according to Method V. The derivatized or underivatized 4H-indeno[1,2-b]furan according to Method II, III and IV is derivatized to the corresponding spiro-thiazolidinedione, spiro-oxazolidinedione and spiro-succinimide respectively.

These spiro derivatives may be further derivatized in accordance with Method VI.

PREPARATION M

Synthesis substrates 9H-pyrrolol[1,2-a]indole and 9H-pyrrolol[1,2-a]indol-9-one and their derivatives are prepared in accordance with the general methods of Josey and Jenner, *J. Org. Chem.*, 27 (1962) 2466 and Mazzola et al., *J. Org. Chem.*, 32 (1967) 486. The process involves condensation of a substituted or unsubstituted methyl anthranilate (Aldrich Chemical, Inc.) with 2,5-dimethoxytetrahydrofuran (Aldrich Chemical, Inc.) in glacial acetic acid. Ester hydrolysis of the resulting 1-(2-methoxycarbonylphenyl)pyrrole with 10–15% potassium or sodium hydroxide in aqueous alcohol (e.g., 50% methanol) yields after acidification and subsequent work-up yields the corresponding 1-(2-carboxyphenyl)-pyrrole. This acid is then converted into the corresponding acyl chloride to facilitate a Friedel-Crafts cyclization to the ketone. The preferred method of preparing the acyl chloride is with phosphorus pentachloride followed with stannic chloride as the Friedel-Crafts catalyst to cyclize the acyl chloride to the desired ketone.

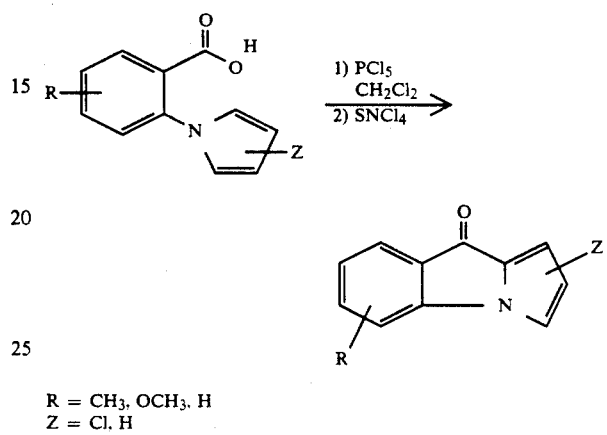

R = CH₃, OCH₃, H
Z = Cl, H

Wolf-Kishner reduction, see also Method VIII, via the semicarbazones of the ketone yields the corresponding 9H-pyrrolol[1,2-a]indole heterocycle.

The resulting ketone, such as 9H-pyrrolol[1,2-a]indole-9-one, is converted into the corresponding spiro-hydantoin according to Method I, see Example XV. The resulting spiro-hydantoin can be further derivatized in accordance with Method VI. Alternatively, the ketone may be derivatized according to Method V prior to spiro-hydantoin derivatization.

Similarly, 9H-pyrrolol[1,2-a]indole or its derivatives may be derivatized according to Method V. The derivatized or underivatized heterocycle then may be further derivatized according to Methods II, III or IV to yield the corresponding spiro-thiazolidinedione, spiro-oxazolidinedione or spiro-succinimide respectively. These spiro-derivatives in turn may be derivatized in accordance with Method VI.

PREPARATION N

Synthesis substrates 4H-indeno[2,3-c]-1,2,5-thiadiazol-4-one and 4H-indeno[2,3-c]-1,25-thiadiazole and their derivatives are prepared in accordance with the procedure of Mataka et al., *Synthesis*, 1979, 524 and Mataka et al., *J. Hetero. Chem.*, 17 (1980) 1681. The process involves reacting tetranitrogentetrasulfide with 1,3-dihydro-2H-indeno-2-one (Aldrich Chemical, Inc.) in toluene at reflux yields:

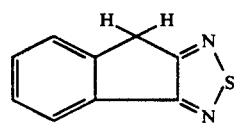

Alternatively, 5-fluoro-1,3-dihydro-2H-indeno-2-one (Flammang et al., *Eur. J. Med. Chem.*, 11 (1976) 83), 4-chloro-1,3-dihydro-2H-indeno-2-one (CA80:146166a) and 5-chloro-1,3-dihydro-2H-indeno-2-one (Olivier et al., *Bull. Soc. Chem. Fr.*, 11 (1973) 3096) can similarly be rated with tetranitrogentetrasulfide to yield the corresponding substituted indenothiadiazole heterocycles. These heterocycles may be further derivatized in accordance with Method V and according to Methods II, III and IV derivatized into the corresponding spiro-thiazolidinedione, spiro-oxazolidinedione and spiro-succinimides respectively. These spiro derivatives in turn may be further derivatized according to Method VI. Oxidation of the 4H-indeno[2,3-c]-1,2,5-thiadiazole in accordance with Method VII yields the ketone which may be derivatized in accordance with Method I to yield the corresponding spiro-hydantoin, e.g., spiro(4H-indeno[2,3-c']-1,2,5-thiadiazol-4,4'-imidazolidine)-2',5'-dione. This spiro hydantoin in turn may be derivatized further in accordance with Method VI.

PREPARATION O

The triheterocyclic substrates thieno[2,3-b]pyrrolizine and thieno[2,3-b]pyrrolizin-4-one; thieno[3,2-b]pyrrolizine and thieno[3,2-b]pyrrolizin-4-one are prepared exactly according to Rault et al., *Heterocycles*, 20 (1983) 477. The process involves the cyclization in boiling phosphoryl chloride of amide derivatives of 2-(1-pyrrolyl)-3-thienylcarboxylic acid and 3-(1-pyrrolyl)-2-thienylcarboxylic acid to yield thieno[2,3-b]pyrrolizin-4-one and thieno[3,2-b]pyrrolizin-4-one respectively. These ketones in accordance with Method I can be derivatized to the corresponding spiro-hydantoins: spiro-(thieno[3,2-b]pyrrolizin-4,4'-imidazolidine)-2',5'-dione and spiro-(thieno[3,2-b]pyrrolizin-4,4'-imidazolidine)-2',5'-dione. Both thieno[2,3-b]pyrrolizin-4-one and thieno[3,2-b]pyrrolizin-4-one can be reduced with 1.75 equivalents of lithium aluminum hydride in the presence of 3.5 equivalents aluminum chloride to yield the corresponding 4H-thieno-pyrrolizines quantitatively. The resulting thieno[2,3-b]pyrrolizine and thieno[3,2-b]pyrrolizine can be derivatived according to Methods II, III and IV into the corresponding spiro-thiazolidinediones, spiro-oxazolidinediones and spiro-succinimides, such as spiro-(thieno[3,2-b]pyrrolizin-4,5'-thiazolidine)-2',4'-dione, spiro-(thieno[2,3-b]pyrrolizin-4,5'-oxazolidine)-2',4'-dione and spiro-(thieno[3,2-b]pyrrolizin-4,3'-succinimide).

PREPARATION P

In an analogous manner to the preceding, the following starting materials may be derivatized in accordance with Methods I, II, III, IV, V, VII and VIII. Resulting spiro-derivative products may be further derivatized in agreement with Method VI.

a) 1- and 2-substituted -1H-indeno[1,2-c]pyrazol-4-ones

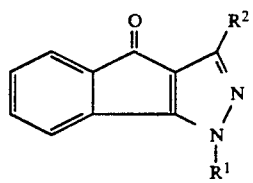

wherein $R^1$=H or lower alkyl and $R^2$=lower alkyl or lower cycloakyl, are prepared according to Lemke and Sawney, *J. Heterocyclic Chem.* 19 (1982) 1335 and Mosher and Soeder, *J. Heterocyclic Chem.*, 8 (1971) 855.

b) 3-alkyl-4H-indeno[1,2-c]isoxazol-4-ones

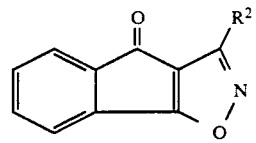

wherein $R^2$=lower alkyl (preferably methy), are prepared according to Lemke et al., *J. Heterocyclic Chem.*, 19 (1982) 363.

c) 3-alkyl-4H-indeno[1,2-c]isoxazol-4-ones

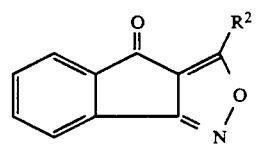

wherein $R^2$=lower alkyl (preferably methyl), are prepared according to Lemke and Martin, *J. Heterocyclic Chem.*, 19 (1982) 1105.

d) 3-methyl-1H-pyrazolo[3',4':3,4]cyclopenta[1,2-b]pyridin-4-one and 3-methyl-1H-pyrazolo[3',4':3,4]cyclopenta[2,1-c]pyridin-4-one

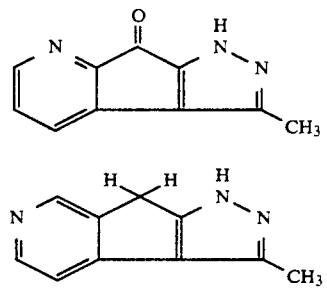

respectively are prepared according to Mosher and Banks, *J. Heterocyclic Chem.*, 8 (1972) 1005.

e) The following indenopyrimidinone

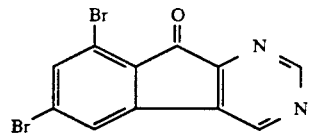

is prepared according to CA90:38958q.

f) 5H-indeno[1,2-c]pyridazine and 3-methyl-5H-indeno[1,2-c]pyridazine

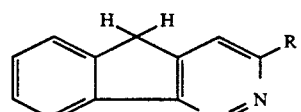

R = H, CH₃ is prepared according to Loriga et al., *Farmaco, Ed. Sci.*, 34 (1979) 72.

After spiro-derivatization the corresponding spiro-hydantoin, spiro-thiazolidinedione, spiro-oxazolidinedione and spiro-succinimide products are obtained.

PREPARATION Q

Synthesis substrates, 4H-indeno[2,3-c]-1,2,5-oxadiazol-4-one and 4H-ideno-[2,3-c]-1,2,5-oxadiazole and their derivatives are prepared in accordance with the following process (see Korte and Storiko, *Chemische Berichte*, 94 (1961) 1956). The starting material 4-oximino-3-phenyl-isoxazole is prepared according to *Ber. dtsch. Chem. Ges.*, 24 (1891) 140, see also Hantzsch and Heilbron, *Chemische Berichte*, 43 (1910) 68:

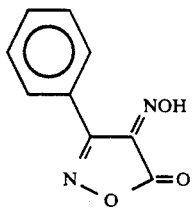

and hydrolyzed with water and treated with sodium carbonate to effect a rearrangement according to Korte, ibid.

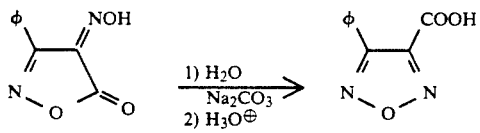

The resulting acid is cyclized by stepwise treatment with phosphorus pentachloride in methylene chloride followed by Friedel-Crafts cyclization catalyzed by stannic chloride. The resulting ketone is derivatized in accordance with Method I to yield the spiro-hydantoin

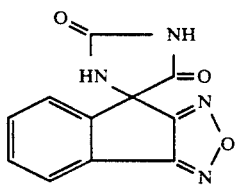

which may be further derivatized according to Method VI. The ketone may be reduced according to Method VIII (Wolff-Kishner reduction) and further derivatized in accordance with Method V. The substituted heterocycle may be oxidized back to the ketone in accordance to Method VII and then derivatized to the spiro-hydantoin. Alternately the heterocycle may be derivatized in accordance with Methods II, III and IV to the corresponding spiro-thiazolidinedione, spiro-oxazolidinedione and spiro-succinimide. These may be further derivatized in accordance with Method VI.

EXAMPLE I

9-Hydroxy-9H-fluorene-9-carboxylic acid methyl ester (1)

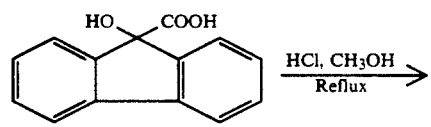

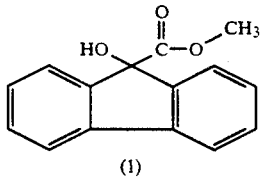

9-Hydroxy-9H-fluorene-9-carboxylic acid (Aldrich Chemical, Inc.) (20.0 g, 88.4 mmol) was added to 100 mL methanol saturated with hydrogen chloride and mixture was stirred at reflux for 4 h. The crystalline material obtained on cooling was collected by filtration and washed with cold 1:1 ethyl acetate/hexane to provide after drying (1), 15.8 g (74%).

Spiro-(9H-fluorene-9,5'-oxazolidine)-2',4'-dione (2)

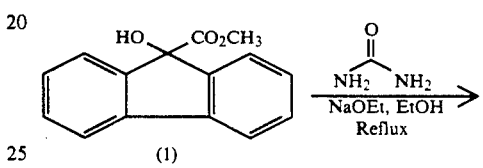

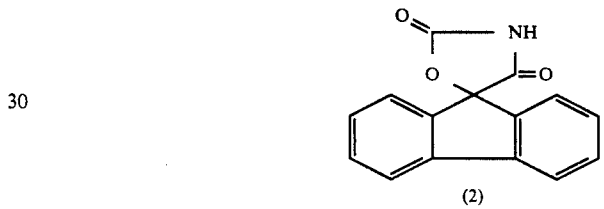

To a stirred solution of sodium (190 mg, 8.26 mmol) in 20 mL absolute ethanol was added urea (500 mg, 8.26 mmol) and 9-hydroxy-9H-fluorene-9-carboxylic acid methyl ester (1) (2.00 g, 8.26 mmol). The mixture was stirred at reflux under nitrogen for 15 h. After cooling to room temperature, the reaction mixture was poured into 100 mL water and acidified with 2N aqueous hydrochloric acid to precipitate the product which was collected by filtration, washed with water, and dried to provide 1.5 g crude (2). Recrystallization from ethyl acetate gave 260 mg (12%): m.p. 225°-257° C. A second crop, 620 mg (30%), was obtained by evaporation of the mother liquor followed by recrystallization from ethyl acetate/hexane. M/e+·251. For the preparation of oxazolidinediones from α-hydroxy esters using urea and sodium ethoxide, see: Stoughton, *J. Am. Chem. Soc.* (1941) 63, 2376.

EXAMPLE II

2-Fluoro-9H-fluorene-9-carboxylic acid (3)

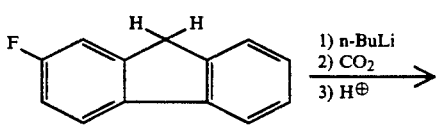

Under nitrogen atmosphere, n-butyllithium (1.25 eq, 0.170 mL, 65 mL of a 2.6M hexane solution) was added dropwise over 30 min. to a stirred 0.5° C. solution of 2-fluorofluorene (prepared according to U.S. Application Ser. Nos. 368,630 and 368,631) (25.0 g, 0.136 mmol) in 500 mL dry THF. After an additional 35 min. a flow of dry carbon dioxide gas into the solution was commenced and continued for 15 min. at 0°–15° C. and 45 min. at room temperature. 2N aqueous hydrochloric acid (200 mL) was added, and the mixture was transferred to a separatory funnel. The aqueous layer was separated and extracted 1×100 mL ethyl acetate. The combined organic phases were washed 1×100 mL brine, dried (MgSO₄), and evaporated to leave a dark residue which was triturated with 250 mL hexane to leave 16.6 g crude acid. Recrystallization from acetonitrile gave 10.2 g of the acid (3). A second crop of 2.0 g was obtained from the concentrated filtrate. Chromatography of the filtrate and the concentrated hexane extract on silica gel using 10–50% ethyl acetate/hexane provided another 2.8 g. Total yield: 15.0 g (48%).

2-Fluoro-9H-fluorene-9-carboxylic acid methyl ester (4)

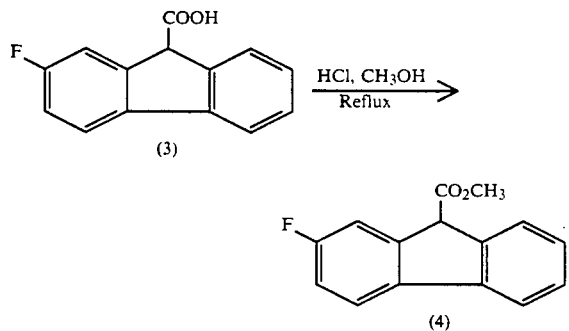

Acetyl chloride (33 mL) was added dropwise to a stirred, ice-cold solution of 2-fluoro-9H-fluorene-9-carboxylic acid (3) (16.7 g, 73.2 mmol) in 200 mL methanol and the solution was then refluxed for 4 h. Solvent removal left the crude product which was recrystallized from methanol to provide (4), 14.1 g (79%): m.p. 90°–92° C. (from hexane). For the preparation of 9H-fluorene-9-carboxylic acid from fluorene using phenyllithium and esterification using methanolic hydrogen chloride see: Bavin, *Anal. Chem.* (1960) 32, 554.

2-Fluoro-9-hydroxy-9H-fluorene-9-carboxylic acid methyl ester (5)

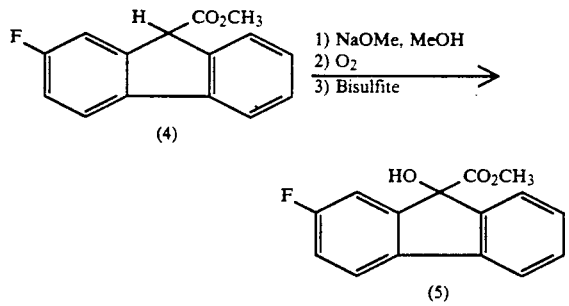

To a stirred solution of sodium (1.25 eq, 22.3 mmol, 510 mg) in 100 mL methanol was added 2-fluoro-9H-fluorene-9-carboxylic acid methyl ester (4) (4.33 g, 17.9 mmol). After 15 min. a flow of dry oxygen into the solution was commenced and continued for 1 h. Some of a solution of sodium bisulfite (24.5 g) in 300 mL water was added until the reaction became cloudy. The mixture was then poured into the remaining bisulfite solution. After cooling in ice, the solid that separated was collected by filtration, washed well with water, and dried to provide (5), 4.05 g (88%).

Spiro-(2-fluoro-9H-fluorene-9,5'-oxazolidine)-2',4'-dione (6)

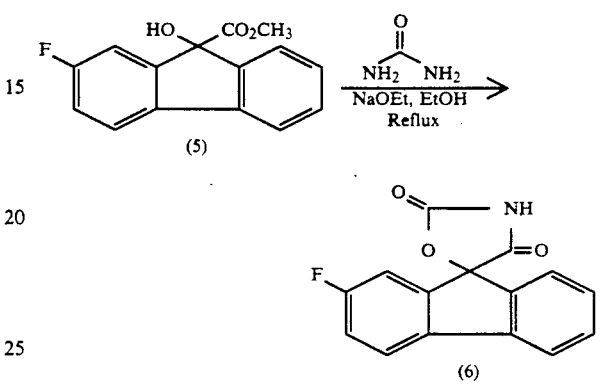

To a stirred solution of sodium (1.03 eq, 130 mg) in 13 mL absolute ethanol was added 2-fluoro-9-hydroxy-9H-fluorene-9-carboxylic acid methyl ester (5) (1.42 g, 5.5 mmol) and urea (5.5 mmol, 330 mg). The mixture was then refluxed 15 h. After cooling to room temperature, the mixture was poured into 65 mL water and acidified with 2N aqueous hydrochloric acid. The yellow solid that separated was collected, washed with water, and dried to give 1.19 g crude material. Chromatography on silica gel using 1–100% methanol/chloroform gave pure (6), 580 mg (39%). m/e+·269.

EXAMPLE III

9-Chloro-9H-fluorene-9-carboxylic acid methyl ester (7)

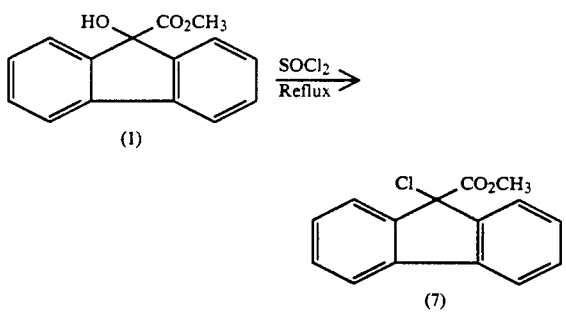

A mixture of 9-hydroxy-9H-fluorene-9-carboxylic acid methyl ester (1) (5.00 g, 20.8 mmol) and 50 mL thionyl chloride was heated at reflux for 3 h. The thionyl chloride was removed on the rotavapor to leave a solid residue which was redissolved in 50 mL benzene and then evaporated to remove traces of thionyl chloride. The resulting material was recrystallized from acetic acid to give (7), 3.23 g (60%): m.p. 111°–114° C. An additional 960 mg (18%) of product was obtained by chromatography of the reduced filtrate on silica gel using 10% ethyl acetate/hexane.

Spiro-[9H-fluorene-9,5'-(2'-amino-4'-thiazolone)] (8)

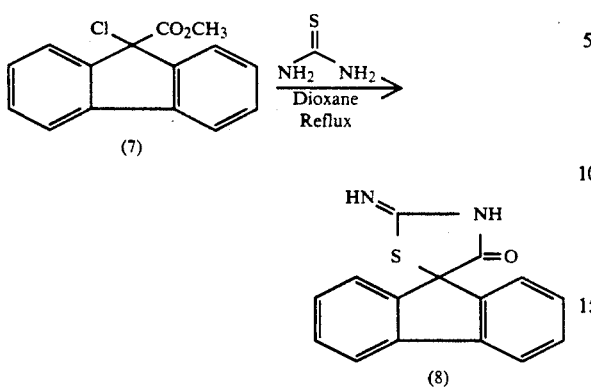

A mixture of 9-chloro-9H-fluorene-9-carboxylic acid methyl ester (7) (4.21 g, 16.3 mmol) and thiourea (1.24 g, 16.3 mmol) in 150 mL dioxane was heated at reflux for 10 h. After cooling to room temperature, the fine white solid present was collected by filtration and washed with dioxane providing (8), 1.31 g (30%). The gummy residue which remained in the flask was chromatographed on silica gel using 10–20% methanol/chloroform to give another 220 mg (5%) of (7): m.p. 320°–322° C. (dec). For the preparation of 2-imino-4-thiazolidinones from α-halo acid halides using thiourea in dioxane, see: Skinner, *J. Org. Chem.* (1961) 26, 1450.

Spiro-(9H-fluorene-9,5'-thiazolidine)-2',4'-dione (9)

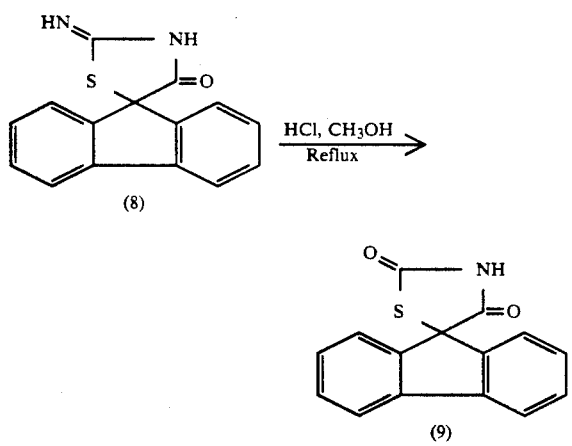

A mixture of spiro-[9H-fluorene-9,5'-(2'-amino-4'-thiazolone)] (8) (1.19 g, 4.47 mmol), 24 mL methanol, and 24 mL concentrated hydrochloric acid was refluxed 4 h. The reaction mixture was cooled in ice and the white precipitate was collected by filtration, washed with water, and dried to provide 640 mg crude (9). Recrystallization from acetonitrile gave 490 mg (41%): m.p. 253°–255° C. A second crop of 80 mg (7%) was obtained from the mother liquor. Calc. % C 67.40, % H 3.39; % N 5.24: meas. % C 67.46, % H 3.34, N 5.32. For the hydrolysis of 2-amino-4-thiazolones to thiazolidinediones using methanolic hydrogen chloride, see: Koltai, *Tetrahedron* (1973) 29, 2781.

EXAMPLE IV

9-Chloro-2-fluoro-9H-fluorene-9-carboxylic acid methyl ester (10)

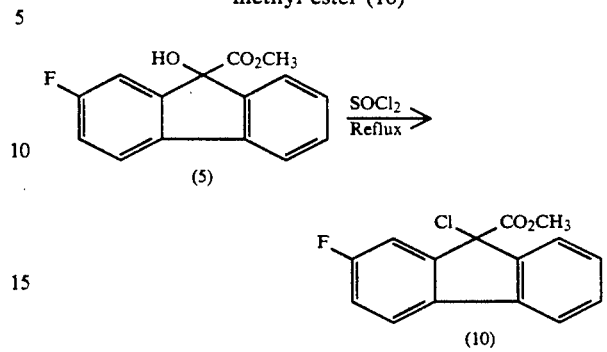

A mixture of 2-fluoro-9-hydroxy-9H-fluorene-9-carboxylic acid methyl ester (5) (4.00 g, 15.5 mmol) and 50 mL thionyl chloride was refluxed 3 h. After the thionyl chloride was removed on the rotavapor, the material was redissolved in 50 mL benzene and the benzene then evaporated to remove trace thionyl chloride. The crude product, 4.3 g (100%), was used without further purification.

Spiro-[2-fluoro-9H-fluorene-9,5'-(2'-amino-4'-thiazolone)] (11)

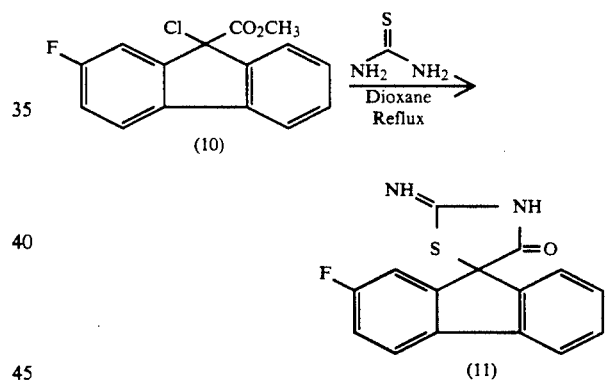

A mixture of 9-chloro-2-fluoro-9H-fluorene-9-carboxylic acid methyl ester (10) (4.31 g, 15.6 mmol) and thiourea (1.1 eq, 17.2 mmol, 1.31 g) in 140 mL dioxane was refluxed for 10 h. After cooling to room temperature, the fine white precipitate was collected by filtration and washed with water providing (11), 1.28 g (29%). An additional 1.3 g (29%) of (11) was obtained by chromatography of the reduced filtrate on silica gel using 5–50% methanol/chloroform.

Spiro-(2-fluoro-9H-fluorene-9,5'-thiazolidine)-2',4'-dione (12)

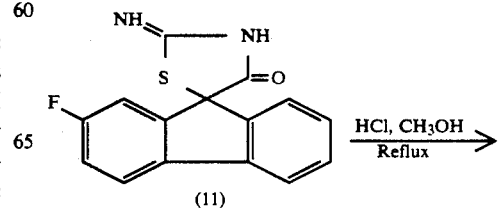

-continued

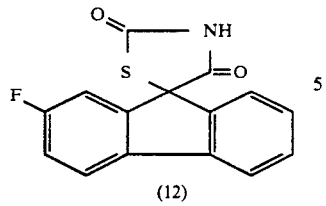

(12)

A mixture of spiro-[2-fluoro-9H-fluorene-9,5'-(2'-amino-4'-thiazolone)] (11) (1.85 g, 6.51 mmol), 35 mL methanol, and 35 mL concentrated hydrochloric acid was heated at reflux for 6 h. After cooling to room temperature, the white precipitate was collected by filtration and washed with water to provide 1.22 g of crude (12). Recrystallization from ethanol provided three crops totaling 870 mg (47%): m.p. 272°–276° C. (dec). m/e+·285.

EXAMPLE V 2,7-Difluoro-9H-fluorene-9-carboxylic acid (13)

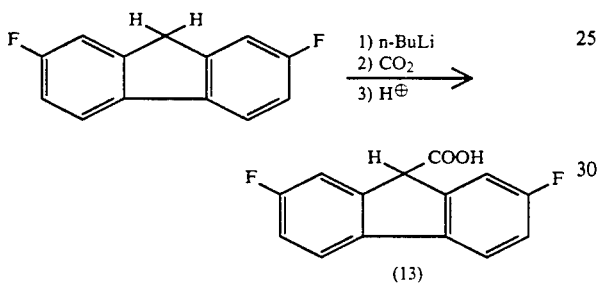

To a stirred, room temperature solution of 2,7-difluorofluorene (prepared according to U.S. application Ser. Nos. 368,630 and 368,631) (10.0 g, 49.5 mmol in 75 mL dry diethyl ether under a nitrogen atmosphere was added over 15 min n-butyllithium (1.25 eq, 61.9 mmol, 24 mL of a 2.6M hexane solution). The solution was refluxed 30 min., cooled to room temperature, and then quickly poured onto an ether slurry of a large excess of powdered dry ice. After the dry ice evaporated, the mixture was transferred to a separatory funnel along with 100 mL 2N aqueous hydrochloric acid and 50 mL ethyl acetate. After shaking well, the organic layer was separated and evaporated to dryness. The residue was extracted 2×100 mL warm (50° C.) 2% aqueous sodium hydroxide and then the extract was acidified with concentrated hydrochloric acid to precipitate the impure acid which was collected by filtration and washed with water. This material was dissolved in 50% ethyl acetate/hexane and passed through a 50 mm×7 silica gel column using the same solvent to remove highly colored, baseline impurities and to provide (13) sufficiently pure to be used in the next step, 7.91 g (65%): m.p. 128°–130° C. (from benzene).

2,7-Difluoro-9H-fluorene-9-carboxylic acid methyl ester (14)

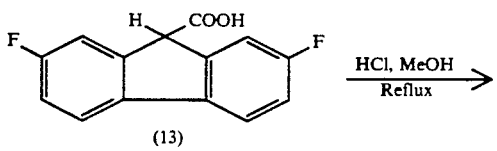

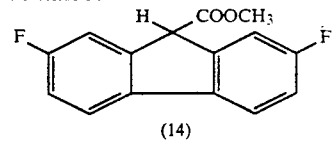

(14)

Acetyl chloride (13 mL) was added dropwise to a stirred, ice-cold solution of 2,7-difluoro-9H-fluorene-9-carboxylic acid (14) (6.90 g, 28 mmol) in 77 mL methanol. The mixture was then heated at reflux for 4 h. The product which crystallized upon cooling in ice was collected by filtration and washed with cold methanol to provide (14), 5.15 g (71%): m.p. 161°–163° C. (from toluene).

2,7-Difluoro-9-hydroxy-9H-fluorene-9-carboxylic acid methyl ester (15)

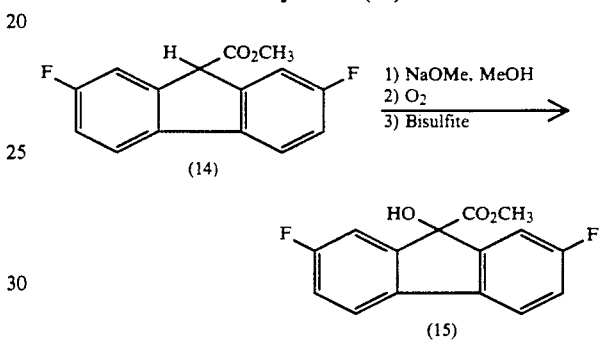

2,7-Difluoro-9H-fluorene-9-carboxylic acid methyl ester (14) (4.73 g, 18.2 mmol) was added to a solution of sodium (1.25 eq, 22.7 mmol, 520 mg) in 100 mL methanol. After 15 min., a flow of dry oxygen into the solution as commenced and continued for 1 h. Some of a solution of 24.5 g sodium bisulfite in 800 mL water was added until the mixture turned cloudy and then the whole was poured into the remaining bisulfite solution. The solid was collected by filtration, washed with water, and dried to provide (15), 4.68 g (93%): m.p. 174°–176° C. (from benzene).

9-Chloro-2,7-difluoro-9H-fluorene-9-carboxylic acid methyl ester (16)

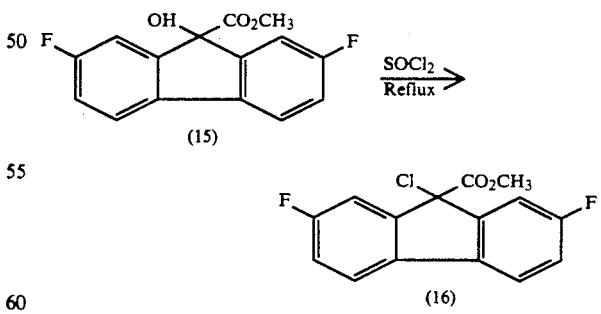

A mixture of 2,7-difluoro-9-hydroxy-9H-fluorene-9-carboxylic acid methyl ester (15) (3.63 g, 13.1 mmol) and 50 mL thionyl chloride was heated at reflux for 4 h. The reaction mixture was then diluted with 300 mL benzene and evaporated to leave (16), 3.7 g (96%), which was used in the next step without further purification: m.p. 140°–142° C. (from acetonitrile).

Spiro-[2,7-difluoro-9H-fluorene-9,5'-(2'-amino-4'-thiazolone)] (17)

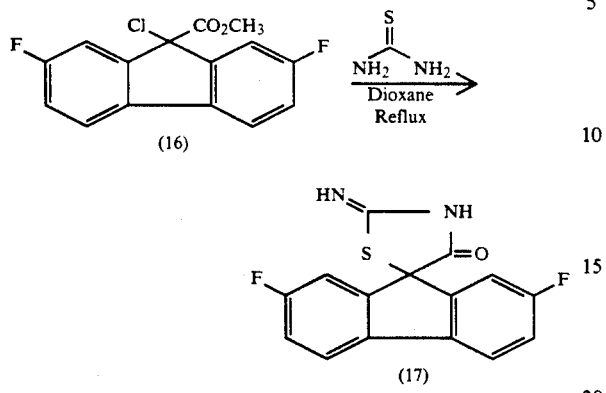

A mixture of 9-chloro-2,7-difluoro-9H-fluorene-9-carboxylic acid methyl ester (16) (3.56 g, 12.1 mmol) and thiourea (1.1 eq, 13.3 mmol, 1.01 g) in 110 mL dry dioxane was heated at reflux for 12 h. After cooling to room temperature and in ice, the white precipitate was collected by filtration, washed with dioxane, and dried to provide (17), 490 mg (13%). The concentrated filtrate and the gummy residue which remained in the flask were individually chromatographed on silica gel using 5-20% methanol/chloroform to provide another 1.00 g (27%) product: m.p. >300° C.

Spiro-(2,7-difluoro-9H-fluorene-9,5'-thiazolidine)-2',4'-dione (18)

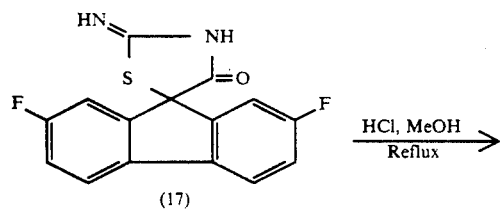

A mixture of spiro-[2,7-difluoro-9H-fluorene-(2'-amino-4'-thiazolone)] (17) (1.17 g, 3.87 mmol), 21 mL methanol, and 21 mL concentrated hydrochloric acid was refluxed for 6 h. The reaction mixture was cooled in ice and the off-white precipitate was collected by filtration, washed with water, and dried to provide 900 mg crude (18). This material was chromatographed on silica gel using 5-10% methanol/chloroform to yield pure (18), 530 mg (45%): m.p. 260°-263° C. (dec). Calc. % C 59.40, % H 2.33, % N 4.62: meas. % C 59.47, % H 2.42, % N 4.64.

EXAMPLE VI

Spiro-(9H-fluoren-9,3'-succinimide) (20)

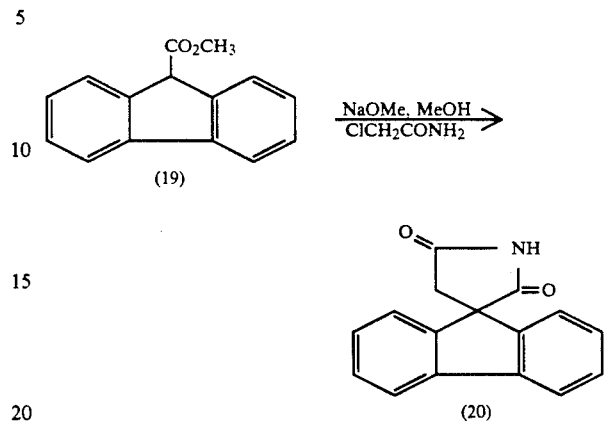

9H-fluoren-9-carboxylic acid methyl ester (19), which was prepared by refluxing 9H-fluoren-9-carboxylic acid (Aldrich Chemical, Inc.) in HCl/MeOH, (10.0 g, 44.6 mmol) was added to a solution of sodium (1.2 eq, 53.5 mmol, 1.23 g) in 100 mL methanol. After 15 min., 2-chloroacetamide (1.1 eq, 49.1 mmol, 4.59 g) was added and the mixture was allowed to stir at room temperature under nitrogen for two (2) days. The reaction mixture was poured into 400 mL of cold 2.5% w/v aqueous sodium hydroxide and the insoluble material was removed by filtration. The filtrate was chilled and acidified with concentrated hydrochloric acid to precipitate the spiro-succinimide which was collected and air dried to provide 6.7 g (60%). Recrystallization from methanol gave purified (20), 4.28 g (39%). m.p. 237°-239° C. Calc. % C 77.09, % H 4.45, % N 5.62: meas. % C 77.17, % H 4.55, % N 5.58.

EXAMPLE VII

Spiro-(2-fluoro-9H-fluoren-9,3'-succinimide) (21)

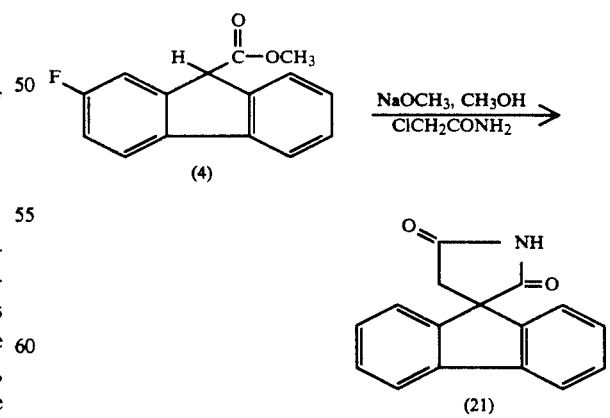

The spiro-succinimide (21), m.p. 248°-250° C., was prepared analogous to Example VI except from (4) in 25% yield. Calc. % C 71.90, % H 3.77, % N 5.24: meas. % C 71.97, % H 3.87, % N 5.33

EXAMPLE VIII

5H-Indeno[1,2-b]pyridine-5-carboxylic acid methyl ester (22)

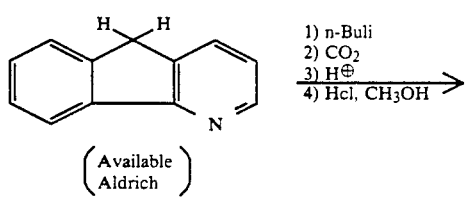

(Available Aldrich)

1) n-BuLi
2) CO₂
3) H⊕
4) Hcl, CH₃OH

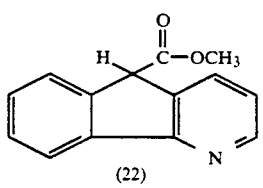

Under a nitrogen atmosphere, n-butyllithium (1.2 eq, 105 mmol, 65 mL of a 2.6M hexane solution) was added dropwise over a 30 min. period to a stirred 0°-5° C. solution of 4-azafluorene (14.65 g, 87.6 mmol) in 150 mL dry tetrahydrofuran (dried and distilled from LAH). After 1 h 20 min. the reaction mixture was poured into an ether slurry containing a large excess of dry ice. Solvents were allowed to evaporate overnight. The residue was suspended in 300 mL methanol, chilled and 60 mL acetyl chloride was added dropwise over 45 min. and the mixture stirred for 22 h at room temperature. Purification by chromatography (30% ethyl acetate/hexane on silica gel) and solvent evaporation yields 16.3 g (83%) of (22).

5-Hydroxy-5H-indeno[1,2-b]pyridine-5-carboxylic acid methyl ester (23)

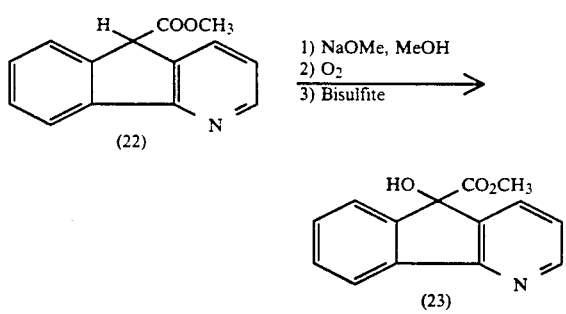

1) NaOMe, MeOH
2) O₂
3) Bisulfite

To a stirred solution of sodium (1.1 eq, 60.1 mmol, 1.38 g) in 150 mL dry methanol was added a solution of 5-hydroxy-5H-indeno[1,2-b]pyridine-5-carboxylic acid methyl ester (22) (12.3 g, 54.6 mmol) in 50 mL dry methanol. The solution was cooled in ice and, after 15 min., a flow of dry oxygen was begun and continued for 1 h. Then the reaction mixture was poured into a solution of 12 g sodium bisulfite in 200 mL water. After 30 min. the mixture was evaporated to dryness. The resulting solid was triturated with 2×100 mL acetone and filtered. The remaining inorganic salts were removed by filtration. The filtrate was evaporated to yield 24.2 g wet pink solid of (23). Drying in vacuo over phosphorus pentaoxide yielded 12.5 g crude (23). Recrystallization from ethyl acetate yielded two crops 8.06 g (61%) and 2.54 g (19%) of (23).

5-Chloro-5H-Indeno[1,2-b]Pyridine-5-Carboxylic Acid Methyl Ester (24)

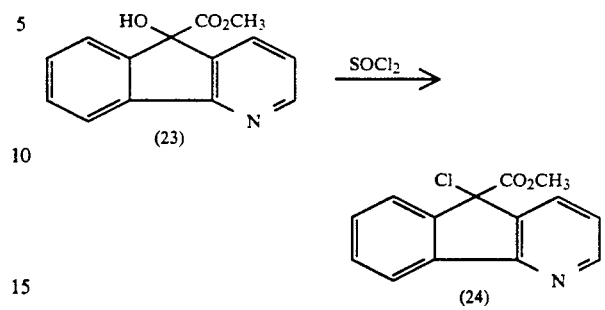

SOCl₂

A mixture of 5-hydroxy-5H-indeno[1,2-b]pyridine-5-carboxylic acid methyl ester (23) (8.06 g, 33.4 mmol) in 200 mL thionyl chloride was heated at reflux for 4 h. The thionyl chloride was removed on the rotavapor to leave a residue which was partitioned between water and chloroform and neutralized with saturated sodium bicarbonate. After further extractions with chloroform the combined chloroform extracts were dried over magnesium sulfate and evaporated to yield 7.87 g (91%) of (24).

Spiro-[5H-indeno[1,2-b]pyridine-5,5'-(2'-amino-4'-thiazolone)](25)

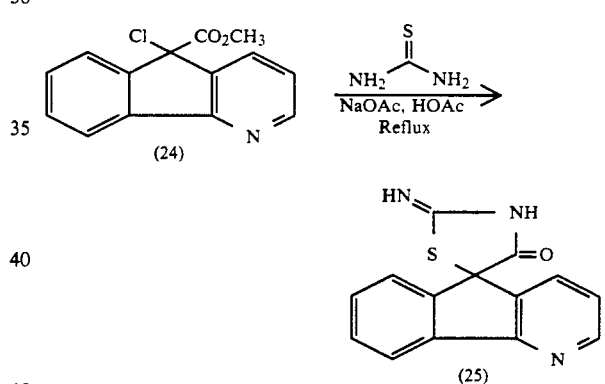

NaOAc, HOAc
Reflux

A mixture of 5-chloro-5H-indeno[1,2-b]pyridine-5-carboxylic acid methyl ester (24) (7.87 g, 30.4 mmol), thiourea (1.2 eq, 36.4 mmol, 2.77 g) and sodium acetate (1.1 eq, 33.4 mmol, 2.74 g) in 140 mL glacial acetic acid was refluxed for 40 min. Then 100 mL water was added and the pH was adjusted to 6.7 with hydrochloric acid. The aqueous portion was decanted from the precipitate, followed by additional 50 mL water wash. The dried residue was treated with ethyl acetate and the resulting crystalline solid was collected by filtration and dried to yield 1.81 g (32%) of (25).

Spiro-(5H-Indeno[1,2-b]Pyridine-5,5'-Thiazolidine)-2',4'-Dione (26)

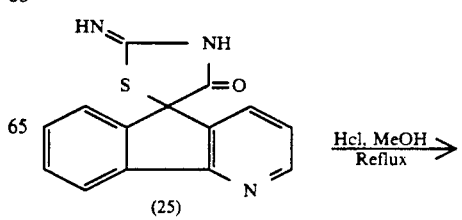

Hcl, MeOH
Reflux

-continued

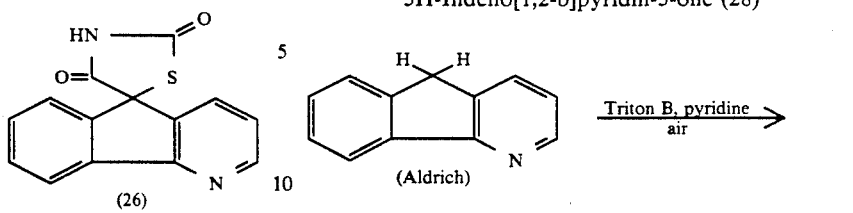

A mixture of spiro-[5H-indeno[1,2-b]pyridine-5,5'-(2'-amino-4'-thiazolone)](25) (1.00 g, 3.74 mmol) was stirred at reflux in a solution of 100 mL methanol and concentrated hydrochloric acid (1:1) for 2 h. The mixture was then concentrated to approximately 10 mL with heat and reduced pressure, chilled on ice and neutralized with sodium hydroxide solution. The resulting precipitate was collected by filtration and washed with water. Purification of the dried precipitate by chromatography (silica gel using 2.5-7% methanol/chloroform) yielded a product after solvent evaporation, 400 mg. Recrystallization of the residue from ethanol yielded crystalline (26). m/e+·268. IR strong bands at 1700 and 1745 cm$^{-1}$.

EXAMPLE IX

Spiro-(5H-indeno[1,2-b]pyridine-5,3'-succinimide) (27)

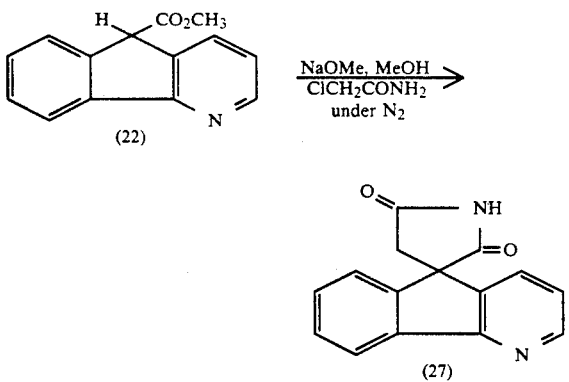

The ester (22) (4.00 g, 17.8 mmol) was added all at once to a stirred, room temperature solution of sodium methoxide in methanol (sodium metal, 1.2 eq, 21.3 mmol, 490 mg and 40 mL dry methanol). After 15 min., chloroacetamide (1.1 eq, 19.5 mmol, 1.83 g) was added and the mixture was left to stir at room temperature under nitrogen. After two days the reaction mixture was poured into 100 mL 1N sodium hydroxide, cooled in ice and the pH was adjusted with concentrated hydrochloric acid to pH 7. The precipitated solid was collected by filtration and washed with cold water. The dried solid (2.02 g) was recrystallized from ethyl acetate with charcoal treatment to yield 1.03 g (23%) crystalline (27). m.p. 245°-246° C. Calc. % C 71.99, % H 4.03, % N 11.20: meas. % C 71.85, % H 4.14, % N 11.17.

EXAMPLE X

5H-Indeno[1,2-b]pyridin-5-one (28)

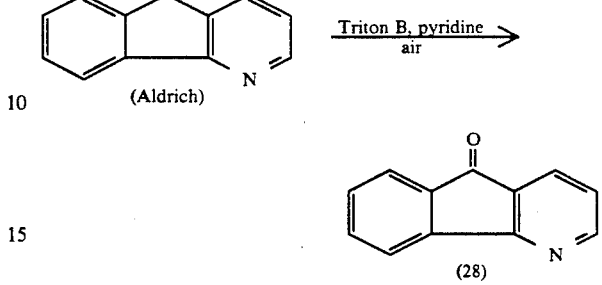

See general oxidation method of Sprinxak, J. Am. Chem. Soc., 80 (1958) 5449. 4-Azafluorene (5.0 g, 30 mmol) was dissolved in 50 mL anhydrous pyridine containing in solution 2 mL Triton B solution (prepared by evaporating 5 mL of 40% Triton B in methanol (Aldrich Chemical, Inc.) and 5 mL pyridine with heat and reduced pressure followed by q.s. to 10 mL with pyridine). Then air was continuously bubbled through the solution with stirring. An addition of 2 mL Triton B solution was made twice more at two-hour intervals. After six hours the reaction mixture was evaporated to dryness. The residue was triturated in 30 mL water and extracted four times with ethyl acetate (total volume 200 mL). The combined ethyl acetate extracts were dried over anhydrous sodium sulfate. After filtration and evaporation, the residue was chromatographed (silica gel and chloroform) to yield after evaporation of the solvent 4.5 g (83%) of (28). m.p. 132°-136° C. (reported 142° C.).

Spiro-(5H-Indeno[1,2-b]Pyridine-5,4'-Imidazolidine)-2',5'-Dione (29)

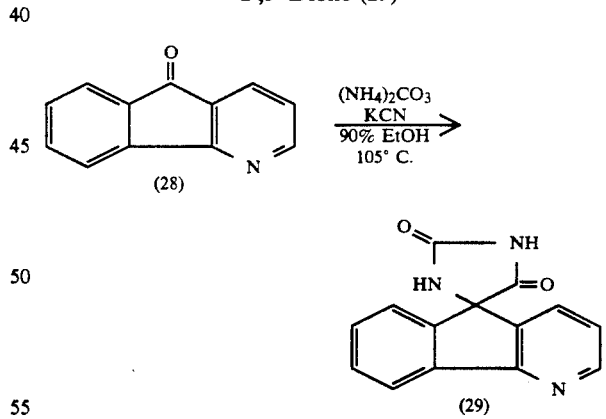

5H-Indeno[1,2-b]pyridine-5-one (4.0 g, 22 mmol) was mixed with potassium cyanide (1.6 g, 24 mmol) and ammonium carbonate (5.3 g, 55 mmol) in 90% ethanol (75 mL) in a pressure reactor and heated at 105° C. for 40 hr. The mixture was poured into 300 mL of water, acidified with conc. HCl (pH 1), and filtered. The filtrate was neutralized and the solid which formed collected by filtration, washed with water, and dried to yield 4.5 g. This solid was crystallized from ethyl acetate to yield 3.2 g of product. (This material was no longer soluble in ethyl acetate after the first crystallization). m/e+·251.

EXAMPLE XI

Spiro-(7-nitro-indeno[1,2-b]pyridin-5,4'-imidazolidine)-2',5'-dione (30)

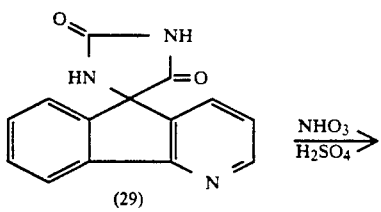

Spiro-(indeno[1,2-b]pyridine-5,4'-imidazolidine)-2',5'-dione (29) (1.0 g, 4 mmol) was added to cold concentrated sulfuric acid (10 mL) and stirred in an ice bath as concentrated nitric acid was added dropwise over about 10 min. The mixture was allowed to warm to room temperature and stirred overnight; the resulting solution was poured onto ice and the solution neutralized with concentrated aqueous sodium hydroxide. The solid which formed was collected by filtration, washed with a small volume of water, and dried. The product was dissolved in warm water (30 mL) by the addition of sodium hydroxide solution treated with Norite decolorizing charcoal, filtered through a celite bed and the bed washed with a small volume of warm dilute base. The combined filtrate and wash were neutralized with hydrochloric acid to yield a solid which was collected by filtration, washed with water and dried to yield 0.76 g of (30). Calc. % C 56.76, % H 2.72, % N 18.91: meas. % C 56.59, % H 2.83, % N 18.87. m/e+·296.

EXAMPLE XII

Spiro-(7-bromo-indeno[1,2-b]pyridine-5,4'-imidazolidine)-2',5'-dione (31)

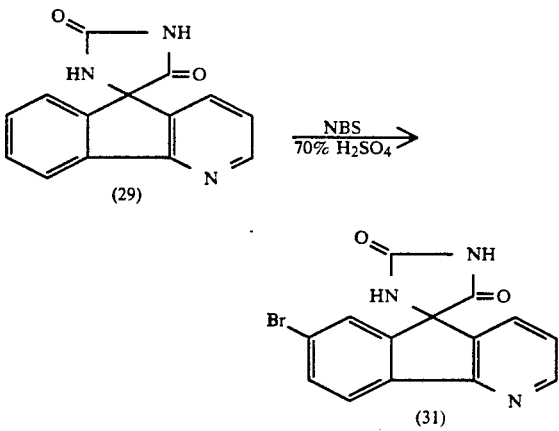

Spiro-(indeno[1,2-b]pyridin-5,4'-imidazolidine)-2',5'-dione (29) (1.0 g, 4 mmol) was dissolved in cold 70% sulfuric acid (50 mL). The solution was heated to 50° C., and N-bromosuccinimide (0.78 g, 4.3 mmol) was added in small portions with stirring. After stirring at 50° C. for 2 h, the reaction was poured onto ice, and the solution was neutralized with concentrated aqueous sodium hydroxide. The solid which formed was collected by filtration and washed with water. The sample was dissolved in 30 mL of warm water by addition of aqueous sodium hydroxide then treated with Norite, filtered through a celite bed and washed with warm dilute base, and the combined filtrate and wash were acidified with hydrochloric acid (to pH 6). The solid was collected by filtration, washed with water, and dried to yield 0.88 g of (31). m/e+·329.

EXAMPLE XIII 4H-indeno[1,2-b]thiophen-4-one (35)

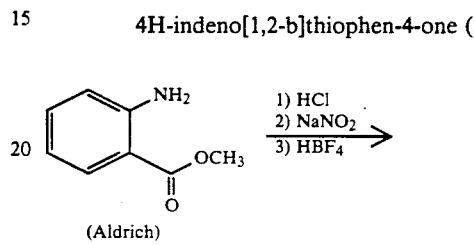

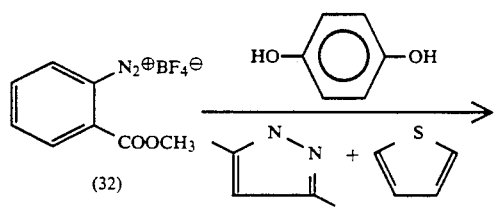

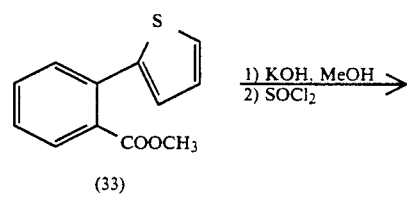

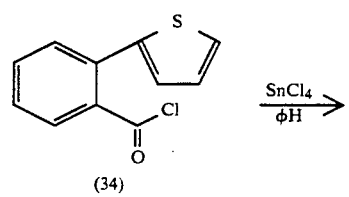

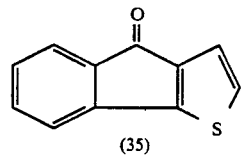

To methyl anthranilate (90.0 g, 77 mL, 595 mmol, 1.0 eq) was added hydrochloric acid (120 mL of conc., 1450 mmol, 2.4 eq diluted with 100 mL distilled water). The resulting mixture of solid and liquid was heated to reflux with stirring while protected from light. The hot clear solution was cooled to 5° C. whereupon a solid precipitated. To this stirred mixture was added sodium nitrite solution (41.09 g, 596 mmol, 1.0 eq in 90 mL distilled water) at a rate to maintain the reaction temperature below 5° C. After 1.5 h fluoroboric acid (95 g, 48% in water) was added rapidly and the resulting suspension was stirred for an additional 30 min. at −10° to 0° C.

The suspended solid was collected by filtration, washed with 100 mL cold water, 120 mL cold methanol and 500 mL ether. The resulting pink solid was dried in vacuo over concentrated sulfuric acid to yield 39.5 g of (32) as a pink solid (m.p. 93°–98° C. with decomposition, reported 102° C. with decomposition *Org. Reactions* 5, 219).

To a diazo salt (32) (39.5 g, 158 mmol, 1.0 eq) in thiophene (75 mL) stirred suspension was dropwise added during 1 h a solution consisting of 3,5-dimethylpyrazole (15.80 g, 164 mmol, 1.04 eq) and hydroquinone (1.91 g, 17 mmol, 0.11 eq) in 125 mL thiophene at 0° C. After 2.5 h additional stirring at 0°–5° C. the reaction was stirred overnight at ambient temperature (see *J. Org. Chem.*, 46 (1981) 3960). Evaporation with heat and reduced pressure yielded a brown semisolid. Column chromatography (silica gel, 1:9 to 1:4 ethyl ether/petroleum ether) yields 19.4 g. Distillation (bp 141°–160° C., 4 mmHg) yields 15.1 g of (33).

To 15.1 g of (33) was added methanolic potassium hydroxide (12.8 g KOH in 200 mL methanol) and the reaction mixture was refluxed for 4 h whereupon potassium hydroxide (2.5 g) was added. After 5 h total refluxing, the starting material (33) was completely hydrolyzed (silica gel, 40% Pet ether/ether). To the cooled mixture was added 250 mL water and the diluted mixture was extracted with 250 mL ethyl ether. The ether extract was back extracted with 150 mL 10% KOH. The combined aqueous fractions were cooled and acidified with concentrated hydrochloric acid to pH 2. The acidified slurry was then extracted with diethyl ether (3×200 mL), the ether extracts washed with brine (150 mL) then dried with anhydrous magnesium sulfate. After filtration and evaporation, 23.7 g tan solid resulted. m.p. 80° C. (reported m.p. 93°–94° C., *J. Med. Chem.*, 9 (1966) 551). To the acid (13.7 g, 69.2 mmol, 1.0 eq) was added thionyl chloride (25.3 mL, 213 mmol, 3.1 eq) and the mixture was refluxed for 2 h. After cooling the reaction mixture was evaporated with reduced pressure and heat with 3×100 mL benzene additions to result in 15 g of (34) as a dark oil.

Under nitrogen, a stannic chloride solution (SnCl4, 9.1 g, 4.1 mL, 1.25 eq in 40 mL benzene) was added over 20 min. to a benzene (100 mL) solution of the acid chloride (34) (15 g, 69.2 mmol) at 0°–4° C. with mechanical stirring. After a total of 30 min. the reaction mixture was poured into 200 cc ice containing 100 mL 1N hydrochloric acid. (See *J. Org. Chem.*, 35 (1970) 872). Ethyl acetate extractions (600 mL) of the aqueous mixture yielded a dark organic extract. Washing the organic extract with 100 mL 100% sodium hydroxide, 100 mL water (2X) yielded an orange ethyl acetate extract which was dried over anhydrons magnesium sulfate. Filtration and evaporation yielded a dark residue. Column chromatography (silica gel, 1:9 ethyl ether/petroleum ether) yields a purified 4.5 g sample of orange (35). m.p. 99.5°–101.5° C. from hexane. (lit. 101° C., *J. Org. Chem.* 35 (1970) 872). Calc. % C 70.94, % H 3.25, % S 17.22: meas. % C 70.98, % H 3.33, % S 17.16.

Spiro-(4H-indeno[1,2-b]thiophen-4,4'-imidazolidine)-2',5'-dione (36)

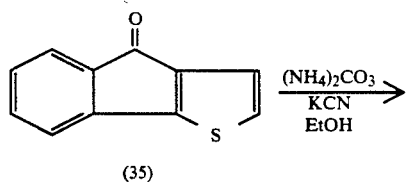

(35)

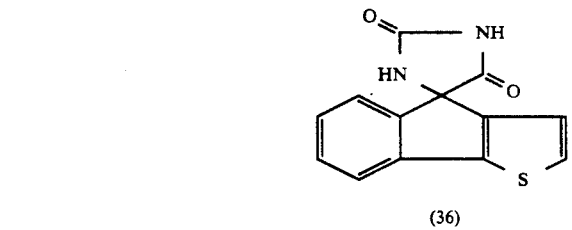

(36)

To a glass-lined, High-pressure steel reaction vessel was added ketone (35) (373 mg, 2 mmol), potassium cyanide (406 mg, 5 mmol), ammonium carbonate (577 mg, 6 mmol) and ethanol (15 mL). The sealed vessel was heated at 110° C. for 24 h. The dark reaction mixture was poured into water and acidified with concentrated hydrochloric acid to pH 1. The resulting dark solid was collected by filtration and resolubilized in 10% sodium hydroxide (30 mL), treated with charcoal and filtered. The filtrate was acidified with concentrated hydrochloric acid. The resulting precipitate was collected by filtration and dried. The solid was dissolved in dimethylformamide, treated with Darco G-60 and filtered through a Celite pad. Dilution with water (3× volume) resulted in a precipitate which was collected by filtration. The collected solid was dissolved in 10% sodium hydroxide (3 mL), filtered, and the filtrate was acidified with conc. hydrochloric acid, the white precipitate collected by filtration, washed with water and dried at 105° C. to yield 110 mg of (36). m.p. 336°–8° C. Calc. % C 60.92, % H 3.15, % N 10.96: meas. % C 60.83, % H 3.22, % N 10.97.

EXAMPLE XIV

8H-Indeno[2,1-b]thiophen-8-one (38):

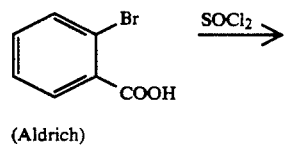

(Aldrich)

-continued

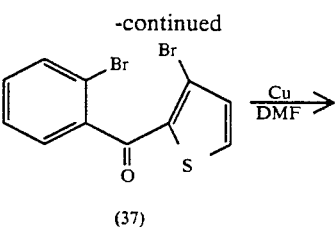

(37)

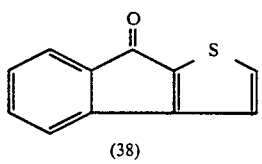

(38)

Thionyl chloride (60.3 g, 37 mL, 500 mmol, 3.6 eq) was added at 25° C. to o-bromobenzoic acid (Aldrich Chemical, Inc.) (28.1 g, 140 mmol, 1.0 eq). After addition the reaction mixture was heated to 80° C. for 13 h. Evaporation with heat and reduced pressure partially reduced the volume. Then under nitrogen atmosphere 100 mL methylene chloride followed by 3-bromothiophene (Aldrich Chemical, Inc.) (22.8 g, 13.1 mL, 140 mmol, 1.0 eq) in 100 mL methylene chloride were added to acyl chloride intermediate. Then aluminum trichloride (23.9 g, 179 mmol, 1.3 eq) was added in small portions to the reaction mixture at 0° C. After addition, the reaction mixture was allowed to slowly reach room temperature. After 17 h the reaction was quenched by the slow addition of 150 mL 2N hydrochloric acid. Water (2×150 mL) and brine (100 mL) washing, drying over anhydrous magnesium sulfate, filtration and evaporation of the filtrate in vacuo yielded approximately 50 g of an oil of (37) which solidified in the freezer. IR 1645 cm$^{-1}$ for diaryl ketone.

Diaryl ketone (37) (44 g, 480 mmol, 4 eq) and activated copper (prepared from aqueous copper sulfate, zinc dust, 5% hydrochloric acid) (30 g, 480 mmol, 4 eq) in 200 mL dimethylformamide were refluxed for 6.5 h. After the cooling the reaction mixture was filtered and 150 mL water added. The filtrate was extracted with ethyl ether (5×150 mL). The combined ether extracts were washed with 150 mL 1N hydrochloric acid, 150 mL water and 150 mL brine. Then the ether solution was dried over anhydrous magnesium sulfate, filtered and evaporated to yield a solid, 18.6 g (79%). Recrystallization from hexane yielded purified (38) m.p. 111°–112° C. Calc. % C 70.97, % H 3.25, % S 17.22: meas. % C 70.71, % H 3.26, % S 17.12.

Spiro-(8H-indeno[2,1-b]thiophen-8,4'-imidazolidine)-2',5'-dione (39)

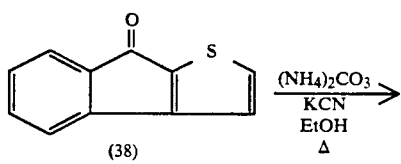

-continued

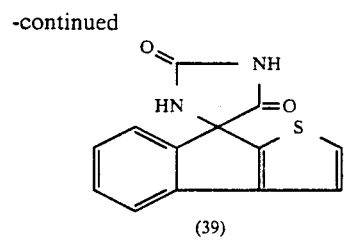

(39)

To a glass-lined, high-pressure steel reaction vessel was added ketone (38) (931.2 mg, 5 mmol), potassium cyanide (1.01 g, 12.5 mmol), ammonium carbonate (1.45 g, 18 mmol) and 25 mL ethanol. The sealed vessel was heated at 115°–120° C. for 20 h. The work-up procedure was very similar to that for spiro-hydantoin (36) of Example XIII. The purified product (39), 200 mg, gave m/e+·256. Calc. % C 60.92, % H 3.15, % N 10.96: meas. % C 60.88, % H 3.22, % H 10.79.

EXAMPLE IV

Spiro-(9H-pyrrolol[1,2-a]indol-9,4'-imidazolidine)-2',4'-dione (41)

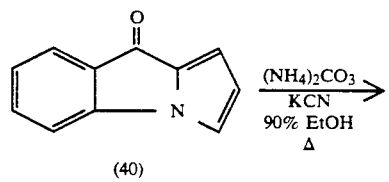

(40)

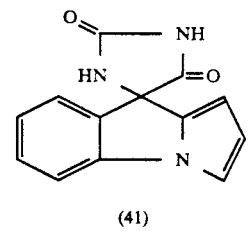

(41)

9H-Pyrrolol[1,2-a]indole-9-one (40) was prepared exactly according to Josey and Jenner, J. Org. Chem., 27 (1962) 2466. The ketone (40) (2.5 g, 15 mmol), potassium cyanide (2.44 g, 37.5 mmol), ammonium carbonate (4.85 g, 45 mmol) and 50 mL 90% ethanol were added with mixing to a 125 cc stainless steel pressure reaction vessel. The sealed vessel was heated to 115°–118° C. for 48 h. The work-up was as in Example XIII in the workup of (36). The collected and dried sample, 650 mg of (41), gave decomposition at >290° C. Calc. % C 65.26, % H 3.79, % N 17.56: meas. % C 65.16, % H 4.00, % N 17.59.

EXAMPLE XVI

Spiro-(9H-indeno[2,1-c]pyridin-9,4'-imidazolidine]-2',5'-dione (43)

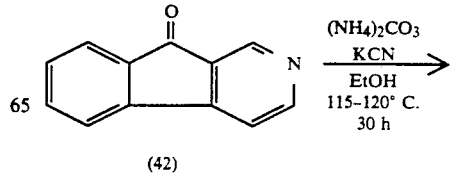

(42)

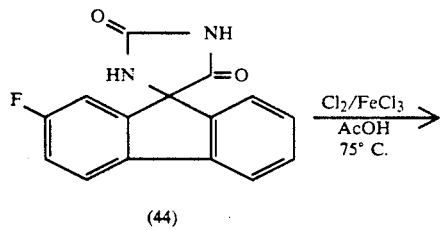

(43)

2-Azafluoren-9-one (42) was prepared from 3-mesitoyl-4-phenyl-pyridine exactly according to Fuson and Miller, *J. Am. Chem. Soc.*, 79 (1957) 3477. m.p. 152°–153° C. (reported 155.5°–156.5° C. by Fuson and Miller, ibid). The ketone (42) (0.5 g, 2.8 mmol), potassium cyanide (0.2 g, 3.1% mmol), ammonium carbonate (1.0 g, 11 mmol) and 10 mL absolute ethanol were added with mixing to a 40 cc stainless steel pressure reactor. The sealed vessel was heated at 115°–120° C. for 30 h. The cooled reaction mixture was poured into 75 mL water, acidified with concentrated hydrochloric acid, filtered, the filtrate was made basic with 10% sodium hydroxide and filtered. The filtrate was neutralized with hydrochloric acid, the precipitate collected, washed with cold water and dried to yield 0.11 g of (43). m/e+ 251.

EXAMPLE XVII

Spiro-(2-chloro-7-fluoro-9H-fluoren-9,4′-imidazolidine)-2′,5′-dione (45)

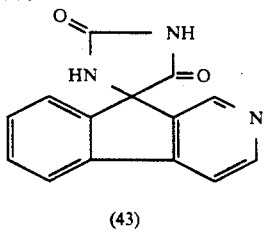

(44)

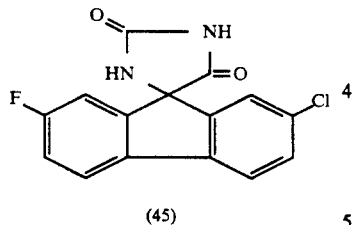

(45)

The spiro-hydantoin (44), spiro-(2-fluoro-9H-fluoren-9,4′-imidazolidine)-2′,5′-dione, was prepared exactly according to U.S. application Ser. Nos. 368,630 and 368,631. A mixture of (44) (5.36 g, 20 mmol), ferric chloride (0.25 g), glacial acetic acid solution of chlorine gas (5 g Cl$_2$ in 25 mL HOAc) and 200 mL glacial acetic acid were heated at 75° C. overnight. The cooled reaction mixture was poured into 200 mL water, stirred and the solid was collected by filtration. After water washes, the solid product was dried with 50° C. heat in vacuo to yield 2.3 g of (45). Calc. % C 59.52, % H 2.66, % N 9.25: meas. % C 59.35, % H 2.77, % N 9.26.

EXAMPLE XVIII 7-fluoro-5H-indeno[1,2-b]pyridine (50)

The procedure used for the preparation of 5-fluoro-1-indanone is that of Olivier and Marechal (*E. Bull. Soc. Chim. Fr.* (1973) 3092–3095) with modifications. The conversion of the ketone to 7-fluoro-5H-indeno[1,2-b]pyridine followed the general procedure described by Parcell and Hauck (*J. Org. Chem.* (1963) 28, 3468–3473) for the preparation of 5H-indeno[1,2-b]pyridine from 1-indanone.

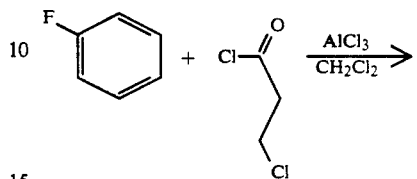

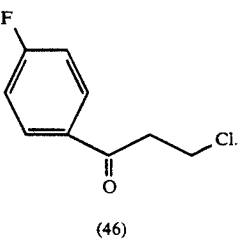

(46)

Aluminum chloride (350 g, 2.62 mol) was covered with 650 mL methylene chloride and, while stirring under nitrogen, a solution of 3-chloropropionyl chloride (400 g, 3.15 mol, 300 mL) in 250 mL methylene chloride was added over 80 min. After 15 min., a solution of fluorobenzene (256 g, 2.66 mol, 250 mL) in 250 mL methylene chloride was added over 1 h 35 min. The reaction mixture was stirred, under nitrogen, at room temperature overnight (ca 18 h). The mixture was then poured onto 2.5 kg ice and transferred to a 4 L separatory funnel. After shaking well, the organic layer was removed and the aqueous portion was extracted with 2×50 mL methylene chloride. The combined organic extracts were washed with 3×200 mL saturated aqueous sodium bicarbonate and 1×200 mL brine, dried (MgSO$_4$), and evaporated to leave an oil which crystallized on cooling. Recrystallization from 2 L hexane gave 325 g (67%). The filtrate was concentrated to 500 mL and cooled to provide another 42 g (9%) of product (46).

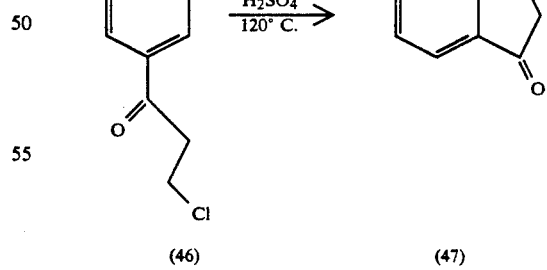

(46)　　　　　(47)

3-Chloro-1-(4-fluorophenyl)propanone (46) (366 g, 1.97 mol) and 2.2 L concentrated sulfuric acid were combined in a 5 L flask equipped with a mechanical stirrer and heated over a period of 80 min. to 120° C. and then maintained at that temperature for 30 min. Hydrogen chloride evolution began at about 80° C. The reaction mixture was then cooled to 20° C., poured onto 5 kg of ice in a 22 L flask equipped with a bottom drain and a mechanical stirrer, and extracted with 6×1 L chloroform. The combined extracts were washed with 2×1 L saturated aqueous sodium bicarbonate and 1×1 L brine, dried (MgSO₄), and concentrated to leave a dark oil. Distillation gave the ketone, (47) 97.9 g (33%), bp 61°–66° C./0.15–0.2 mm, discolored by some dark material which was carried over during the process.

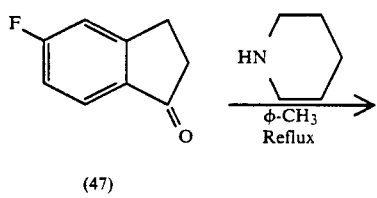

(47)

A solution of 5-fluoro-1-indanone (47) (20.2 g, 0.135 mol), p-toluene-sulfonic acid monohydrate (0.015 eq, 390 mg), and piperidine (1.1 eq, 0.148 mol, 15 mL) in 300 mL toluene was refluxed under a Dean-Stark trap for 30 h. The reaction mixture was concentrated and distilled to provide the enamine, (48) 8.6 g (29%); bp 95°–100° C./1.5 mm.

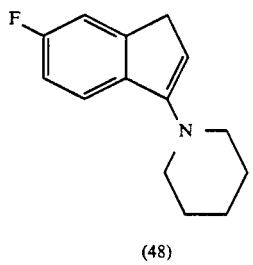

(48)

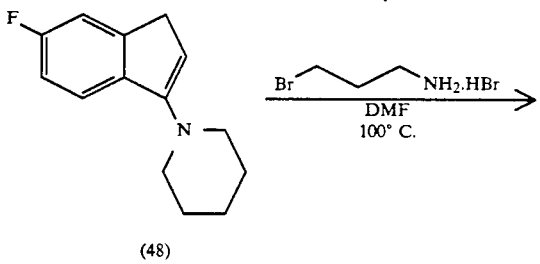

(48)

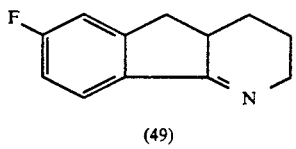

(49)

A solution of the enamine (8.6 g, 40 mmol) in 10 mL dry DMF was added all at once to a stirred solution of bromopropylamine hydrobromide (1.0 eq, 8.67 g) in 15 mL DMF. The stirred mixture was heated to 100° C. under nitrogen and then kept at that temperature for 4 h. The reaction mixture was poured into 60 mL cold 2N aqueous hydrochloric acid and extracted with 2×50 mL ethyl ether to remove any non-basic material. The aqueous solution was then covered with 50 mL ether, chilled, and basified using concentrated sodium hydroxide. After separating the organic layer, the aqueous portion was extracted with 2×50 mL ether and the combined extracts were washed with 1×50 mL brine, dried (MgSO₄), and concentrated to leave 7.8 g of a dark oil. Distillation provided the tetrahydropyridine, 3.46 g (46%); bp 83°–86° C./0.15 mm.

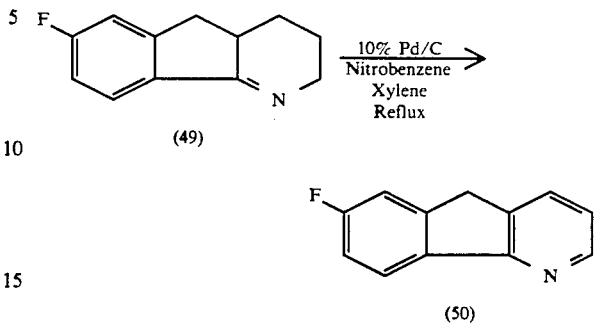

(49)

(50)

A mixture of the tetrahydropyridine (49) (3.19 g, 16.9 mmol), 10 mL xylene, 10 mL nitrobenzene, and 350 mg 10% palladium on carbon was refluxed for 4 h under a Dean-Stark trap under nitrogen. The reaction mixture was then cooled to room temperature and filtered through Celite, washing with ethyl acetate. The filtrate was extracted with 3×20 mL 2N aqueous hydrochloric acid and then the combined extracts were washed with 2×25 mL ethyl ether to remove non-basic material. Basification using solid potassium carbonate resulted in the precipitation of a dark green solid that was collected by filtration and washed well with water. This material 2.3 g (75%), was judged sufficiently pure by NMR to use in the next step. The material can further be purified by chromatography on silica gel using 30% ethyl acetate/hexane to give a yellow solid of (50) mp 80°–84° C.

The product (50) can be oxidized in accordance with Method VII and derivatized according to Method I into the corresponding spiro-hydantoin.

The product (50) can be derivatized in accordance with Methods II, III and IV into the corresponding spiro-thiazolidinedione, spiro-oxazolidinedione and spiro-succinimide.

EXAMPLE XIX

Following the foregoing text of preparations and examples, from readily available starting materials, the following spiro-derivatives of the present invention are prepared by analogy. All structional permutations occasioned by the substitution patterns and the values of U and Z on the following tricyclic structures are fully comtemplated and intended as evidenced by the table entries.

UNSUBSTITUTED PARENT STRUCTURES FOR COMPOUNDS 1–328: A–D

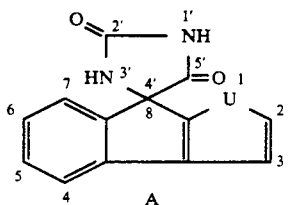

A

-continued

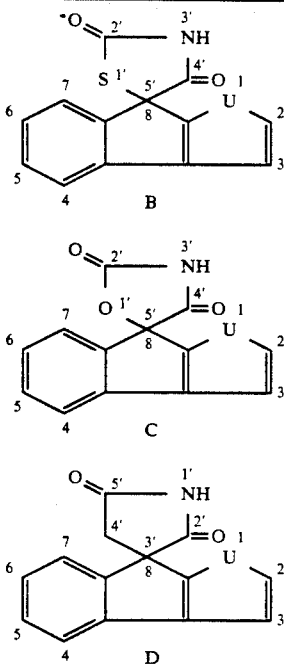

| Compound No. | Ring Substitution | U |
|---|---|---|
| 1-4:A-D | 7-F | NH, N—CH$_3$, S, O |
| 5-8:A-D | 6-F | NH, N—CH$_3$, S, O |
| 9-12:A-D | 5-F | NH, N—CH$_3$, S, O |
| 13-16:A-D | 4-F | NH, N—CH$_3$, S, O |
| 17-20:A-D | 7-F, 2-CH$_3$ | NH, N—CH$_3$, S, O |
| 21-24:A-D | 7-F, 3-CH$_3$ | NH, N—CH$_3$, S, O |
| 25-28:A-D | 6-F, 2-CH$_3$ | NH, N—CH$_3$, S, O |
| 29-32:A-D | 6-F, 3-CH$_3$ | NH, N—CH$_3$, S, O |
| 33-36:A-D | 5-F, 2-CH$_3$ | NH, N—CH$_3$, S, O |
| 37-40:A-D | 5-F, 3-CH$_3$ | NH, N—CH$_3$, S, O |
| 41-44:A-D | 4-F, 2-CH$_3$ | NH, N—CH$_3$, S, O |
| 45-48:A-D | 4-F, 3-CH$_3$ | NH, N—CH$_3$, S, O |
| 49-52:A-D | 7-Cl | NH, N—CH$_3$, S, O |
| 53-56:A-D | 6-Cl | NH, N—CH$_3$, S, O |
| 57-60:A-D | 5-Cl | NH, N—CH$_3$, S, O |
| 61-64:A-D | 4-Cl | NH, N—CH$_3$, S, O |
| 65-68:A-D | 7-Cl, 2-CH$_3$ | NH, N—CH$_3$, S, O |
| 69-72:A-D | 7-Cl, 3-CH$_3$ | NH, N—CH$_3$, S, O |
| 73-76:A-D | 6-Cl, 2-CH$_3$ | NH, N—CH$_3$, S, O |
| 77-80:A-D | 6-Cl, 3-CH$_3$ | NH, N—CH$_3$, S, O |
| 81-84:A-D | 5-Cl, 2-CH$_3$ | NH, N—CH$_3$, S, O |
| 85-88:A-D | 5-Cl, 3-CH$_3$ | NH, N—CH$_3$, S, O |
| 89-92:A-D | 4-Cl, 2-CH$_3$ | NH, N—CH$_3$, S, O |
| 93-96:A-D | 4-Cl, 3-CH$_3$ | NH, N—CH$_3$, S, O |
| 97-100:A-D | 7-F, 6-F | NH, N—CH$_3$, S, O |
| 101-104:A-D | 7-F, 5-F | NH, N—CH$_3$, S, O |
| 105-108:A-D | 7-F, 4-F | NH, N—CH$_3$, S, O |
| 107-112:A-D | 6-F, 5-F | NH, N—CH$_3$, S, O |
| 113-116:A-D | 6-F, 4-F | NH, N—CH$_3$, S, O |
| 117-120:A-D | 5-F, 4-F | NH, N—CH$_3$, S, O |
| 121-124:A-D | 7-Cl, 6-Cl | NH, N—CH$_3$, S, O |
| 125-128:A-D | 7-Cl, 5-Cl | NH, N—CH$_3$, S, O |
| 129-132:A-D | 7-Cl, 4-Cl | NH, N—CH$_3$, S, O |
| 133-136:A-D | 6-Cl, 5-Cl | NH, N—CH$_3$, S, O |
| 137-140:A-D | 6-Cl, 4-Cl | NH, N—CH$_3$, S, O |
| 141-144:A-D | 5-Cl, 4-Cl | NH, N—CH$_3$, S, O |
| 145-148:A-D | 7-F, 6-Cl | NH, N—CH$_3$, S, O |
| 149-152:A-D | 7-F, 5-Cl | NH, N—CH$_3$, S, O |
| 153-156:A-D | 7-F, 4-Cl | NH, N—CH$_3$, S, O |
| 157-160:A-D | 6-F, 7-Cl | NH, N—CH$_3$, S, O |
| 161-164:A-D | 6-F, 5-Cl | NH, N—CH$_3$, S, O |
| 165-168:A-D | 6-F, 4-Cl | NH, N—CH$_3$, S, O |
| 169-172:A-D | 5-F, 7-Cl | NH, N—CH$_3$, S, O |
| 173-176:A-D | 5-F, 6-Cl | NH, N—CH$_3$, S, O |
| 177-180:A-D | 5-F, 4-Cl | NH, N—CH$_3$, S, O |
| 181-184:A-D | 4-F, 7-Cl | NH, N—CH$_3$, S, O |
| 185-188:A-D | 4-F, 6-Cl | NH, N—CH$_3$, S, O |
| 189-192:A-D | 4-F, 5-Cl | NH, N—CH$_3$, S, O |
| 193-196:A-D | 7-F, 6-F, 2-CH$_3$ | NH, N—CH$_3$, S, O |
| 197-200:A-D | 7-F, 5-F, 2-CH$_3$ | NH, N—CH$_3$, S, O |
| 201-204:A-D | 7-F, 4-F, 2-CH$_3$ | NH, N—CH$_3$, S, O |
| 205-208:A-D | 7-F, 6-F, 3-CH$_3$ | NH, N—CH$_3$, S, O |
| 209-212:A-D | 7-F, 5-F, 3-CH$_3$ | NH, N—CH$_3$, S, O |
| 213-216:A-D | 7-F, 4-F, 3-CH$_3$ | NH, N—CH$_3$, S, O |
| 217-220:A-D | 6-F, 5-F, 2-CH$_3$ | NH, N—CH$_3$, S, O |
| 221-224:A-D | 6-F, 4-F, 2-CH$_3$ | NH, N—CH$_3$, S, O |
| 225-228:A-D | 6-F, 5-F, 3-CH$_3$ | NH, N—CH$_3$, S, O |
| 229-232:A-D | 6-F, 4-F, 3-CH$_3$ | NH, N—CH$_3$, S, O |
| 233-236:A-D | 5-F, 4-F, 2-CH$_3$ | NH, N—CH$_3$, S, O |
| 237-240:A-D | 5-F, 4-F, 3-CH$_3$ | NH, N—CH$_3$, S, O |
| 241-244:A-D | 6-Cl, 5-Cl, 2-CH$_3$ | NH, N—CH$_3$, S, O |
| 245-248:A-D | 6-Cl, 5-Cl, 3-CH$_3$ | NH, N—CH$_3$, S, O |
| 249-252:A-D | 6-Cl, 4-Cl, 2-CH$_3$ | NH, N—CH$_2$, S, O |
| 253-256:A-D | 6-Cl, 4-Cl, 3-CH$_3$ | NH, N—CH$_3$, S, O |
| 257-260:A-D | 6-(CH$_3$—S—) | NH, N—CH$_3$, S, O |
| 261-264:A-D | 6-(CH$_3$—S—), 2-CH$_3$ | NH, N—CH$_3$, S, O |
| 265-268:A-D | 6-(CH$_3$—S—), 3-CH$_3$ | NH, N—CH$_3$, S, O |
| 269-272:A-D | 6-(CH$_3$—S(O)—) | NH, N—CH$_3$, S, O |
| 273-276:A-D | 6-(CH$_3$—S(O)—), 2-CH$_3$ | NH, N—CH$_3$, S, O |
| 277-280:A-D | 6-(CH$_3$—S(O)—), 3-CH$_3$ | NH, N—CH$_3$, S, O |
| 281-284:A-D | 7-F, 6-(CH$_3$—S) | NH, N—CH$_3$, S, O |
| 285-288:A-D | 5-F, 6-(CH$_3$—S) | NH, N—CH$_3$, S, O |
| 289-292:A-D | 4-F, 6-(CH$_3$—S) | NH, N—CH$_3$, S, O |
| 293-296:A-D | 6-CF$_3$ | NH, N—CH$_3$, S, O |
| 297-300:A-D | 6-CF$_3$, 2-CH$_3$ | NH, N—CH$_3$, S, O |
| 301-304:A-D | 6-CF$_3$, 3-CH$_3$ | NH, N—CH$_3$, S, O |
| 305-308:A-D | 6-[—CH(CH$_3$)COOH] | NH, N—CH$_3$, S, O |
| 309-312:A-D | 6-[—CH(CH$_3$)COOH], 2-CH$_3$ | NH, N—CH$_3$, S, O |
| 313-316:A-D | 6-[—CH(CH$_3$)COOH], 3-CH$_3$ | NH, N—CH$_3$, S, O |
| 317-320:A-D | 6-CH$_3$ | NH, N—CH$_3$, S, O |
| 321-324:A-D | 6-CH$_3$, 2-CH$_3$ | NH, N—CH$_3$, S, O |
| 325-328:A-D | 6-CH$_3$, 3-CH$_3$ | NH, N—CH$_3$, S, O |

UNSUBSTITUTED PARENT STRUCTURES FOR COMPOUNDS 329-656: A-D

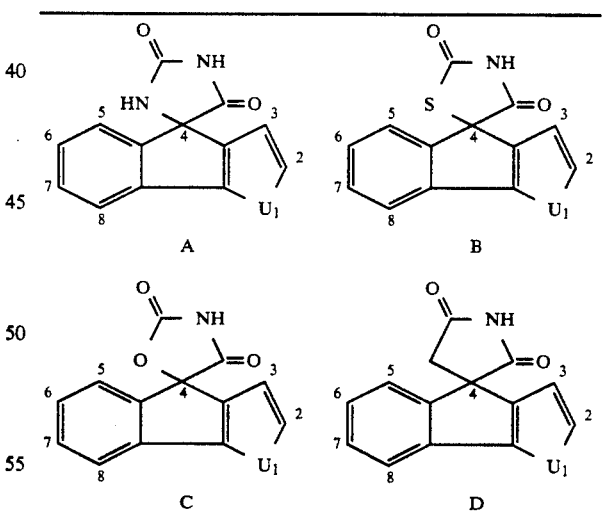

| Compound No. | Ring Substitution | U |
|---|---|---|
| 329-332:A-D | 7-F | NH, N—CH$_3$, S, O |
| 333-336:A-D | 6-F | NH, N—CH$_3$, S, O |
| 337-340:A-D | 5-F | NH, N—CH$_3$, S, O |
| 341-344:A-D | 8-F | NH, N—CH$_3$, S, O |
| 345-348:A-D | 7-F, 2-CH$_3$ | NH, N—CH$_3$, S, O |
| 349-352:A-D | 7-F, 3-CH$_3$ | NH, N—CH$_3$, S, O |
| 353-356:A-D | 6-F, 2-CH$_3$ | NH, N—CH$_3$, S, O |
| 357-360:A-D | 6-F, 3-CH$_3$ | NH, N—CH$_3$, S, O |
| 361-364:A-D | 5-F, 2-CH$_3$ | NH, N—CH$_3$, S, O |
| 365-368:A-D | 5-F, 3-CH$_3$ | NH, N—CH$_3$, S, O |
| 369-372:A-D | 8-F, 2-CH$_3$ | NH, N—CH$_3$, S, O |

-continued

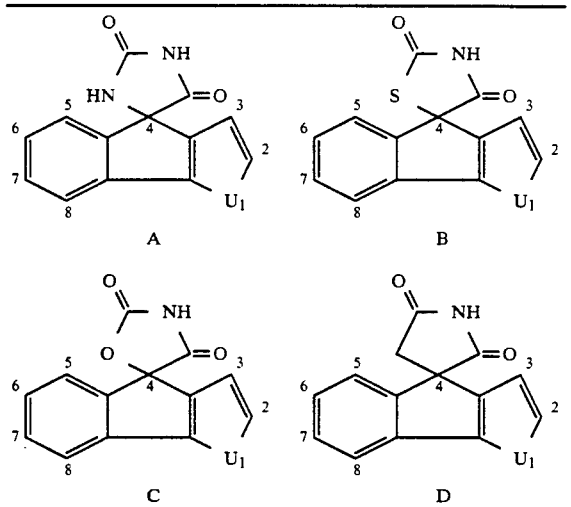

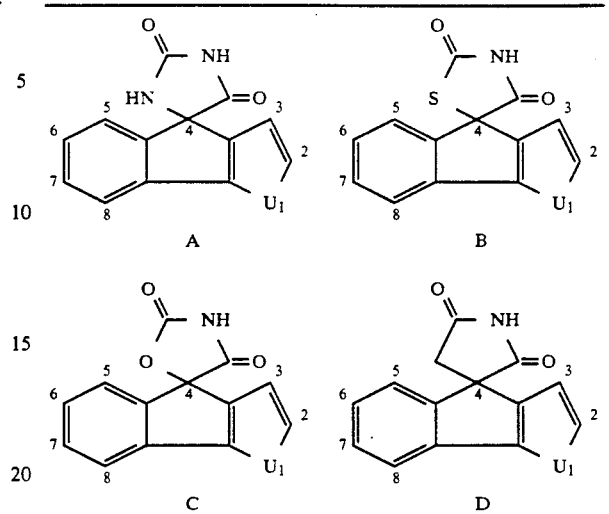

| Compound No. | Ring Substitution | U |
|---|---|---|
| 373-376:A-D | 8-F, 3-CH$_3$ | NH, N—CH$_3$, S, O |
| 377-380:A-D | 7-Cl | NH, N—CH$_3$, S, O |
| 381-384:A-D | 6-Cl | NH, N—CH$_3$, S, O |
| 385-388:A-D | 5-Cl | NH, N—CH$_3$, S, O |
| 389-392:A-D | 8-Cl | NH, N—CH$_3$, S, O |
| 393-396:A-D | 7-Cl, 2-CH$_3$ | NH, N—CH$_3$, S, O |
| 397-400:A-D | 7-Cl, 3-CH$_3$ | NH, N—CH$_3$, S, O |
| 401-404:A-D | 6-Cl, 2-CH$_3$ | NH, N—CH$_3$, S, O |
| 405-408:A-D | 6-Cl, 3-CH$_3$ | NH, N—CH$_3$, S, O |
| 409-412:A-D | 5-Cl, 2-CH$_3$ | NH, N—CH$_3$, S, O |
| 413-416:A-D | 5-Cl, 3-CH$_3$ | NH, N—CH$_3$, S, O |
| 417-420:A-D | 8-Cl, 2-CH$_3$ | NH, N—CH$_3$, S, O |
| 421-424:A-D | 8-Cl, 3-CH$_3$ | NH, N—CH$_3$, S, O |
| 425-428:A-D | 7-F, 6-F | NH, N—CH$_3$, S, O |
| 429-432:A-D | 7-F, 5-F | NH, N—CH$_3$, S, O |
| 433-436:A-D | 7-F, 8-F | NH, N—CH$_3$, S, O |
| 437-440:A-D | 6-F, 5-F | NH, N—CH$_3$, S, O |
| 441-444:A-D | 6-F, 8-F | NH, N—CH$_3$, S, O |
| 445-448:A-D | 5-F, 8-F | NH, N—CH$_3$, S, O |
| 449-452:A-D | 7-Cl, 6-Cl | NH, N—CH$_3$, S, O |
| 453-456:A-D | 7-Cl, 5-Cl | NH, N—CH$_3$, S, O |
| 457-460:A-D | 7-Cl, 8-Cl | NH, N—CH$_3$, S, O |
| 461-464:A-D | 6-Cl, 5-Cl | NH, N—CH$_3$, S, O |
| 465-468:A-D | 6-Cl, 8-Cl | NH, N—CH$_3$, S, O |
| 469-472:A-D | 5-Cl, 8-Cl | NH, N—CH$_3$, S, O |
| 473-476:A-D | 7-F, 6-Cl | NH, N—CH$_3$, S, O |
| 477-480:A-D | 7-F, 5-Cl | NH, N—CH$_3$, S, O |
| 481-484:A-D | 7-F, 8-Cl | NH, N—CH$_3$, S, O |
| 485-488:A-D | 6-F, 7-Cl | NH, N—CH$_3$, S, O |
| 489-492:A-D | 6-F, 5-Cl | NH, N—CH$_3$, S, O |
| 493-496:A-D | 6-F, 8-Cl | NH, N—CH$_3$, S, O |
| 497-500:A-D | 5-F, 7-Cl | NH, N—CH$_3$, S, O |
| 501-504:A-D | 5-F, 6-Cl | NH, N—CH$_3$, S, O |
| 505-508:A-D | 5-F, 8-Cl | NH, N—CH$_3$, S, O |
| 509-512:A-D | 8-F, 7-Cl | NH, N—CH$_3$, S, O |
| 513-516:A-D | 8-F, 6-Cl | NH, N—CH$_3$, S, O |
| 517-520:A-D | 8-F, 5-Cl | NH, N—CH$_3$, S, O |
| 521-524:A-D | 7-F, 6-F, 2-CH$_3$ | NH, N—CH$_3$, S, O |
| 525-528:A-D | 7-F, 5-F, 2-CH$_3$ | NH, N—CH$_3$, S, O |
| 529-532:A-D | 7-F, 8-F, 2-CH$_3$ | NH, N—CH$_3$, S, O |
| 533-536:A-D | 7-F, 6-F, 3-CH$_3$ | NH, N—CH$_3$, S, O |
| 537-540:A-D | 7-F, 5-F, 3-CH$_3$ | NH, N—CH$_3$, S, O |
| 541-544:A-D | 7-F, 8-F, 3-CH$_3$ | NH, N—CH$_3$, S, O |
| 545-548:A-D | 6-F, 5-F, 2-CH$_3$ | NH, N—CH$_3$, S, O |
| 549-552:A-D | 6-F, 8-F, 2-CH$_3$ | NH, N—CH$_3$, S, O |
| 553-556:A-D | 6-F, 5-F, 3-CH$_3$ | NH, N—CH$_3$, S, O |
| 557-560:A-D | 6-F, 8-F, 3-CH$_3$ | NH, N—CH$_3$, S, O |
| 561-564:A-D | 5-F, 8-F, 2-CH$_3$ | NH, N—CH$_3$, S, O |
| 565-568:A-D | 5-F, 8-F, 3-CH$_3$ | NH, N—CH$_3$, S, O |
| 569-572:A-D | 6-Cl, 5-Cl, 2-CH$_3$ | NH, N—CH$_3$, S, O |
| 573-576:A-D | 6-Cl, 5-Cl, 3-CH$_3$ | NH, N—CH$_3$, S, O |
| 577-580:A-D | 6-Cl, 8-Cl, 2-CH$_3$ | NH, N—CH$_3$, S, O |
| 581-584:A-D | 6-Cl, 8-Cl, 3-CH$_3$ | NH, N—CH$_3$, S, O |
| 585-588:A-D | 6-(CH$_3$—S—) | NH, N—CH$_3$, S, O |
| 589-592:A-D | 6-(CH$_3$—S—), 2-CH$_3$ | NH, N—CH$_3$, S, O |
| 593-596:A-D | 6-(CH$_3$—S—), 3-CH$_3$ | NH, N—CH$_3$, S, O |
| 597-600:A-D | 6-(CH$_3$—S(O)—) | NH, N—CH$_3$, S, O |
| 601-604:A-D | 6-(CH$_3$—S(O)—), 2-CH$_3$ | NH, N—CH$_3$, S, O |
| 605-608:A-D | 6-(CH$_3$—S(O)—), 3-CH$_3$ | NH, N—CH$_3$, S, O |
| 609-612:A-D | 7-F, 6-(CH$_3$—S) | NH, N—CH$_3$, S, O |
| 613-616:A-D | 5-F, 6-(CH$_3$—S) | NH, N—CH$_3$, S, O |
| 617-620:A-D | 8-F, 6-(CH$_3$—S) | NH, N—CH$_3$, S, O |
| 621-624:A-D | 6-CF$_3$ | NH, N—CH$_3$, S, O |
| 625-628:A-D | 6-CF$_3$, 2-CH$_3$ | NH, N—CH$_3$, S, O |
| 629-632:A-D | 6-CF$_3$, 3-CH$_3$ | NH, N—CH$_3$, S, O |
| 633-636:A-D | 6-[—CH(CH$_3$)COOH] | NH, N—CH$_3$, S, O |
| 637-640:A-D | 6-[—CH(CH$_3$)COOH], 2-CH$_3$ | NH, N—CH$_3$, S, O |
| 641-644:A-D | 6-[—CH(CH$_3$)COOH], 3-CH$_3$ | NH, N—CH$_3$, S, O |
| 645-648:A-D | 6-CH$_3$ | NH, N—CH$_3$, S, O |
| 649-652:A-D | 6-CH$_3$, 2-CH$_3$ | NH, N—CH$_3$, S, O |
| 653-656:A-D | 6-CH$_3$, 3-CH$_3$ | NH, N—CH$_3$, S, O |

UNSUBSTITUTED PARENT STRUCTURES FOR COMPOUNDS 657-706: A-D

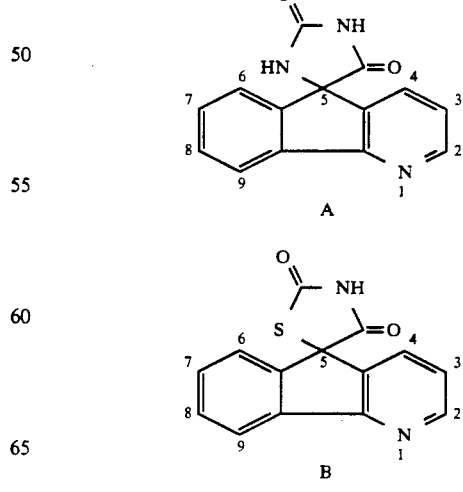

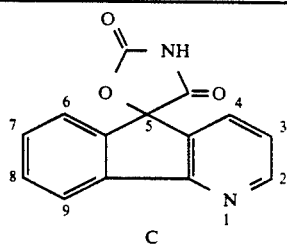

C

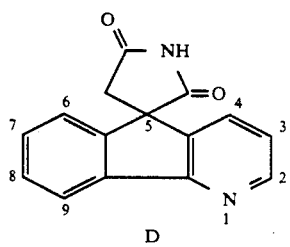

D

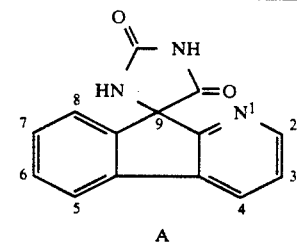

A

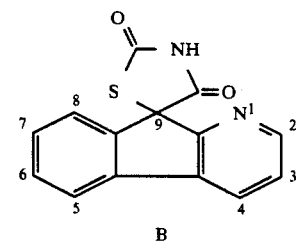

B

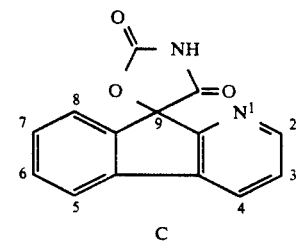

C

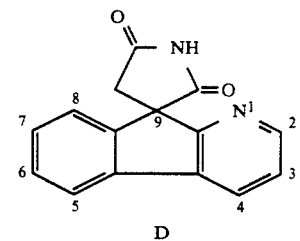

D

| Compound No. | Ring Substitution |
|---|---|
| 657:A-D | 6-F |
| 658:A-D | 7-F |
| 659:A-D | 8-F |
| 660:A-D | 9-F |
| 661:A-D | 3-F |
| 662:A-D | 6-F, 3-F |
| 663:A-D | 7-F, 3-F |
| 664:A-D | 8-F, 3-F |
| 665:A-D | 9-F, 3-F |
| 666:A-D | 6-Cl |
| 667:A-D | 7-Cl |
| 668:A-D | 8-Cl |
| 669:A-D | 9-Cl |
| 670:A-D | 6-Cl, 3-F |
| 671:A-D | 7-Cl, 3-F |
| 672:A-D | 8-Cl, 3-F |
| 673:A-D | 9-Cl, 3-F |
| 674:A-D | 6-F, 7-F |
| 675:A-D | 6-F, 8-F |
| 676:A-D | 6-F, 9-F |
| 677:A-D | 7-F, 8-F |
| 678:A-D | 7-F, 9-F |
| 679:A-D | 8-F, 9-F |
| 680:A-D | 3-F, 7-F, 8-F |
| 681:A-D | 7-($CH_3-S$) |
| 682:A-D | 7-($CH_3-S(O)-$) |
| 683:A-D | 7-[—CH($CH_3$)COOH] |
| 684:A-D | 7-[—CH($CH_3$)COOH], 3-$CH_3$ |
| 685:A-D | 7-[—CH($CH_3$)COOH], 2-$CH_3$ |
| 686:A-D | 7-[—CH($CH_2$)COOH], 4-$CH_3$ |
| 687:A-D | 6-[—CH($CH_3$)COOH] |
| 687:A-D | 6-[—CH($CH_3$)COOH], 3-$CH_3$ |
| 688:A-D | 6-[—CH($CH_3$)COOH], 2-$CH_3$ |
| 689:A-D | 6-[—CH($CH_3$)COOH], 4-$CH_3$ |
| 690:A-D | 7-$CH_3$ |
| 691:A-D | 7-($CH_3-O$) |
| 692:A-D | 7-$CF_3$ |
| 693:A-D | 7-COOH |
| 694:A-D | 7-$CONH_2$ |
| 695:A-D | 6-$CH_3$COOH |
| 696:A-D | 6-$CH_2$COOH, 3-$CH_3$ |
| 697:A-D | 6-$CH_2$COOH, 2-$CH_3$ |
| 698:A-D | 6-$CH_2$COOH, 4-$CH_3$ |
| 699:A-D | 6-COOH |
| 700:A-D | 6-$CH_3-NH_2$ |
| 701:A-D | 7-$CH_2$COOH |
| 702:A-D | 7-$CH_2$COOH, 3-$CH_3$ |
| 703:A-D | 7-$CH_2$COOH, 2-$CH_3$ |
| 704:A-D | 7-$CH_2$COOH, 4-$CH_3$ |
| 705:A-D | 7-COOH, 3-$CH_3$ |
| 706:A-D | 7-$CH_2-NH_2$ |

| Compound No. | Ring Substitution |
|---|---|
| 707:A-D | 8-F |
| 708:A-D | 7-F |
| 709:A-D | 6-F |
| 710:A-D | 5-F |
| 711:A-D | 7-Cl |
| 712:A-D | 5-F, 6-F |
| 713:A-D | 5-F, 7-F |
| 714:A-D | 5-F, 8-F |
| 715:A-D | 6-F, 7-F |
| 716:A-D | 6-F, 8-F |
| 717:A-D | 7-F, 8-F |
| 718:A-D | 7-($CH_3-S$) |
| 719:A-D | 7-($CH_3-S(O)-$) |
| 720:A-D | 7-COOH |
| 721:A-D | 7-$CH_3$ |
| 722:A-D | 7-$CF_3$ |
| 723:A-D | 7-[CH($CH_2$)COOH] |
| 724:A-D | 7-[CH($CH_2$)COOH], 2-$CH_3$ |
| 725:A-D | 7-[CH($CH_2$)COOH], 3-$CH_3$ |
| 726:A-D | 7-[CH($CH_2$)COOH], 4-$CH_3$ |
| 727:A-D | 6-[CH($CH_2$)COOH], 2-$CH_3$ |
| 728:A-D | 6-[CH($CH_2$)COOH], 3-$CH_3$ |
| 729:A-D | 6-[CH($CH_2$)COOH], 4-$CH_3$ |
| 730:A-D | 6-[CH($CH_2$)COOH], 5-$CH_3$ |

UNSUBSTITUTED PARENT STRUCTURES FOR PARENT COMPOUNDS 731–766:A–D

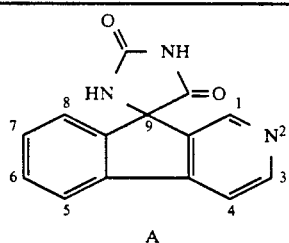

A

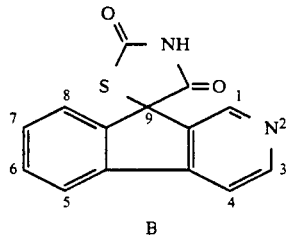

B

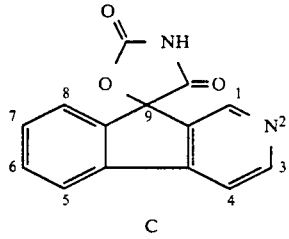

C

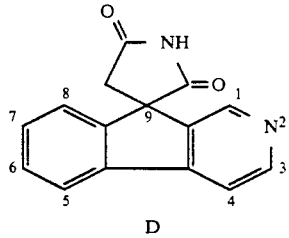

D

| Compound No. | Ring Substitution |
|---|---|
| 731:A-D | 8-F |
| 732:A-D | 7-F |
| 733:A-D | 6-F |
| 734:A-D | 5-F |
| 735:A-D | 7-Cl |
| 736:A-D | 5-F, 6-F |
| 737:A-D | 5-F, 7-F |
| 738:A-D | 5-F, 8-F |
| 739:A-D | 6-F, 7-F |
| 740:A-D | 6-F, 8-F |
| 741:A-D | 7-F, 8-F |
| 742:A-D | 7-(CH$_2$—S—) |
| 743:A-D | 7-(CH$_2$S(O)—) |
| 744:A-D | 7-COOH |
| 745:A-D | 7-CH$_3$ |
| 746:A-D | 7-CF$_3$ |
| 747:A-D | 7-[CH(CH$_3$)COOH] |
| 748:A-D | 7-[CH(CH$_3$)COOH], 1-CH$_3$ |
| 749:A-D | 7-[CH(CH$_3$)COOH], 3-CH$_3$ |
| 750:A-D | 7-[CH(CH$_3$)COOH], 4-CH$_3$ |
| 751:A-D | 6-[CH(CH$_2$)COOH] |
| 752:A-D | 6-[CH(CH$_2$)COOH], 1-CH$_3$ |
| 753:A-D | 6-[CH(CH$_2$)COOH], 3-CH$_3$ |
| 754:A-D | 6-[CH(CH$_2$)COOH], 4-CH$_3$ |
| 755:A-D | 7-CONH$_2$ |
| 756:A-D | 6-CONH$_2$ |
| 757:A-D | 7-CH$_2$COOH |

-continued

| | |
|---|---|
| 758:A-D | 7-CH$_2$COOH, 1-CH$_3$ |
| 759:A-D | 7-CH$_2$COOH, 3-CH$_3$ |
| 760:A-D | 7-CH$_2$COOH, 4-CH$_3$ |
| 761:A-D | 6-CH$_2$COOH |
| 762:A-D | 6-CH$_2$COOH, 1-CH$_3$ |
| 763:A-D | 6-CH$_2$COOH, 3-CH$_3$ |
| 764:A-D | 6-CH$_2$COOH, 4-CH$_3$ |
| 765:A-D | 6-COOH |
| 766:A-D | 6-Cl |

UNSUBSTITUTED PARENT STRUCTURES FOR COMPOUNDS 767–792:A–D

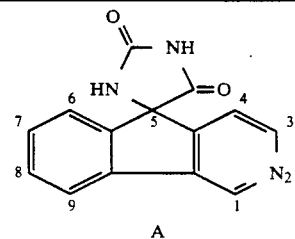

A

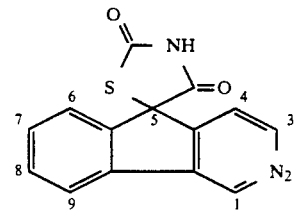

B

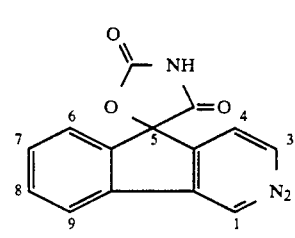

C

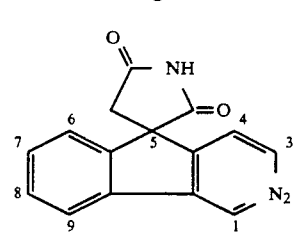

D

| Compound No. | Ring Substitution |
|---|---|
| 767:A-D | 9-F |
| 768:A-D | 8-F |
| 769:A-D | 7-F |
| 770:A-D | 6-F |
| 771:A-D | 7-Cl |
| 772:A-D | 8-Cl |
| 773:A-D | 7-(CH$_2$—S) |
| 774:A-D | 7-(CH$_3$—S(O)—) |
| 775:A-D | 7-[CH(CH$_3$)COOH] |
| 776:A-D | 6-[CH(CH$_3$)COOH] |
| 777:A-D | 7-COOH |
| 778:A-D | 7-CONH$_2$ |
| 779:A-D | 7-CF$_3$ |
| 780:A-D | 7-CH$_3$COOH |

-continued

| | |
|---|---|
| 781:A-D | 8-CH₃COOH |
| 782:A-D | 7-CH₃COOC₂H₅ |
| 783:A-D | 8-CH₃COOC₂H₅ |
| 784:A-D | 7-F, 8-F |
| 785:A-D | 7-Cl, 8-Cl |
| 786:A-D | 7-CH₃ |
| 787:A-D | 7-CH₂—NH₃ |
| 788:A-D | 7-NO₃ |
| 789:A-D | 8-NO₃ |
| 790:A-D | 7-CH₃—OH |
| 791:A-D | 8-COOH |
| 792:A-D | 8-CONH₂ |

UNSUBSTITUTED PARENT STRUCTURES FOR COMPOUNDS 793–847:A–D

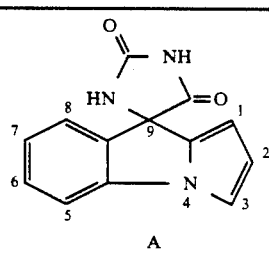

A

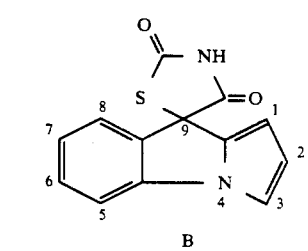

B

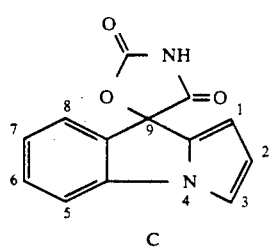

C

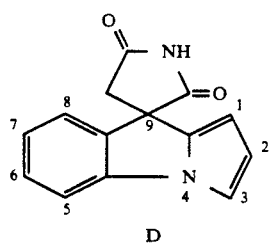

D

| Compound No. | Ring Substitution |
|---|---|
| 793:A-D | 8-F |
| 794:A-D | 7-F |
| 795:A-D | 6-F |
| 796:A-D | 5-F |
| 797:A-D | 8-F, 1-CH₃ |
| 798:A-D | 8-F, 2-CH₃ |
| 799:A-D | 8-F, 3-CH₃ |
| 800:A-D | 7-F, 1-CH₃ |
| 801:A-D | 7-F, 2-CH₃ |
| 802:A-D | 7-F, 3-CH₃ |
| 803:A-D | 6-F, 1-CH₃ |

-continued

| | |
|---|---|
| 804:A-D | 6-F, 2-CH₃ |
| 805:A-D | 6-F, 3-CH₃ |
| 806:A-D | 5-F, 1-CH₃ |
| 807:A-D | 5-F, 2-CH₃ |
| 808:A-D | 5-F, 3-CH₃ |
| 809:A-D | 7-Cl |
| 810:A-D | 7-Cl, 1-CH₃ |
| 811:A-D | 7-Cl, 2-CH₃ |
| 812:A-D | 7-Cl, 3-CH₃ |
| 813:A-D | 7-(CH₂—S—) |
| 814:A-D | 7-(CH₂—S—), 1-CH₃ |
| 815:A-D | 7-(CH₂—S—), 2-CH₃ |
| 816:A-D | 7-(CH₂—S—), 3-CH₃ |
| 817:A-D | 7-[CH₃—S(O)—] |
| 818:A-D | 7-[CH₃—S(O)—], 1-CH₃ |
| 819:A-D | 7-[CH₃—S(O)—], 2-CH₃ |
| 820:A-D | 7-[CH₃—S(O)—], 3-CH₃ |
| 821:A-D | 6-F, 7-F |
| 822:A-D | 7-Cl, 6-F |
| 823:A-D | 7-[CH(CH₃)COOH] |
| 824:A-D | 7-[CH(CH₂)COOH], 1-CH₃ |
| 825:A-D | 7-[CH(CH₂)COOH], 2-CH₃ |
| 826:A-D | 7-[CH(CH₂)COOH], 3-CH₃ |
| 827:A-D | 6-[CH(CH₂)COOH] |
| 828:A-D | 6-[CH(CH₂)COOH], 1-CH₃ |
| 829:A-D | 6-[CH(CH₂)COOH], 2-CH₃ |
| 830:A-D | 6-[CH(CH₂)COOH], 3-CH₃ |
| 831:A-D | 6-CH₂COOH |
| 832:A-D | 6-CH₂COOH, 1-CH₃ |
| 833:A-D | 6-CH₂COOH, 2-CH₃ |
| 834:A-D | 6-CH₂COOH, 3-CH₃ |
| 835:A-D | 7-CH₃COOH |
| 836:A-D | 7-CH₃COOH, 1-CH₃ |
| 837:A-D | 7-CH₃COOH, 2-CH₃ |
| 838:A-D | 7-CH₃COOH, 3-CH₃ |
| 839:A-D | 6-Cl |
| 840:A-D | 6-COOH |
| 841:A-D | 6-CONH₂ |
| 842:A-D | 7-COOH |
| 843:A-D | 7-CONH₃ |
| 844:A-D | 6-OCH₃ |
| 845:A-D | 3-Cl |
| 846:A-D | 6-CH₂NH₃ |
| 847:A-D | 7-CH₂NH₃ |

UNSUBSTITUTED PARENT STRUCTURE FOR COMPOUNDS 848–876:A–D

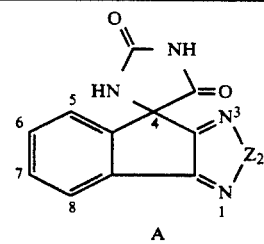

A

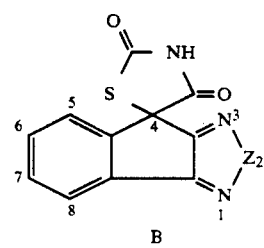

B

-continued

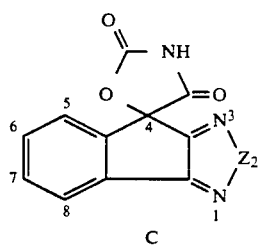

C

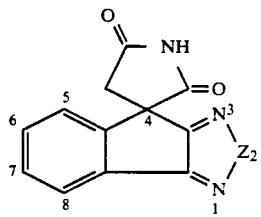

D

| Compound No. | Ring Substitution | Z |
|---|---|---|
| 848–849:A–D | 6-F | O, S |
| 850–851:A–D | 7-F | O, S |
| 852–853:A–D | 6-Cl | O, S |
| 854–855:A–D | 7-Cl | O, S |
| 856–857:A–D | 6-COOH | O, S |
| 858–859:A–D | 6-(CH$_3$—S) | O, S |
| 860–861:A–D | 6-[CH(CH$_3$)COOH] | O, S |
| 862–863:A–D | 7-[CH(CH$_3$)COOH] | O, S |
| 864–865:A–D | 6-CH$_3$COOH | O, S |
| 866–867:A–D | 7-CH$_3$COOH | O, S |
| 868–869:A–D | 7-COOH | O, S |
| 870–871:A–D | 6-CONH$_3$ | O, S |
| 872–873:A–D | 7-CONH$_3$ | O, S |
| 874–875:A–D | 6-F, 7-F | O, S |

UNSUBSTITUTED PARENT STRUCTURE FOR COMPOUNDS 877–940:A–D

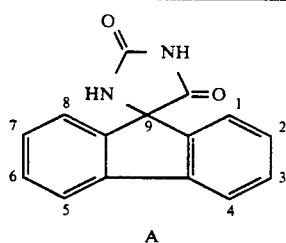

A

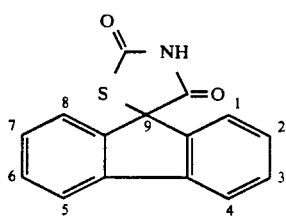

B

-continued

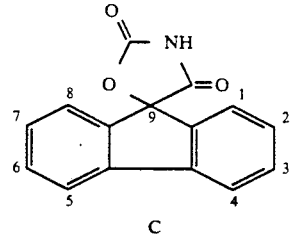

C

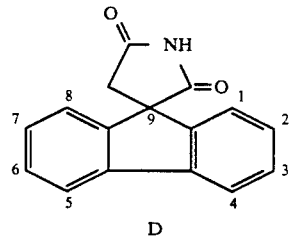

D

| Compound No. | Ring Substitution |
|---|---|
| 877:A–D | 1-F |
| 878:A–D | 2-F |
| 879:A–D | 3-F |
| 880:A–D | 4-F |
| 881:A–D | 1-F, 5-F |
| 882:A–D | 1-F, 6-F |
| 883:A–D | 1-F, 7-F |
| 884:A–D | 1-F, 8-F |
| 885:A–D | 2-F, 5-F |
| 886:A–D | 2-F, 6-F |
| 887:A–D | 2-F, 7-F |
| 888:A–D | 3-F, 5-F |
| 889:A–D | 3-F, 6-F |
| 890:A–D | 4-F, 5-F |
| 891:A–D | 2-Cl |
| 892:A–D | 2-Cl, 5-F |
| 893:A–D | 2-Cl, 6-F |
| 894:A–D | 2-Cl, 7-F |
| 895:A–D | 2-Cl, 8-F |
| 896:A–D | 2-F, 3-F, 7-F |
| 897:A–D | 2-F, 7-CH$_3$ |
| 898:A–D | 2-F, 7-(CH$_3$—S) |
| 899:A–D | 2-F, 7-(CH$_3$—S(O)) |
| 900:A–D | 2-F, 7-(CH$_3$—SO$_2$—) |
| 901:A–D | 2-Cl, 7-(CH$_3$—S) |
| 902:A–D | 2-Cl, 7-(CH$_3$—S(O)) |
| 903:A–D | 2-Cl, 7-(CH$_3$—SO$_3$—) |
| 904:A–D | 2-F, 7-(CH$_3$O—) |
| 905:A–D | 7-F, 2-COOH |
| 906:A–D | 6-F, 2-COOH |
| 907:A–D | 7-F, 3-COOH |
| 908:A–D | 6-F, 3-COOH |
| 909:A–D | 2-F, 2-[CH(CH$_3$)COOH] |
| 910:A–D | 2-Cl, 2-[CH(CH$_3$)COOH] |
| 911:A–D | 2-F, 2-[CH(CH$_3$)COOH] |
| 912:A–D | 2-Cl, 2-[CH(CH$_3$)COOH] |
| 913:A–D | 2-(CH$_3$—S), 7-[CH(CH$_3$)COOH] |
| 914:A–D | 2-[CH$_3$—S(O)], 7-[CH(CH$_3$)COOH] |
| 915:A–D | 2-(CH$_3$—S), 6-[CH(CH$_3$)COOH] |
| 916:A–D | 2-[CH$_3$—S(O)], 6-[CH(CH$_3$)COOH] |
| 917:A–D | 7-F, 2-CONH$_2$ |
| 918:A–D | 7-Cl, 2-CONH$_2$ |
| 919:A–D | 2-F, 3-F, 7-(CH$_3$—S) |
| 920:A–D | 2-F, 3-F, 7-[CH$_3$S(O)] |
| 921:A–D | 2-F, 7-CF$_3$ |
| 922:A–D | 2-F, 7-OH |
| 923:A–D | 2-F, 6-OH |
| 924:A–D | 2-F, 5-OH |
| 925:A–D | 2-F, 7-(CH$_3$—O—) |
| 926:A–D | 2-COOH, 6-F, 7-F |
| 927:A–D | 3-COOH, 6-F, 7-F |
| 928:A–D | 2-(CH$_3$—S), 3-F |
| 929:A–D | 2-(CH$_2$—S), 4-F |
| 930:A–D | 2-F, 3-F, 7-(CH$_2$—S) |
| 931:A–D | 2-F, 3-F, 7-[CH$_2$—S(O)—] |

-continued

| | |
|---|---|
| 932:A-D | 2-F, 3-(CH₂—S—), 7-F |
| 933:A-D | 2-F, 3-[CH₂S(O)—], 7-F |
| 934:A-D | 1-F, 7-NO₂ |
| 935:A-D | 2-F, 7-NO₂ |
| 936:A-D | 3-F, 7-NO₂ |
| 937:A-D | 4-F, 7-NO₂ |
| 938:A-D | 2-[CH₂(CH₃)COOH] |
| 939:A-D | 2-CH₂COOH |
| 940:A-D | 2-CH₃COOH, 7-F |

EXAMPLE XX

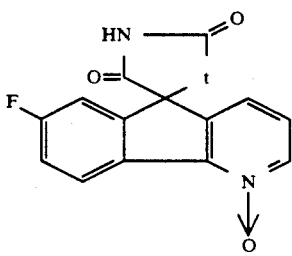

t = CH₂, O, NH

Preferred derivatives from Example XIX may be oxidized in accordance with Method VI to yield the corresponding N-oxides. Similarly, other N-oxides are prepared from other spiro-tricyclic aromatic azine derivatives of the present invention.

Alternatively, an indeopyridine or indenopyridine ketone may be oxidized in accordance with Method V to the corresponding N-oxide prior to spiro derivatization according to Methods I, III or IV.

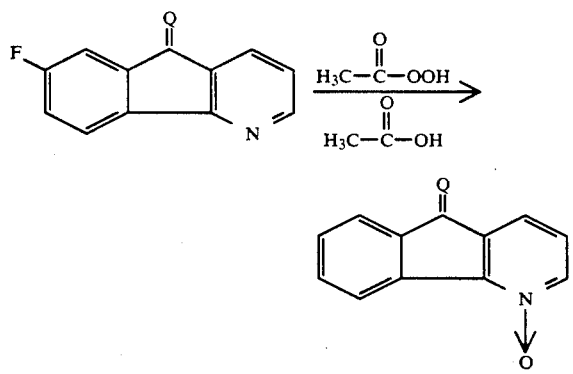

Q = H₂, O

EXAMPLE XXI

The sodium salt of spiro-(2-fluoro-9H-fluoren-9,5'-thiazolidine)-2',4'-dione, spiro-(6-fluoro-9H-pyrrolol[1,2-a]indol-9,4'-imidazolidine)-2,4'-dione, spiro-(7-fluoro-5H-indeno[1,2-b]pyridin-5,4'-imidazolidine)-2',5'-dione or any of their related spiro tricyclic congeners which are the subject of the present invention are prepared by dissolving any of said compounds in water containing an equivalent amount in moles of sodium hydroxide and then freeze-drying the mixture. In this way, the desired alkali metal salt of the spiro-hydantoin, spiro-thiazolidinedione, spiro-oxazolidinedione or spiro-succinimide can be prepared. In those cases where the aromatic substituents contain carboxylic acid moieties (e.g., isopropanoic acid substituent), one equivalent of base will yield the corresponding sodium carboxylate salt. In such cases as the aforementioned, two mole equivalents will yield the disodium salt. By this method, the desired alkali metal salt is obtained as an amorphous powder which is soluble in water.

In like manner, the potassium and lithium salts are analogously prepared, as are the alkali metal salts of all other spiro-tricycle compounds of this invention which are reported in Examples I–XVII and XIX, respectively.

EXAMPLE XXII

The calcium salt of spiro-(2-fluoro-9H-fluoren-9,5'-thiazolidine)-2',4'-dione is prepared by dissolving said compound in water containing an equivalent amount in moles of calcium hydroxide and then freeze-drying the mixture. The corresponding magnesium salt is also prepared in this manner, as are all other alkaline-earth metal salts not only of this particular compound, but also those spiro-tricyclic analogs previously described in Examples I–XVII and XIX, respectively.

EXAMPLE XXIII

The hydrogen chloride salt of spiro-(7-fluoro-9H-indeno[2,1-c]pyridin-9,4'-imidazolidine)-2',5'-dione, spiro-(7-fluoro-5H-indeno[1,2-b]pyridine-5,4'-imidazolidine)-2',5'-dione or spiro-(7-fluoro-5H-indeno[1,2-b]-5,5'-thiazolidine)-2',4'-dione in 1.0 to 1.5 equivalent amount of 1N to 10N hydrochloric acid and then freeze-drying the mixture in a manner to remove excess hydrochloric acid. By this method the aforementioned and related spiro-tricyclic azine analogs, previously described in Example XIX, and prepared as hydrogen chloride salt powders which are soluble in water.

EXAMPLE XXIV

A dry solid pharmaceutical composition is prepared by mixing the following materials together in the proportions by weight specified:

| | |
|---|---|
| Sprio-(2-fluoro-9,5'-thiazolidine)-2',4'-dione | 50 |
| Sodium Citrate | 20 |
| Alginic Acid | 5 |
| Polyvinylpyrrolidone | 15 |
| Magnesium Stearate | 5 |

The dry composition is thoroughly blended, tablets are punched from the resulting mixture, each tablet being of such size that it contains 100 mg of the active ingredient. Other tablets are also prepared in a likewise manner containing 10, 25 and 200 mg of active ingredient, respectively, by merely using an appropriate quantity by weight of the spiro-thiazolidinedione in each case. Likewise other related examples of spiro-thiazoidinediones, spiro-imidazolidinediones, spiro-oxazolidinediones, spiro-succinimides can be formulated as tablets on a respective weight proportion.

EXAMPLE XXV

A dry solid pharmaceutical composition is prepared by combining the following materials together in the weight proportions indicated below:

| | |
|---|---|
| Spiro-(7-fluoro-5H-indeno[1,2-b]pyridin-5,4'-imidazolidine)-2',5'-dione | 50 |
| Calcium Carbonate | 20 |

| Polyethylene glycol, Average Molecular Weight 25,000 | 30 |

The dried solid mixture is thoroughly mixed until uniform in composition. The powdered product is then used to fill soft elastic and hard-gelatin capsules so as to provide capsules containing 200 mg of the active ingredient.

EXAMPLE XXVI

The following spiro-tricyclic compounds of the Examples and Preparations previously described were tested for their ability to inhibit or reduce aldose reductase enzyme activity. The procedure for the aldose reductase enzyme activity inhibition test is described in the following publications:

a) P. F. Kador, L. O. Merola and J. H. Kinoshita, *Docum. Ophthal. Proc. Series*, 18, 117–124 (1979);

b) P. F. Kador, J. H. Kinoshita, W. H. Tung and L. T. Chylack, Jr., *Invest. Ophthalmol. Vis. Sci.*, 19, 980–982 (1980);

c) P. F. Kador, D. Carper and J. H. Kinoshita, *Analytical Biochemistry*, 114, 53–58 (1981).

Wherein the assay mixture used in the tests containing 0.1M potassium phosphate buffer, pH 6.2, 0.2 mM nictoinamide adenine dinucleotide phosphate (NADPH), 10 mM D,L-glyceraldehyde, and an appropriate volume of the enzyme preparation, thermostated at 25° C. in the cell compartment of a spectrophotometer. These conditions are identical to those published in references (a), (b) and (c), except that a larger NADPH concentration was employed. This insured a linear reaction rate for longer time periods since one product of the reaction, NADP+, markedly inhibits the enzyme. The control sample contained no added inhibitor. In order to measure aldose reductase inhibition activity, varying concentrations of the inhibitor examples set forth below were added to the standard incubation mixture. The control, containing the enzyme and NADPH, gave a very small, but measurable rate; thus, it served as the blank against which to measure the glyceraldehyde-dependent rate of NADPH oxidation. The tests were conducted with human placental aldose reductase enzyme. The results of the tests are the product of multiple assays. The IC50 data for each compound is expressed below in terms of concentration of compound required to inhibit 50% human placental aldose reductase enzyme activity. A test compound is considered active if it inhibits or reduces human aldose reductase activity at $1 \times 10^{-4}$M concentration or less. The following list is provided as a representative sample of the biological activity of the spiro-tricyclic derivatives of the present invention.

A. d,1-Spiro-(2-fluoro-9H-fluoren-9,4'-imidazolidine)-2',5'-dione

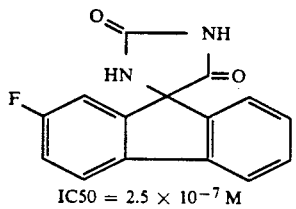

IC50 = $2.5 \times 10^{-7}$ M

B. Spiro-(2,7-Difluoro-9H-fluoren-9,4'-imidazolidine)-2',5'-dione

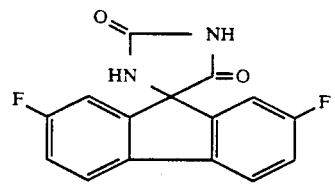

IC50 = $8.9 \times 10^{-8}$ M

C. d,1-Spiro-(2-fluoro-9H-fluoren-9,5'-thiazolidine)-2',4'-dione

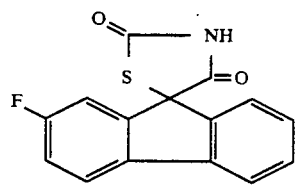

IC50 = $6.8 \times 10^{-8}$ M

D. Spiro-(2,7-difluoro-9H-fluoren-9,5'-thiazolidine)-2',4'-dione

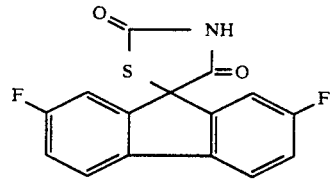

IC50 = $6.2 \times 10^{-8}$ M

E. d,1-Spiro-(5H-indeno[1,2-b]pyridine-5,3'-succinimide)

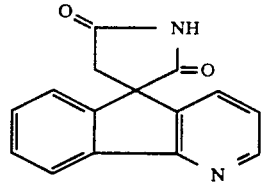

IC50 = $1.79 \times 10^{-6}$ M

F. d,1-Spiro-(2-fluoro-9H-fluoren-9,3'-succinimide)

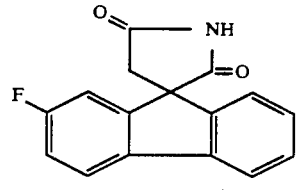

IC50 = $2.87 \times 10^{-7}$ M

G. Spiro-(9H-fluoren-9,3'-succinimide)

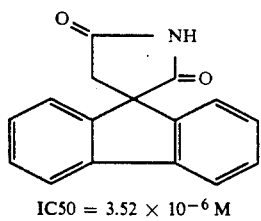

IC50 = 3.52 × 10⁻⁶ M

H. d,1-Spiro-(2-chloro-7-fluoro-9H-fluoren-9,4'-imidazolidine)-2',5'-dione

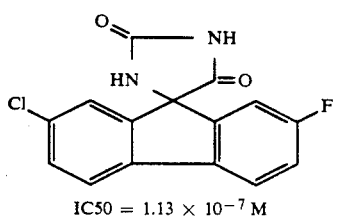

IC50 = 1.13 × 10⁻⁷ M

I. d,1-Spiro-(9H-pyrrolol[1,2-a]indol-9,4'-imidazolidine-2',4'-dione

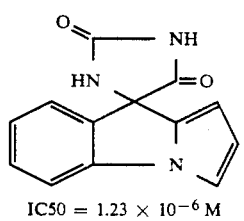

IC50 = 1.23 × 10⁻⁶ M

J. d,1-Spiro-(7-nitro-5H-indeno[1,2-b]pyridin-5,4'-imidazolidine)-2',5'-dione

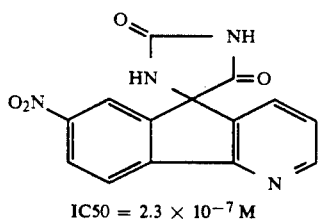

IC50 = 2.3 × 10⁻⁷ M

K. d,1-Spiro-(7-bromo-5H-indeno[1,2-b]pyridin-5,4'-imidazolidine)-2',5'-dione

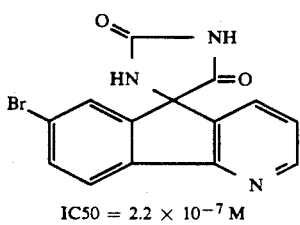

IC50 = 2.2 × 10⁻⁷ M

L. d,1-Spiro-(2-chloro-9H-fluoren-9,4'imidazolidine)-2',5'-dione

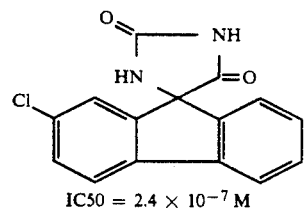

IC50 = 2.4 × 10⁻⁷ M

M. Spiro-(9H-fluoren-9,5'-thiazolidine)-2',4'-dione

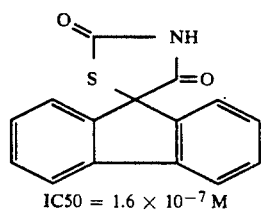

IC50 = 1.6 × 10⁻⁷ M

N. Spiro-(9H-fluoren-9,5'-oxazolidine)-2',4'-dione

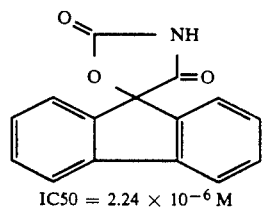

IC50 = 2.24 × 10⁻⁶ M

O. d,1-Spiro-(2-fluoro-9H-fluoren-9,5'-oxazolidine)-2',4'-dione

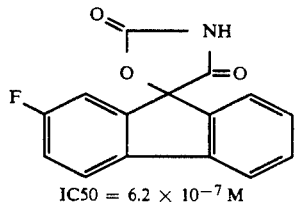

IC50 = 6.2 × 10⁻⁷ M

P. d,1-Spiro-(9H-indeno[2,1-c]pyridin-9,4'-imidazolidine)-2',5'-dione

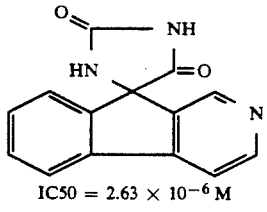

IC50 = 2.63 × 10⁻⁶ M

Q. d,1-Spiro-(4H-indeno[1,2-b]thiophen-4,4'-imidazolidine)-2',5'-dione

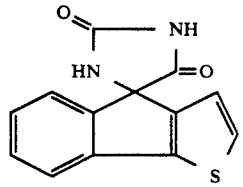

-continued
IC50 = 4.33 × 10⁻⁶ M

R. d,1-Spiro-(8H-indeno[2,1-b]thiophen-8,4'-imidazolidine)-2',5'-dione

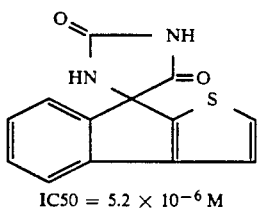

IC50 = 5.2 × 10⁻⁶ M

S. d,1-Spiro-(5H-indeno[1,2-b]pyridin-5,4'-imidazolidine)-2',5'-dione

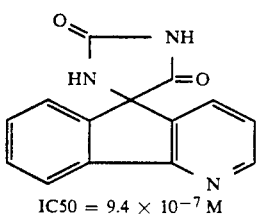

IC50 = 9.4 × 10⁻⁷ M

Research (Kador, Merola and Kinoshite, *Docum. Ophthal. Proc. Series*, 18 (1979) 117) has indicated that the evaluation of aldose reductase inhibitors for potential human chemotherapy may require testing with human aldose reductase. There are species-linked differences in the susceptibility for inhibition of aldose reductase. For example, rat lens aldose reductase behaves differently from human placental aldose reductase with respect to inhibition by synthetic chemical inhibitors.

EXAMPLE XXVII

According to the procedures of Kador, Merola and Kinoshite, *Docum. Ophthal. Proc. Series*, 18 (1979) 117 and Kador and Sharpless, *Biophysical Chemistry*, 8 (1978) 81 the inhibition exerted by examples of the present invention where evaluated against rat lens aldose reductase. Otherwise, the inhibitor assay is identical to that employed against human aldose reductase in Example XXVI. Representative rat lens aldose reductase inhibition is presented in terms of the concentration of test compound required to reduce rat lens aldose reductase enzyme activity by 50%. A test compound is considered active if it inhibits or reduces rat lens aldose reductase activity at $1 \times 10^{-4}$M concentration or less.

A. Spiro-(2-fluoro-9H-fluoren-9,4'-imidazolidine)-2',5'-dione

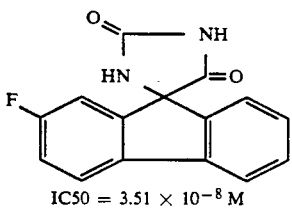

IC50 = 3.51 × 10⁻⁸ M

B. Spiro-(2,7-difluoro-9H-fluoren-9,4'-imidazolidine)-2',5'-dione

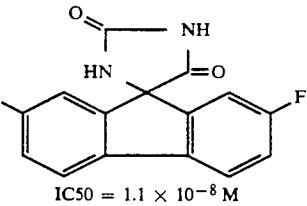

IC50 = 1.1 × 10⁻⁸ M

C. Spiro-(2-fluoro-9H-fluoren-9,5'-thiazolidine)-2',4'-dione

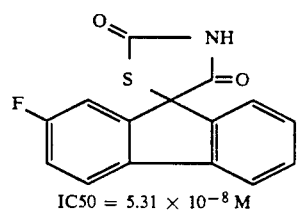

IC50 = 5.31 × 10⁻⁸ M

D. Spiro-(2,7-difluoro-9H-fluoren-9,5'-thiazolidine)-2',4'-dione

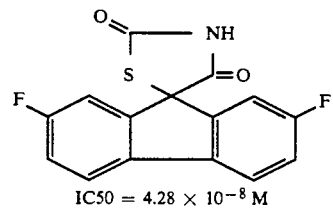

IC50 = 4.28 × 10⁻⁸ M

E. Spiro-(2-fluoro-9H-fluoren-9,3'-succinimide)

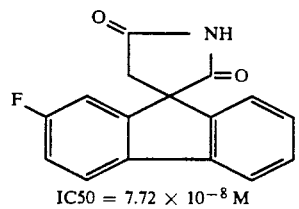

IC50 = 7.72 × 10⁻⁸ M

F. Spiro-(9H-fluoren-9,5'-thiazolidine)-2',4'-dione

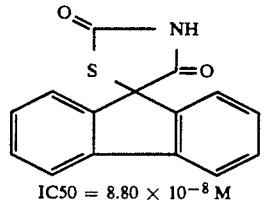

IC50 = 8.80 × 10⁻⁸ M

G. Spiro-(2-methylthio-9H-fluoren-9,4'-imidazolidine)-2',5'-dione

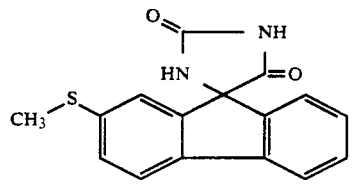

-continued

IC50 = 7.5 × 10⁻⁸ M

H. Spiro-(5H-indeno[1,2-b]pyridin-5,4'-imidazolidine)-2',5'-dione

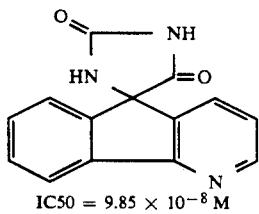

IC50 = 9.85 × 10⁻⁸ M

I. Spiro-(2-fluoro-9H-fluoren-9,5'-oxazolidine)-2',4'-dione

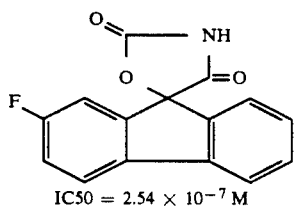

IC50 = 2.54 × 10⁻⁷ M

J. Spiro-(5H-indeno[1,2-b]pyridine-5,3'-succinimide)

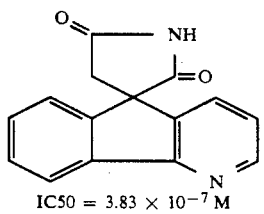

IC50 = 3.83 × 10⁻⁷ M

K. Spiro-(8H-indeno[2,1-b]thiophen-8,4'-imidazolidine)-2',5'-dione

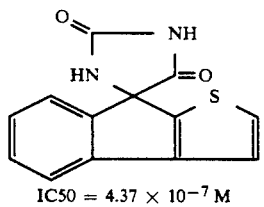

IC50 = 4.37 × 10⁻⁷ M

EXAMPLE XXVIII

Aldose reductase inhibitor potency may be evaluated in rat lens culture assays where 30 mM of glucose, galactose or xylose can be used in culture to induce a 'sugar' cataract. In addition to monitoring lens clarity, certain biochemical radiolabeled markers (e.g., choline —³H and ⁸⁶Rb) are employed to measure lens function. See Obazawa, Merola and Kinoshita, *Invest. Ophthalmol.*, 13 (1974) 204 and Jernigan, Kador and Kinoshita, *Exp. Eye Res.*, 32 (1981) 709.

In the present case, the 30 mM xylose cataract model was selected because 30 mM xylose is more effective in product 'sugar' cataracts than either 30 mM glucose or 30 mM galactose. The general procedure is as follows: a) Sprague-Dawley rats of 75-100 g body weight are sacrificed and the lenses removed immediately; b) the contralateral lens of the pair of lenses is employed as untreated control lens; c) the test lens is cultured in TC-199 culture media in the presence of 30 mM xylose, 30 mM xylose plus a selected concentration of test compound or a selected concentration of test compound; d) the contralateral control lens is treated identical to the test lens except no test compound or xylose is included; e) the matched lens pairs are cultured for 18 h in a $CO_2$ incubator; f) the lenses are compared morphologically and weighed. All lenses, control and test groups, are allowed to preincubate for 1 h in respective control media or drug control media prior to transfer to xylose media or xylose-drug media. In those cases where radiolabelled markers are to be measured, the lenses are treated as aforementioned except the radiolabelled marker(s) are added to the culture at four hours before harvesting. Radiolabelled markers include choline —³H ([methyl-¹⁴C]-choline chloride available from New England Nuclear), AIBA —¹⁴C (α-[1-¹⁴C]-$(CH_3)_2C(NH_2)COOH$ available from New England Nuclear) and ⁸⁶Rb. The effect of xylose on lens uptake of ⁸⁶Rb, lens uptake of amino acid (AIBA —¹⁴C) and lens uptake of choline —³H and the effectiveness of representative compounds of the present invention to preserve normal lens morphology is reported here.

The effect of 30 mM xylose and 30 mM xylose plus selected concentrations of test compound on radioactivity ratio is expressed as L/M % of control. L/M % of control is defined as the test lens radioactivity divided by culture media radioactivity as a percentage of the control contralateral lens radioactivity to media radioactivity ratio under identical test conditions but always without xylose or test compound in the control. The effect of 30 mM xylose in the culture media gives a reproducible deleterious effect on the lens as measured by the various L/M %. Furthermore, after incubation of the lens in 30 mM xylose in the TC-199 culture media, the lens gains 20% weight (mostly water weight increase based on dry lens weight measurements) and becomes opaque in the cortex of the lens. Each experiment requires 20-40 pairs of lenses to determine the potency of a selected aldose reductase inhibitor.

For comparison purposes, representative examples of the present invention will be profiled in the following table against examples from U.S. application Ser. Nos. 368,630 and 368,631.

REPRESENTATIVE COMPOUNDS EVALUATED

A. Spiro-(-2-fluoro-9H-fluoren-9,4'-imidazolidine)-2',5'-dione;

B. Spiro-(2,7-difluoro-9H-fluoren-9,4'-imidazolidine)-2',5'-dione;

C. Spiro-(2-fluoro-9H-fluoren-9,5'-thiazolidine)-2',4'-dione;

D. Spiro-(2,7-difluoro-9H-fluoren-9,5'-thiazolidine)-2',4'-dione.

| | Radiolabel Uptake-L/M% Table | | |
|---|---|---|---|
| Compound* | (1) L/M% | (2) L/M% | (3) L/M% |
| None | 47 | 33 | 45 |
| A | 73 | 50 | 55 |
| B | 105 | 87 | 82 |
| C | 77 | 58 | 70 |

| -continued | | | |
|---|---|---|---|
| Radiolabel Uptake-L/M% Table | | | |
| Compound* | (1) L/M% | (2) L/M% | (3) L/M% |
| D | 109 | 85 | 83 |

*Compound concentration $7.5 \times 10^{-7}$ M in culture media.

(1) L/M% = Lens uptake of choline $-^3$H after 18 h 30 mM xylose culture.

(2) L/M% = Lens uptake of AIBA $-^{14}$C (amino acid) after 18 h 30 mM xylose culture.

(3) L/M% = Lens uptake of $^{86}$Rb after 18 h 30 mM xylose culture.

In all cases Compounds A, B, C and D prevented lens opacification and lens wet weight increase at compound concentration of $7.5 \times 10^{-7}$M in the culture media.

Compound A and B according to U.S. application Ser. Nos. 368,360 and 368,631 are wholly effective in preventing cataract in galactosemic rats when administered per oral by gauge once a daily at 1.26 and 0.4 mg/kg respectively. In another efficacy study reported in the same applications, Compound A was found to prevent cataract and significantly preserve motor nerve conduction velocity in chronic streptozotocin-induced rats at 8 mg/kg per oral per day.

The following Examples XXIX–XXXVIII are presented to further illustrate methods for synthesizing certain preferred species of the present invention.

EXAMPLE XXIX

General Procedure for the Synthesis of 2,4,7-Trifluoro-5-Methylthiospiro[9H-Fluorene-9,4'-Imidazolidine]-2',5'-Dione

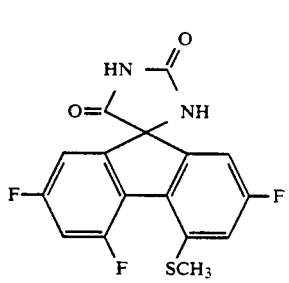

2,4,7-Trifluoro-5-nitrofluorene was oxidized to the fluorenone using sodium dichromate in acetic acid and then reduced to 5-amino-2,4,7-trifluorofluorenone using tin-(II)chloride in a mixture of ethanol and concentrated hydrochloric acid. The amine was converted to the 5-diazonium tetrafluoroborate salt by treatment with sodium nitrite in a mixture of tetrahydrofuran and aqueous fluoboric acid. The material was allowed to react with potassium ethyl xanthate in a hot mixture of water and toluene to provide ethyl 2,4,7-trifluoro-9-oxofluoren-5-yl xanthate which was then hydrolyzed using ethanolic sodium hydroxide and S-methylated with methyl iodide to give 2,4,7-tri-fluoro-5-methylthiofluorenone. Hydantoin formation was accomplished by heating an ethanol solution of the ketone, potassium cyanide, ammonium carbonate at 115° C. for 15 hours.

EXAMPLE XXX

General Procedure for the Synthesis of 2,4,7-Trifluoro-5-Methylspiro[9H-Fluorene-9,4'-Imidazolidine]-2',5'-Dione

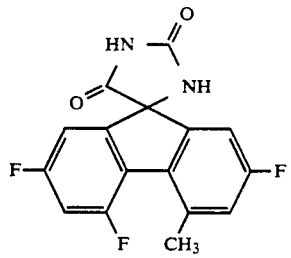

Treatment of 2,7-difluoro-4-methyl-9H-fluorenone in acetic acid with a mixture of nitric acid and sulfuric acid gave 2,7-difluoro-4-methyl-5-nitro-9H-fluorenone as the major product. 5-Amino-2,7-difluoro-4-methyl-9H-fluorenone was obtained by reduction using tin(II)chloride in a mixture of ethanol and aqueous hydrochloric acid. Thermal decomposition in hot xylene of the diazonium tetrafluoroborate, formed with sodium nitrite in aqueous fluoboric acid, provided 2,4,7-tri-fluoro-5-methyl-9H-fluorenone. Treatment of the ketone with potassium cyanide and ammonium carbonate in ethanol at 120° C. for 18 hours provided the title compound.

EXAMPLE XXXI

The Synthesis of 2,4,7-Trifluoro-5-Methoxyspiro(9H-Fluorene-9,4'-Imidazolidine)-2',5'-Dione

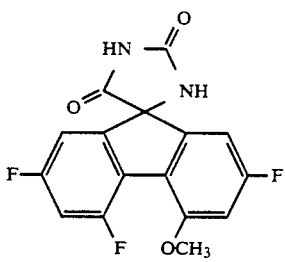

2,4,7-Trifluoro-5-methoxy-9H-fluorene

A solution of 5-amino-2,4,7-trifluoro-9H-fluorene (10.0 g, 0.042 mol) in 30 mL of tetrahydrofuran was added to 100 mL of 6M aqueous sulfuric acid. This solution was cooled to 0° C. and sodium nitrite (1.1 eq, 0.046 mol, 3.3 g), dissolved in small volume of water, was slowly added. After having stirred at 5° C. for 1 h, the mixture was added dropwise to 100 mL of 3M aqueous sulfuric acid at 100° C. The resulting mixture was heated at 100° C. for an additional 10 min, allowed to cool, and extracted with ethyl acetate. The ethyl acetate extracts were dried over MgSO$_4$ and concentrated to leave 10 g of a dark oil which was dissolved in a mixture of 15 mL tetrahydrofuran and 100 mL of 2M aqueous sodium hydroxide. The solution was heated to 40° C. and dimethyl sulfate (1 eq, 5.2 g, 4.1 mL) was added slowly. After the addition was complete, the solution was heated to 50° C. and another 0.5 eq of dimethyl sulfate was added. After 1 h at 50° C., the solution was cooled to room temperature and extracted with 50 mL of ethyl acetate. The ethyl acetate extract was washed with water and brine, dried over MgSO$_4$, and concentrated to leave 9.0 g of a dark solid which was chromatographed on silica gel using 20% ethyl acetate in hexane to provide 4.8 g (45%) of the fluorene.

2,4,7-Trifluoro-5-methoxy-9H-fluoren-9-one

Sodium dichromate dihydrate (2 eq, 0.26 mol, 7.9 g) was added to a solution 2,4,7-trifluoro-5-methoxy-9H-fluorene (3.3 g, 0.013 mol) in 100 mL of acetic acid and the mixture was refluxed for 5 h. The cooled reaction mixture was poured into water and extracted with ethyl acetate. The ethyl acetate extract was washed with saturated aqueous sodium bicarbonate and water, dried over MgSO$_4$, and concentrated to leave 3 g of a yellow solid which was chromatographed on silica gel using 15% ethyl acetate in hexane to provide 2.0 g (57%) of the fluorenone: mp 164°–166° C.

2,4,7-Trifluoro-5-methoxyspiro(9H-fluorene-9,4'-imidazolidine)2',5'dione

A mixture of 2,4,7-trifluoro-5-methoxy-9H-fluoren-9-one (2.0 g, 7.6 mmol), potassium cyanide (3 eq, 23 mmol, 1.5 g), and ammonium carbonate (4 eq, 30 mmol, 2.9 g) in 50 mL of ethanol was heated in a sealed bomb at 115° C. for 24 h. After the bomb was cooled and opened, the solvent was evaporated and the residue dissolved in 1M aqueous sodium hydroxide. The basic solution was extracted with ethyl acetate to remove base insoluble impurities and then acidified using concentrated hydrochloric acid. The acidic solution was extracted with ethyl acetate and the extracts were dried over MgSO$_4$ and concentrated to leave 1.2 g of a brown solid. Chromatography on silica gel using 45% ethyl acetate in hexane provided 500 mg (20%) of the spirohydantoin: mp 227°–229° C.

Analysis calculated for C$_{16}$H$_9$F$_3$N$_2$O$_3$: C,57.49; H, 2.71; N, 8.38. Found: C,57.68; H, 2.81; N, 8.34.

EXAMPLE XXXII

Synthesis of 2,4,5,7-Tetrafluorospiro (9H-fluorene-9,4'-imidazolidine-2',5'-dione Experimental details for the four-step synthesis of 2,4,5,7-tetrafluorospiro (9H-fluorene-9,4'-imidazolidine-2',5'-dione from 3,5-difluorobromobenzene are provided. Also included is a procedure for the preparation of palladium acetate from the palladium metal which is recovered from the last step and recycled.

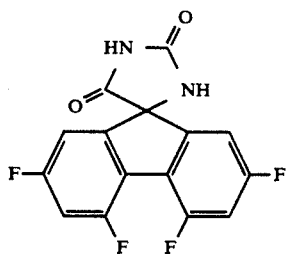

3,3',5,5'-Tetrafluorodiphenylcarbinol

A 22-L flask equipped with a mechanical stirrer, a 2-L addition funnel, an efficient condenser, and a bottom drain was dried under a stream of dry nitrogen overnight and then charged with magnesium turnings (90.1 g, 3.70 mol) and anhydrous ether (2 L). A portion (200 mL) of a solution of 3,5-difluorbromobenzene (650.0 g, 3.37 mol) (Note 1) in 1500 mL of ether was added and the mixture was heated to reflux. A small amount (~3 g) of difluorophenylmagnesium bromide (prepared in a test tube) was added to initiate the reaction. When the reaction mixture turned gray and cloudy, the heating mantle was turned off as the exothermic reaction maintained reflux temperature. Shortly afterwards the mixture turned brown and a vigorous reaction set in. After this subsided, the remaining difluorobromobenzene solution was added at a rate which maintained a steady reflux (required 2 hrs) (Note 2). After the addition was complete, the mixture was refluxed for 30 min before the heat was turned off and a solution of ethylformate (125.0 g, 1.69 mol) in ether (1.5 L) was added at a rate that maintained a gentle reflux. The mixture was then refluxed for another hour before it was quenched by the addition of 6 L of 20% aqueous hydrochloric acid. The aqueous layer was removed and the organic layer was washed twice with water, dried over MgSO$_4$, filtered, and concentrated to leave 427 g of a dark brown, viscous oil. The oil was distilled using a short path, large bore distillation apparatus to provide 217 g (50%) of a pale yellow solid (Notes 3 and 4): bp 108°–115° C./0.06 mmHg; mp 61°–64° C.; MS m/z 256 (M+), 141 (base peak); $^1$H NMR (CDCl$_3$) δ6.82–6.42 (m, 6); 5.62 (d, 1); 2.18 (d, 1); IR (KBr) 3300 (broad), 1615, 1592, 1115 cm$^{-1}$.

Notes

1. The 3,5-difluorobromobenzene was purchased from Yarsley Chemical Company.
2. In order to avoid an uncontrollable reaction, it is essential that the grignard reaction be well established (as evidenced by the formation of the brown color) before a large volume of aryl bromide is added.
3. At the expense of yield, colorless material can be obtained by a more careful distillation.
4. Subsequent oxidation attempts using the crude alcohol resulted in a product which was very difficult to isolate and purify.

3,3',5,5'-Tetrafluorobenzophenone

In a 22-L flask equipped with a mechanical stirrer and thermometer, 3,3',5,5'-Tetrafluorodiphenylcarbinol (404 g, 1.58 mol) was dissolved in 3 L of glacial acetic acid. Sodium dichromate dihydrate (471 g, 1.58 mol) was added in one portion, forming a dark brown solution and an exothermic reaction which caused the temperature to rise to 60° C. within 30 min and maintained that temperature for 15 min. When the temperature began to fall, TLC analysis indicated that the reaction was complete (Note 1). Water (~10 L) was added to the reaction and the precipitate was collected by filtration, washed with water until the washings were colorless, and dried in the funnel. The white solid was then dissolved in ethyl acetate (~4 L), washed with water (2×2.5 L), dried over MgSO$_4$, filtered, and evaporated to dryness to provide 358 g (89%) of the ketone which was used in the next step without further purification: mp 84°–87° C.; MS m/z 254 (M+); $^1$H NMR (CDCl$_3$) δ7.28–6.80 (m, 6); IR (KBr) 3080, 1670, 1582, 1115, 975, 745 cm$^{-1}$.

Note

1. A sample was added to water and extracted with ethyl acetate. The ethyl acetate solution was spotted on a silica gel plate and developed using 20% ethyl acetate/hexane. The $R_f$ of the starting material is 0.6 while that of the product is 0.8.

5,5-Di(3,5-difluorophenyl)-2,4-imidazolidinedione

A mixture of 3,3',5,5'-tetrafluorobezophenone (358 g, 1.41 mol), potassium cyanide (137.5 g, 2.11 mol), ammonium carbonate (406 g, 4.22 mol) and ethanol (3.5 L) was heated at 115° C. for 16 h in a stirred 2 gal pressure reactor. After chilling to relieve the pressure, the reactor was opened and the mixture was poured into 8 L of water in a 22-L flask equipped with a mechanical stirrer. The mixture was acidified (pH 2.0) using concentrated hydrochloric acid (~1 L) (Note 1) and the resulting precipitate was collected by filtration, washed with water, and pressed dry. The crude material was recrystallized from ethanol (~6 L) to provide 399.5 g (87%) of 5,5-di(3,5-difluorophenyl)-2,4-imidazolidinedione (Note 2): mp 271°–274° C.; MS m/z 324 (M+); $^1$H NMR (DMSO-d$_6$) δ9.50 (s, 2); 7.42–6.90 (m, 6); IR (KBr) 3265, 3160, 3060, 1762, 1710 cm$^{-1}$.

Analysis calcd. for $C_{15}H_8F_4N_2O_2$: C, 55.57; H, 2.49; N, 8.64. Found: C, 55.55; H, 2.38; N, 8.62.

1. This step should be carried out cautiously in an efficient hood since hydrogen cyanide is formed. The acidification is done slowly to control the vigorous foaming.
2. Recrystallization of the product simplifies the work-up procedure of the following reaction.

2,4,5,7-Tetrafluorospiro(9H-fluorene-9,4'-imidazolidine)-2',5'-dione

A solution of 5,5-di(3,5-difluorophenyl)-2,4-imidazolidinedione (240 g, 0.74 mol) and palladium(II) acetate (167.8 g, 0.748 mol) in 2.4 L of a 50% mixture (v/v) of glacial acetic acid and 69%–72% perchloric acid in a 5-L flask equipped with a mechanical stirrer and a thermometer was heated at 120° to 135° C. for 1.5 h. The reaction mixture was filtered hot through a fritted glass funnel and the black palladium metal was washed well with hot acetic acid. the combined filtrate and washings were poured into 10 L of water and the precipitate was collected by filtration, washed with water, and dried in the funnel. The crude solid was then dissolved in boiling acetonitrile, treated with decolorizing carbon, filtered through celite, and concentrated to 3 L. The solution was slowly cooled to room temperature and then in the refrigerator as the product crystallized. The white crystals were collected by filtration, washed with acetonitrile, and dried to provide 167 g (70%) of 2,4,5,7-tetraflourospiro (9H-fluorene-9,4'-imidazolidine-2',5'-dione. A second recrystallization gave 150 g of pure compound: mp 287°–290° C.; MS m/z 322 (M+), 251 (base peak); $^1$H NMR (DMSO-d$_6$)δ8.73 (s, 2), 7.52–7.49 (m, 4); IR (KBr) 3340–3160 (broad), 1772, 1722, 1122 cm$^{-1}$.

Anal. calcd. for $C_{15}H_6F_4N_2O_2$: C, 55.91; H, 1.88; N, 8.69; Found: C, 55.65; H, 1.96; N, 8.70.

EXAMPLE XXXIII

The Synthesis of 2,4,5,7-Tetrafluorospiro(9H-fluorene-9,5'-thiazolidine)-2',4'-dione Experimental details for the four step synthesis of 2,4,5,7-Tetrafluorospiro(9H-fluorene-9,5'-thiazolidine)-2',4'-dione from 2,4,5,7-tetrafluorofluorene are provided.

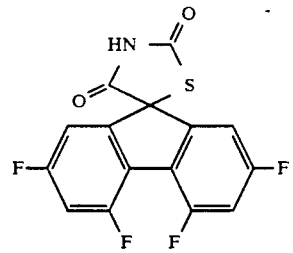

Methyl 2,4,5,7-Tetrafluorofluorene-9-carboxylate

Under nitrogen, n-butyllithium (5.6 mL of a 2.5M hexane solution) was added dropwise, to a −78° C. solution of the 2,4,5,7-tetrafluorofluorene in gold label THF (80 mL) over 2 min. After 20 min, the mixture was poured onto a slurry of dry-ice (10 g) in anhydrous ether. The solvents were evaporated and the residue was dissolved in methanol (200 mL) and acidified with acetyl chloride (5 mL). After stirring for 18 h, the reaction was concentrated and the residue was diluted with saturated aqueous sodium bicarbonate (200 mL) and extracted with ethyl acetate (3×100 mL). The combined organics were washed with brine (3×100 mL), dried (MgSO$_4$), and evaporated. The residue was chromatographed on silica gel using petroleum ether to provide 2.1 g (57%) of product: $^1$H NMR (DMSO-d$_6$, 200 MHz) δ7.44 (dd, 2H, J=2.2 and 8.3 Hz), 7.40–7.25 (m, 2H), 5.37 (s, 1H), 3.76 (s, 3H).

Methyl 9-Chloro-2,4,5,7-tetrafluorofluorene-9-carboxylate

A solution of methyl 2,4,5,7-tetrafluorofluorene-9-carboxylate (1.49 g, 5.03 mmol) in dry THF (15 mL) was added over 14 min to a stirred, room temperature suspension of unwashed sodium hydride (1.25 eq, 6.29 mmol, 250 mg of a 60% oil dispersion) in THF (15 mL). The mixture was then cooled in an ice water bath and after 9 min a solution of N-chlorosuccinimide (1.2 eq, 6.04 mmol, 810 mg) was added over 14 min. After slowly warming to room temperature, the mixture was stirred for 21 h before it was poured into 100 mL of water and extracted with ethyl acetate. The extracts were washed with aqueous sodium carbonate, aqueous sodium bisulfate, and brine, dried (MgSO$_4$), and concentrated to leave 1.4 g of crude material. Chromatography on silica gel using 20% ethyl acetate in hexane provided 970 mg (58%) of nearly pure material: $^1$H NMR (CDCl$_3$) δ7.20 (dd, 2H), 7.0–6.6 (m, 2H), 3.75 (s, 3H); IR (KBr) 1730, 1600, 1580, 1410, 1105 cm$^{-1}$; MS m/z 330 (M+), 271 (base peak).

2,4,5,7-Tetrafluorospiro(9H-fluorene-9,5'-thiazolidine)-2'-imino-4'-one

A mixture of methyl 9-chloro-2,4,5,7-tetrafluorofluorene-9-carboxylate (970 mg, 2.94 mmol), thiourea (1.1 eq, 3.23 mmol, 250 mg), and sodium acetate (0.75 eq, 2.20 mmol, 180 mg) in acetic acid (8 mL) was refluxed for 8 h. The mixture was cooled to room temperature and the precipitate was collected by filtration, washed with acetic acid and ether, and air dried to provide 440 mg of crude material: MS m/e 338 (M+), 268 (base peak).

2,4,5,7-Tetrafluorospiro(9H-fluorene-9,5'-thiazolidine)-2',4'-dione

Crude 2,4,5,7-tetrafluorospiro(9H-fluorene-9,5'-thiazolidine)-2'-imino-4'-one (440 mg) was refluxed in a mixture of 8 mL each of methanol and concentrated hydrochloric acid for 4 h. After the mixture cooled to room temperature, 8 mL of water was added and the white solid was collected, washed with cold water, and dried to provide 180 mg of crude product. Chromatography on silica gel using a gradient of 1% to 10% methanol in chloroform provided 90 mg of the thiazolildine dione: $^1$H NMR (DMSO-$d_6$, 200 MHz) $\delta$ 7.78 (dd, 2H, J=2.2 and 8.0 Hz), 7.52–7.41 (m, 2H); IR (KBr) 1750, 1700 cm$^{-1}$; MS m/z 339 (M+), 268 (base peak).

Anal. calcd for $C_{15}H_5F_4NO_2S$: C, 53.10; H, 1.49; N, 4.13. Found: C, 52.88; H, 1.58; N, 4.00.

EXAMPLE XXXIV

The Preparation of 2,7-Difluoro-3-Methylspiro(9H-Fluorene-9,4'-Imidazolidine)-2',5'-Dione

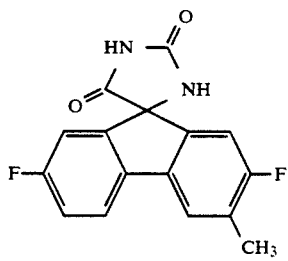

Methyl 2-(3-methyl-4-fluorophenyl)-5-fluorobenzoate

A mixture of 4-fluoro-3-methylphenylboronic acid (6.5 g, 42.5 mmol), methyl 2-bromo-5-fluorobenzoate (10.0 g, 42.9 mmol), tetrakis (triphenylphosphine) palladium(O) (1.0 g, 0.87 mmol, 0.2 eq), toluene (100 mL), 2M aqueous sodium carbonate (50 mL) and ethanol (25 mL) was refluxed for 9 h. The reaction mixture was then poured into 50 mL each of concentrated ammonium hydroxide, 2M aqueous sodium carbonate, and water, the organic phase was separated, and the aqueous was extracted with ethyl acetate. The combined organics were washed with brine, dried over MgSO$_4$, and concentrated to leave an oil which was chromatographed on silica gel using hexane to provide 11 g (98%) of the ester.

Methyl 2-(3-methyl-4-fluorophenyl)-5-fluorobenzoic acid

Potassium hydroxide (6 g) and water (50 mL) were added to a solution of methyl 2-(3-methyl-4-fluorophenyl)-5-fluorobenzoate (10.2 g, 40.0 mmol) in methanol (150 mL) and the mixture was stirred at room temperature for 18 h. The reaction mixture was then evaporated to near dryness, acidified with 1N aqueous hydrochloric acid, and extracted with ethyl acetate. The combined extracts were washed with brine, dried over MgSO$_4$, and concentrated to leave a residue which was chromatographed on silica gel using 30% ethyl acetate in hexane to provide 9.7 g of the acid.

2,7-Difluoro-3-methyl-9H-fluorenone

A stirred mixture of methyl 2-(3-methyl-4-fluorophenyl)-5-fluorobenzoic acid (6.5 g, 26.2 mmol) and polyphosphoric acid (30 g) was heated at 180° C. for 2 h. After the mixture had cooled to 80° C., it was poured into water (200 mL), and extracted with ethyl acetate. The combined extracts were washed with brine, dried over MgSO$_4$, treated with charcoal, and concentrated. Chromatography on silica gel using 20% toluene in hexane provided 2 g (33%) of the desired ketone.

2,7-Difluoro-3-methylspiro(9H-fluorene-9,4'-imidazolidine)-2',5'-dione

A mixture of 2,7-difluoro-3-methyl-9H-fluorenone (1.8 g, 7.8 mmol), potassium cyanide (2.0 g, 31.2 g, 4 eq), and ammonium carbonate (2.2 g, 23.4 mmol, 3 eq) in 60 mL of ethanol was heated in a sealed bomb at 115° C. for 24 h. The cooled bomb was opened, and the excess potassium cyanide was destroyed with 1M aqueous hydrochloric acid. The mixture was then partitioned between 1M aqueous sodium hydroxide (150 mL) and ethyl acetate (200 mL) and the basic aqueous phase was removed. The organic phase was extracted with 1M sodium hydroxide and the combined basic phases were acidified and extracted with ethyl acetate. The combined extracts were washed with brine, dried over MgSO$_4$, and concentrated. The residue was recrystallized from ethanol/water to provide 290 mg of pure hydantoin: mp>315° C.

Analysis calculated for $C_{16}H_{10}F_2N_2O_2$: C, 64.00; H, 3.36; N, 9.33. Found: C, 64.05; H, 3.35; N, 9.35.

EXAMPLE XXXV

Synthesis of 2,7-Difluoro-4-methylspiro(9H-fluorene-9,4'-imidazolidine)-2',5'-dione The preparation of 2,7-difluoro-4-methylspiro(9H-fluorene-9,4'-imidazolidine)-2',5'-dione from ethyl 2-(2-methyl-4-fluorophenyl)-5-fluorobenzoate is described.

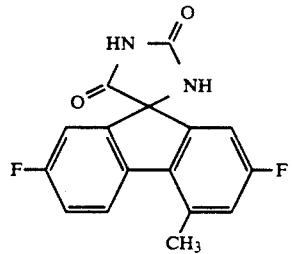

Ethyl 2-(2-Methyl-4-fluorophenyl)-5-fluorobenzoate

Tetrakis(triphenylphosphine)palladium(O) (0.02 eq, 0.31 g) was added to a vigorously stirred solution of ethyl 2-bromo-5-fluorobenzoate (1.0 eq, 3.3 g, 0.013 mol) and 2-methyl-4-fluorophenylboronic acid (1.2 eq, 0.016 mol, 2.4 g) in 45 mL of toluene, 22 mL of 2M aqueous sodium carbonate, and 11 mL of ethanol and the mixture was refluxed for 9 h. The cooled reaction mixture was poured into 50 mL each of water, ammonium hydroxide, and 2M aqueous sodium bicarbonate and then filtered through Celite. The filtrate was extracted with ethyl acetate and the organics were dried (MgSO$_4$) and concentrated to yield 3.9 g of a yellow oil. Chromatography (silica gel, 20% ethyl acetate/hexane) gave 3.4 g (92%) of product as a light colored oil. $^1$H NMR (CDCl$_3$, 60 mHz) $\delta$ 7.7 (dd, 1H), 7.5 (m, 1H), 7.25–6.75 (m, 4H), 4.0 (q, 2H), 2.0 (s, 3H), 1.0 (t, 3H); IR (CDCl₃ solution) 3130, 2220, 1700, 1450, 1080 cm⁻¹; MS m/z 276 (M+), 201 (base peak).

2-(2-Methyl-4-fluorophenyl)-5-fluorobenzoic acid

A solution of methanol (25 mL), water (10 mL), potassium hydroxide (2 eq, 1.2 g), and ethyl 2-(2-methyl-4-fluorophenyl)-5-fluorobenzoate (1.0 eq, 3.4 g) was allowed to stir at room temperature for 16 h. The reaction was then concentrated in vacuo and the residue dissolved in 20 mL of water. Acidification with concentrated hydrochloric acid resulted in the precipitation of the product as a white solid. The solid was collected by filtration, dissolved up in ethyl acetate, washed with water, and then dried over magnesium sulfate. Concentration of the ethyl acetate solution left 3.2 g of product as a white solid. MS m/z 248 (M+), 201 (base peak).

2,7-Difluoro-4-methyl-9-fluorenone 2-(2-Methyl-4-fluorophenyl)-5-fluorobenzoic acid (3.2 g, 0.013 mol) was placed in 40 g of polyphosphoric acid and heated at 210° C. for 1.5 h. The reaction was allowed to cool and was then poured into 200 mL of ice water. Ethyl acetate and 1N aqueous sodium hydroxide (100 mL each) were added and the solution was filtered through celite. The organic layer was separated and the aqueous layer was extracted once again with 75 mL of ethyl acetate. The combined organics were washed with saturated aqueous sodium bicarbonate and water, dried (MgSO₄), and concentrated in vacuo leaving 1.9 g of product as a yellow solid. Recrystallization from ethanol gave 1.5 g (52%) of pure product: mp 172°-175° C.; ¹H NMR (CDCl₃, 60 mHz) δ7.6-6.7 (m, 5H), 2.5 (s, 3H); IR (KBr) 1700, 1460, 1280, 775 cm⁻¹; MS m/z 230 (M+). Analysis Calculated for C₁₄H₈OF₂: C, 73.04; H, 3.50. Found: C, 72.93; H, 3.67.

2,7-Difluoro-4-methylspiro(9H-fluorene-9,4'-imidazolidine)-2',5'-dione 2,7-Difluoro-4-methyl-9-fluorenone (1.3 g, 0.0056 mol), potassium cyanide (3 eq, 0.017 mol, 1.1 g), ammonium bicarbonate (3 eq, 0.017 mol, 1.3 g), and 50 mL of ethanol were placed in a sealed bomb and heated at 125° C. for 20 h. The bomb was cooled to room temperature and the contents were filtered through Celite washing with water and ethyl acetate. The filtrate was concentrated in vacuo and the residue was dissolved in 40 mL of 1N aqueous sodium hydroxide and washed with ethyl acetate (2×30 mL). The aqueous solution was acidified with concentrated hydrochloric acid and the product extracted into ethyl acetate. The organic solution was then dried and concentrated providing 1.1 g of a crude white solid which was recrystallized from ethanol to give 340 mg of 2,7-difluoro-4-methylspiro(9H-fluorene-9,4'-imidazolidine)-2',5'-dione: mp>320° C.; ¹H NMR (DMSO-d₆, 60 mHz) δ8.5 (s, 1H), 7.8 (m, 1H), 7.2 (m, 4H), 2.7 (s, 3H); IR (KBr) 3300, 1710, 1380, 770 cm⁻¹; MS m/z 300 (M+), 229 (base peak). Analysis Calculated for C₁₆H₁₀F₂N₂O₂·½H₂O: C, 62.14; H, 3.58; N, 9.06. Found: C, 62.21; H, 3.58; N, 8.81.

EXAMPLE XXXVI

Synthesis of 2,7-Difluoro-4-methoxyspiro(9H-fluorene-9,4'-imidazolidine)-2',5'-dione The preparation of 2,7-Difluoro-4-methoxyspiro(9H-fluorene-9,4'-imidazolidine)-2',5'-dione from 2,7-difluoro-4-aminofluorene is described.

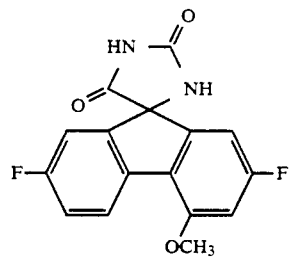

2,7-Difluoro-4-methoxy-9H-fluorene

A solution of 2,7-difluoro-4-amino-9H-fluorene, (10 g, 0.046 mol) in 20 mL of tetrahydrofuran was added to 100 mL of 6M aqueous sulfuric acid. This yellow solution was cooled to 0° C. and sodium nitrite (1.0 eq, 3.6 g), dissolved in a small volume of water, was slowly added. The temperature was kept below 5° C. throughout the addition and was kept at 0° C. for 1 h afterward. The reaction was then added to a 100° C. 3M aqueous sulfuric acid solution. The temperature of the hot acid solution was controlled by the rate of addition and was not allowed to go below 85° C. After complete addition, the reaction was stirred for 2 minutes at 100° C. and then allowed to cool to room temperature. The aqueous solution was extracted with ethyl acetate (2×20 mL) and the combined extracts were dried (MgSO₄), filtered through a small pad of silica gel, and concentrated in vacuo. The residue was dissolved in 100 mL of 2N aqueous sodium hydroxide and heated to 45° C. Dimethyl sulphate (1.0 eq, 4.5 mL) was then added dropwise. The solution was kept basic and at 45° C. throughout the addition. Another portion of dimethyl sulphate (0.5 eq., 2.3 mL) was added and the solution was heated to 50° C. for 30 minutes. The cooled solution was extracted with ethyl acetate (2×50 mL) and the extracts were dried (MgSO₄), treated with carbon, filtered, and concentrated to give a crude black solid. The solid was stirred in 500 mL of hexane and the insoluble material filtered off. Concentration of the hexane solution gave 6.8 g of a crude yellow solid. Chromatography (silica gel, 10% ethyl acetate in hexane) gave 6.3 g (58%) of product as a yellow crystalline solid: ¹H NMR (CDCl₃, 60 MHz) δ7.9 (dd, 1H), 7.2-6.3 (m, 4H), 3.9 (s, 3H), 3.7 (s, 2H); IR (KBr) 1590, 1450, 1120, 830 cm⁻¹; MS m/z 232 (M+).

2,7-Difluoro-4-methoxy-9H-fluorenone 2,7-Difluoro-4-methoxy-9H-fluorene (4 g, 0.017 mol), sodium dichromate dihydrate (1.1 eq, 5.7 g) and 50 mL of acetic acid were heated to 50° C. for 1 h. No change was observed on TLC (30% ethyl acetate/hexane) so the temperature was raised to 75° C. and held there for 3 h. The reaction was then poured into water and extracted with ethyl acetate. The organic solution was washed with aqueous sodium bicarbonate, dried (MgSO₄), and concentrated in vacuo to give 3.8 g of a yellow solid. Recrystallization of the solid from ethanol gave 1.1 g of pure product. (The rest of the material was identified as starting material): ¹H NMR (CDCl₃, 60 MHz) δ7.5 (dd, 1H), 7.2-6.6 (m, 4H), 3.9 (s, 3H); IR (KBr) 1700, 1450, 1300, 780 cm⁻¹; MS m/z 246 (M+).

2,7-Difluoro-4-methoxyspiro(9H-fluorene-9,4'-imidazolidine)-2',5'-dione 2,7-Difluoro-4-methoxy-9H-fluorenone (1.1 g, 0.004 mol), potassium cyanide (1.5 eq, 0.007 mL, 0.44 g), ammonium carbonate (3.0 eq, 0.014 mol, 1.3 g) and 25 mL of ethanol were placed in a sealed bomb and heated at 115° C. for 24 h. The cooled reaction mixture was poured into a boiling flask and concentrated in vacuo. The residue was dissolved in ethyl acetate and the solution was washed with 1N aqueous hydrochloric acid, treated with carbon, dried (MgSO$_4$), filtered, and concentrated to give 1.5 g of an off-white solid. The solid was dissolved in 1N aqueous sodium hydroxide, filtered through Celite, and acidified with concentrated hydrochloric acid. The white precipitate was collected and recrystallized from ethanol. The still impure product was chromatographed (silica gel, 10% acetone/hexane) to give 300 mg of pure 2,7-difluoro-4-methoxyspiro(9H-fluorene-9,4'-imidazolidine)-2',5'-dione: 1H NMR (CDCl$_3$, 200 MHz) δ11.3 (s, 1H, exchangeable), 8.66 (s, 1H, exchangeable), 7.88 (dd, 1H, J=5.2 and 8.5 Hz), 7.44 (dd, 1H, J=2.3 and 8.5 Hz), 7.29 (ddd, 1H, J=2.5, 8.5, and 9.5 Hz), 7.08 (dd, 1H, J=2.1 and 11.6 Hz), 7.03 (dd, 1H, J=2.1 and 8.0 Hz), 3.98 (s, 3H); IR (KBr) 1700, 1450, 1190, 830 cm$^{-1}$; MS m/z 316 (M+), 71 (base peak). Analysis calculated for C$_{16}$H$_{10}$F$_2$N$_2$O$_3$: C, 60.76; H, 3.19; N, 8.86. Found: C, 60.65; H, 3.19; N, 8.86.

EXAMPLE XXXVII

Synthesis of 3,7-Difluoro-9-methylspiro[5H-indeno[1,2-b]pyridine-5,4'-imidazolidine]-2',5'-dione The four-step synthesis of 3,7-Difluoro-9-methylspiro[5H-indeno[1,2-b]pyridine-5,4'-imidazolidine]-2',5'-dione from ethyl 2-(2-methyl-4-fluorophenyl)-5-fluoro-3-pyridinecarboxylate is described.

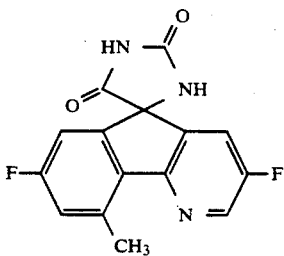

Ethyl 2-(2-methyl-4-fluorophenyl)-5-fluoro-3-pyridinecarboxylate

Tetrakis(triphenylphosphine)palladium(O) (0.02 eq, 0.89 g) was added to a vigorously stirred solution of ethyl 2-chloro-5-fluoro-3-pyridinecarboxylate (0.038 mol, 7.8 g) and 2-methyl-4-fluorophenylboronic acid (1.5 eq, 0.057 mol, 8.9 g) in 100 mL of toluene, 50 mL of 2M aqueous sodium carbonate, and 25 mL of ethanol and the mixture was refluxed for 9 h. The cooled reaction mixture was poured into 100 mL each of water, ammonium hydroxide, and 2M aqueous sodium carbonate and then filtered through Celite. The filtrate was extracted with ethyl acetate and the organics were dried (MgSO$_4$) and concentrated to yield 12 g of a red oil. Chromatography (silica gel, 20% ethyl acetate/hexane) gave 9.7 g (92%) of product as a light colored oil: 1H NMR (CDCl$_3$, 60 MHz) δ8.7 (d, 1H), 8.0 (dd, 1H), 7.1-6.8 (m, 3H), 4.1 (q, 2H), 2.0 (s, 3H); MS m/z 277 (M+).

2-(2-Methyl-4-fluorophenyl)-5-fluoro-3-pyridinecarboxylic Acid

A solution of methanol (100 mL), water (10 mL), potassium hydroxide (2 eq, 4.0 g), and ethyl 2-(2-methyl-4-fluorophenyl)-5-fluoro-3-pyridinecarboxylate (1.0 eq, 9.6 g) was allowed to stir at room temperature for 16 h. The reaction was then concentrated in vacuo and the residue dissolved in 80 mL of water. Acidification with concentrated hydrochloric acid did not result in precipitation of product so the product was extracted out with ethyl acetate. Drying (MgSO$_4$) and concentration of the organics left 8.5 g (99%) of product as an off-white solid: 1H NMR (CDCl$_3$, 60 MHz) δ9.7 (s, 1H), 8.7 (d, 1H), 8.0 (dd, 1H), 7.1-6.8 (m, 3H), 2.0 (s, 3H); MS m/z 249 (M+), 204 (base peak).

3,7-Difluoro-9-methyl-5H-indeno[1,2-b]pyridin-5-one 2-(2-methyl-4-fluorophenyl)-5-fluoro-3-pyridinecarboxylic acid (8.5 g, 0.034 mol) was placed in 102 g of polyphosphoric acid and heated at 210° C. for 3 h. The reaction was allowed to cool and was then poured into 500 mL of ice water. Ethyl acetate and 1N aqueous sodium hydroxide (200 mL each) were added and the solution was filtered through Celite. The organic layer was separated and the aqueous layer was extracted with ethyl acetate (2×75 mL). The combined organics were washed with saturated aqueous sodium bicarbonate and water, dried (MgSO$_4$), and concentrated in vacuo leaving 4.0 g of a greenish solid. Recrystallization from ethanol/ethyl acetate with carbon treatment gave 2.1 g of clean product: mp 155°–157° C.; 1H NMR (CDCl$_3$, 60 MHz) δ8.3 (dd, 1H), 7.4 (dd, 1H), 7.2–6.8 (m, 2H), 2.7 (s, 3H); IR (KBr) 1730, 1470, 1280, 785 cm$^{-1}$; MS m/z 231 (M+), 203 (base peak); Analysis calculated for C$_{13}$H$_7$NOF$_2$: C, 67.54; H, 3.05; N, 6.06. Found: C, 67.20; H, 3.20; N, 5.76.

3,7-Difluoro-9-methylspiro[5H-indeno[1,2-b]pyridin-5,4'-imidazolidine]-2',5'-dione 3,7-difluoro-9-methyl-5H-indeno[1,2-b]pyridin-5-one (2.0 g, 0.0087 mol), potassium cyanide (2.5 eq, 0.022 mol, 1.4 g), ammonium carbonate (4 eq, 3.3 g), and 50 mL of ethanol were placed in a sealed bomb and heated to 115° C. for 24 h. The bomb was cooled to room temperature and the contents were filtered through Celite washing with water and ethyl acetate. The filtrate was concentrated in vacuo and the residue was dissolved in 50 mL of 1N aqueous sodium hydroxide and washed with ethyl acetate (2×30 mL). The aqueous solution was acidified with concentrated hydrochloric acid and extracted with ethyl acetate (2×50 mL). The organics were dried (MgSO$_4$) and concentrated in vacuo to give 600 mg of a crude tan solid. Recrystallization from ethanol gave 250 mg of pure product: mp<320° C.; 1H NMR (DMSO-d$_6$, 200 MHz) δ11.42 (s, 1H, exchangeable), 8.66 (s, 1H, exchangeable), 8.60 (m, 1H), 8.17 (dd, 1H, J=2.7 and 8.2 Hz), 7.37 (dd, 1H, J=2.3 and 8.2 Hz), 7.24 (dd, 1H, J=1.7 and 10.3 Hz), 2.79 (s, 3H); IR (KBr) 3200, 1710, 1390, 1130 cm$^{-1}$; MS m/z 301 (M+); Analysis calculated for C$_{15}$H$_9$F$_2$N$_3$O$_2$: C, 59.81; H, 3.01; N, 13.95. Found: C, 59.86; H, 3.17; N, 13.67.

EXAMPLE XXXVIII

General Procedure for the Synthesis of 3,7-Difluoro-9-Methylspiro[5H-Indeno[1,2-b]Pyridin-5,3'-Pyrrolidine]-2',5'-Dione

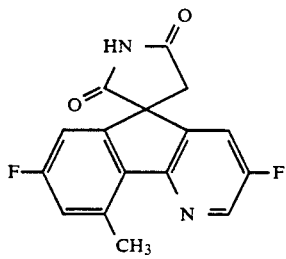

Treatment of 3,7-difluoro-9-methyl-5H-indeno[1,2-b]pyridin-5-one with hydrazine in hot diethylene glycol provided 3,7-difluoro-9-methyl-5H-indeno[1,2-b]pyridine. Deprotonation using n-butyllithium in tetrahydrofuran followed by reaction with carbon dioxide and methanolic hydrogen chloride provided 3,7-difluoro-9-methyl-5H-indeno[1,2-b]pyridine-5-carboxylic acid methyl ester. The ester was then deprotonated using a slight excess of sodium hydride in tetrahydrofuran and treated with iodoacetamide to provide, after 18 hours at room temperature and 6 hours at reflux, the title compound.

Of special interest according to the present invention are tetrasubstituted compounds of the formula:

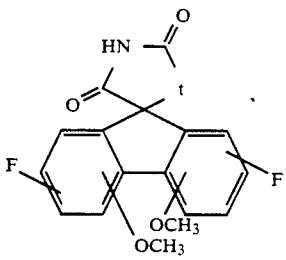

wherein t is selected from the group consisting of NH, O, S and CHR wherein R' is hydrogen or lower alkyl of 1 to 5 carbon atoms. Especially preferred compounds are those where the fluoro and methoxy substituents are located in the ring in meta position to each other.

An especially preferred compound is 2,7-difluoro-4,5-dimethoxyspiro (9H-fluorene-9,4'-imidazolidine)-2',5'-dione of the formula:

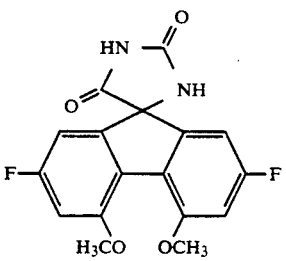

This compound is a very potent aldose reductase inhibitor with an IC$_{50}$ value of $0.78 \times 10^{-8}$ Mol/L. The IC$_{50}$ value is based on the inhibition of rat lens aldose reductase.

The above compounds are prepared from trifluoro-5-hydroxyfluorenone by reaction with alkali metal alkoxide in a solvent such as dimethyl formamide followed by alkyl iodide to provide the difluoro-dialkoxyfluorenone in good yield. Subsequent conversion to the hydantoin can be carried out using standard Bucherer-Bergs conditions as described herein to produce the desired product in good yield.

EXAMPLE XXXIX 2,7-Difluoro-4,5-Dimethoxyfluorenone

A mixture 2,4,7-trifluoro-5-hydroxyfluorenone (2.5 g, 10 mmol) and sodium methoxide (6 mL of a 25% solution in methanol, 3 eq) in dry dimethylformamide (80 mL, over sieves) was stirred under nitrogen at room temperature. After 2 h, additional sodium methoxide (6 mL of a 25% solution in methanol, 3 eq) was added. Stirring was continued for 2 h at which time the mixture was treated with iodomethane (15 mL, 46 mmol 4.6 eq) over 20 min. The reaction became a deep red and was then diluted with water (300 mL), neutralized with 1N aqueous hydrochloric acid, and filtered, washing with water. The solid was dissolved in warm ethyl acetate (500 mL), dried (MgSO$_4$), treated with carbon (Norit A), filtered through celite, and concentrated. The residue was recrystallized from ethyl acetate.hexane to provide 2.2 g (80%) of product as a red solid: mp 185°-187° C.; IR (KBr) 1722.0, 1615.3, 1487.4 cm$^{-1}$; $^1$H NMR (CDCll$_3$,200 MHz) δ6.99 (dd, 2H, J=2.3, 6.4 Hz), 6.76 (dd, 2H, J=2.3, 10.7 Hz), 3.90 (s, 6H); MS m/z 376 (M+). Anal calcd for C$_{15}$H$_{10}$F$_2$O$_3$: C, 65.22; H, 3.65. Found: C, 65.31, H, 3.79.

EXAMPLE XXXX 2,7-Difluoro-4,5-dimethoxyspiro (9H-fluorene 9,4'-imidazolidine)-2',5'-dione A mixture of 2,7-Difluoro-4,5-dimethoxy fluorenone (1.5 g, 5.3 mmol), potassium cyanide (1.4 g, 21.2 mmol, 4 eq) and ammonium carbonate (1.5 g, 15.9 mmol, 3 eq) in 70 mL of ethanol was heated in a sealed bomb at 114° C. for 18 h. The bomb was then cooled and the mixture partitioned between 1N aqueous sodium hydroxide (100 mL) and a 1:1 mixture of ethyl acetate/hexane (100 mL). The basic aqueous phase was separated and the organic phase was extracted with 1N aqueous sodium hydroxide (3×74 mL). The combined basic aqueous layers were washed with ether (2×100 mL), dried (MgSO$_4$), treated with carbon (Norit A), filtered through celite, and concentrated to provide 1.37 g (70%) of crude material. This material was combined with an additional 425 mg of crude material obtained in the same fashion and first leached with ethanol and then crystallized from ethanol to provide 1.5 g (58%) of product as a white solid; mp>326° C.; IR (KBr) 3328.6, 1779.3, 1715.1, 1607.4 cm$^{-1}$; $^1$H NMR (DMSO d$_6$, 200 MHz) δ11.24 (a, 1H, D$_2$O exchangeable), 8.64 (s, 1H, D$_2$O exchangeable), 6.96 (m, 4H), 3.87 (s, 6H); MS m/z 346 (M+), base peak 275. Anal calcd for C$_{17}$H$_{12}$N$_2$O$_4$F$_2$: C, 58.96; H, 3.49; N, 8.09. Found: C, 59.01; H, 3.59; N, 8.09.

I claim:

1. A compound of the formula

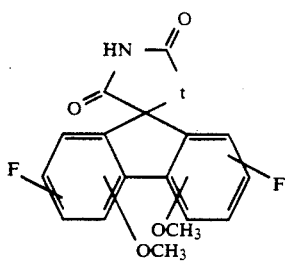

wherein t is selected from the group consisting of O, S and CHR' wherein R' is hydrogen or lower alkyl of 1 to 5 carbon atoms.

2. A compound according to claim 1 wherein the fluoro and methoxy substituents are located on the rings in meta position to each other.

3. A pharmaceutical composition for the treatment of complications of diabetes mellitus in humans comprising an effective amount of a compound of claim 1 and a pharmaceutical vehicle.

4. A composition according to claim 3 wherein the concentration of the compound in the vehicle is at a level ranging from about 0.5 percent to about 90 percent by weight.

5. A method for the treatment of complications of diabetes mellitus in humans and animals comprising administering thereto a composition of claim 3.

6. A method according to claim 5 wherein the composition is administered in oral form.

7. A method according to claim 5 wherein the composition is administered in a dosage amount of about 0.1 mg to about 10 mg/kg of body weight per day.

* * * * *